United States Patent
Soliman et al.

(10) Patent No.: US 11,155,634 B2
(45) Date of Patent: *Oct. 26, 2021

(54) TAG-72-BINDING CHIMERIC ANTIGEN RECEPTORS

(71) Applicant: H. Lee Moffitt Cancer Center and Research Institute, Inc., Tampa, FL (US)

(72) Inventors: Hatem Soliman, Tampa, FL (US); Macro Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 104 days.

This patent is subject to a terminal disclaimer.

(21) Appl. No.: 16/463,583

(22) PCT Filed: Nov. 30, 2017

(86) PCT No.: PCT/US2017/063950
§ 371 (c)(1),
(2) Date: May 23, 2019

(87) PCT Pub. No.: WO2018/102547
PCT Pub. Date: Jun. 7, 2018

(65) Prior Publication Data
US 2019/0276555 A1    Sep. 12, 2019

Related U.S. Application Data

(60) Provisional application No. 62/429,242, filed on Dec. 2, 2016, provisional application No. 62/449,896, filed on Jan. 24, 2017.

(51) Int. Cl.
| | | |
|---|---|---|
| *C07K 16/30* | (2006.01) |
| *A61K 35/17* | (2015.01) |
| *C07K 16/28* | (2006.01) |
| *C07K 14/725* | (2006.01) |
| *C07K 14/705* | (2006.01) |
| *C07K 19/00* | (2006.01) |

(52) U.S. Cl.
CPC .......... *C07K 16/3092* (2013.01); *A61K 35/17* (2013.01); *C07K 14/705* (2013.01); *C07K 14/7051* (2013.01); *C07K 16/2818* (2013.01); *C07K 16/2827* (2013.01); *C07K 19/00* (2013.01); *C07K 2317/622* (2013.01); *C07K 2317/92* (2013.01); *C07K 2319/02* (2013.01); *C07K 2319/03* (2013.01)

(58) Field of Classification Search
CPC ............ C07K 16/3092; C07K 14/7051; C07K 16/2818; C07K 16/2827; C07K 2317/622; C07K 2319/02; C07K 2319/03; A61K 35/17
See application file for complete search history.

(56) References Cited

U.S. PATENT DOCUMENTS

| | | | |
|---|---|---|---|
| 2002/0173035 A1 | 11/2002 | Lee et al. |
| 2002/0183497 A1 | 12/2002 | Anderson et al. |
| 2017/0209492 A1* | 7/2017 | June ................ A61K 39/001113 |
| 2019/0315882 A1* | 10/2019 | Soliman ............. C07K 16/3015 |

FOREIGN PATENT DOCUMENTS

| | | |
|---|---|---|
| WO | 2016033331 A1 | 3/2016 |
| WO | 2016089610 A1 | 6/2016 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
International Search Report for application PCT/US2017/063950, dated May 4, 2018.

* cited by examiner

*Primary Examiner* — Brad Duffy
*Assistant Examiner* — Cheom-Gil Cheong
(74) *Attorney, Agent, or Firm* — Thomas|Horstemeyer LLP

(57) ABSTRACT

Disclosed herein are chimeric antigen receptor (CAR) polypeptides that can be used with adoptive cell transfer to target and kill TAG-72-expressing cancers. Also disclosed are immune effector cells, such as T cells or Natural Killer (NK) cells, that are engineered to express these CARs. Therefore, also disclosed are methods of providing an anti-tumor immunity in a subject with a TAG-72-expressing cancer that involves adoptive transfer of the disclosed immune effector cells engineered to express the disclosed CARs.

16 Claims, 8 Drawing Sheets
Specification includes a Sequence Listing.

SEQUENCE LISTING

```
<160> NUMBER OF SEQ ID NOS: 53

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp His Ala Ile His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Leu Asn Met Ala Tyr
1               5

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Trp Ile Gly Tyr Phe Ser Pro Gly Asn Asp Asp Phe Arg Tyr Asn Glu
1               5                   10                  15

Arg Phe Lys Gly
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Trp Ile Gly Tyr Phe Ser Pro Gly Asn Asp Asp Phe Lys Tyr Asn Glu
1               5                   10                  15
```

Arg Tyr Lys Gly
        20

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Trp Ile Gly Tyr Phe Ser Pro Gly Asn Asn Asp Phe Lys Tyr Asn Glu
1               5                   10                  15

Arg Phe Lys Gly
        20

<210> SEQ ID NO 6
<211> LENGTH: 115
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Arg Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Tyr
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys

```
                    85                  90                  95
Thr Arg Ser Leu Asn Met Ala Tyr Trp Gly Gln Gly Thr Ser Val Thr
                100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asn Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
                100                 105                 110

Val Ser Ser
        115

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Lys Ser Ser Gln Ser Leu Leu Tyr Ser Gly Asn Gln Lys Asn Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Trp Ala Ser Ala Arg Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11
```

```
Gln Gln Tyr Tyr Ser Tyr Pro Leu Thr
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Tyr Ser Gly Asn His Lys Asn Tyr Leu
1               5                   10                  15

Ala

<210> SEQ ID NO 13
<211> LENGTH: 113
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 14
<211> LENGTH: 113
<212> TYPE: PRT
<213> ORGANISM: Artificial Sequence
<220> FEATURE:
<223> OTHER INFORMATION: Synthetic Construct

<400> SEQUENCE: 14

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95
```

Tyr Tyr Ser Tyr Pro Leu Thr Phe Gly Ala Gly Thr Lys Leu Val Leu
            100                 105                 110

Lys

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Leu Ser Ala Asp Asp Ala Lys Lys Asp Ala Ala Lys Lys Asp Asp Ala
1               5                   10                  15

Lys Lys Asp Asp Ala Lys Lys Asp Leu
            20                  25

<210> SEQ ID NO 16
<211> LENGTH: 253
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Asp Ala Lys Lys Asp Ala Ala Lys Lys Asp Asp
        115                 120                 125

Ala Lys Lys Asp Asp Ala Lys Lys Asp Leu Gln Val Gln Leu Gln Gln
    130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Arg Tyr Asn Glu Arg Phe Lys Gly Lys Ala Thr Leu
        195                 200                 205

Thr Ala Asp Lys Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 17
<211> LENGTH: 253
<212> TYPE: PRT
<213> ORGANISM: Artificial Sequence
<220> FEATURE:
<223> OTHER INFORMATION: Synthetic Construct

<400> SEQUENCE: 17

```
Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
                100                 105                 110

Lys Leu Ser Ala Asp Asp Ala Lys Lys Asp Ala Lys Lys Asp Asp
            115                 120                 125

Ala Lys Lys Asp Asp Ala Lys Lys Gly Leu Gln Val Gln Leu Gln Gln
        130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Lys Tyr Asn Glu Arg Tyr Lys Gly Lys Ala Thr Leu
        195                 200                 205

Thr Ala Asp Lys Ser Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250
```

<210> SEQ ID NO 18
<211> LENGTH: 253
<212> TYPE: PRT
<213> ORGANISM: Artificial Sequence
<220> FEATURE:
<223> OTHER INFORMATION: Synthetic Construct

<400> SEQUENCE: 18

```
Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
```

```
                50                  55                  60
Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                 85                  90                  95

Tyr Tyr Ser Tyr Pro Leu Thr Phe Gly Ala Gly Thr Lys Leu Val Leu
                100                 105                 110

Lys Leu Ser Ala Asp Asp Ala Lys Asp Ala Ala Lys Lys Asp Asp
                115                 120                 125

Ala Lys Lys Asp Asp Ala Lys Lys Asp Leu Gln Val Gln Leu Gln Gln
                130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
                180                 185                 190

Asn Asn Asp Phe Lys Tyr Asn Glu Arg Phe Lys Gly Lys Ala Thr Leu
                195                 200                 205

Thr Ala Asp Lys Ser Ser Ser Thr Ala Tyr Val Gln Leu Asn Ser Leu
                210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Asp His Ala Ile His
 1               5

<210> SEQ ID NO 20
<211> LENGTH: 20
<212> TYPE: PRT
<213> ORGANISM: Artificial Sequence
<220> FEATURE:
<223> OTHER INFORMATION: Synthetic Construct

<400> SEQUENCE: 20

Trp Ile Gly Tyr Phe Ser Pro Gly Asn Asp Asp Phe Lys Tyr Asn Glu
 1               5                  10                  15

Arg Phe Lys Gly
                20

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Leu Asn Met Ala Tyr
 1               5
```

```
<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Lys Ser Ser Gln Ser Leu Leu Tyr Ser Gly Asn Gln Lys Asn Tyr Leu
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Trp Ala Ser Ala Arg Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Tyr Tyr Ser Tyr Pro Leu Thr
1               5

<210> SEQ ID NO 25
<211> LENGTH: 115
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 26
<211> LENGTH: 113
```

```
<212> TYPE: PRT
<213> ORGANISM: Artificial Sequence
<220> FEATURE:
<223> OTHER INFORMATION: Synthetic Construct

<400> SEQUENCE: 26

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 27
<211> LENGTH: 253
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Leu Ser Ala Asp Asp Ala Lys Lys Asp Ala Ala Lys Lys
        115                 120                 125

Asp Asp Ala Lys Lys Asp Asp Ala Lys Lys Asp Leu Asp Ile Val Met
    130                 135                 140

Ser Gln Ser Pro Ser Ser Leu Pro Val Ser Gly Glu Lys Val Thr
145                 150                 155                 160

Leu Ser Cys Lys Ser Ser Gln Ser Leu Leu Tyr Ser Gly Asn Gln Lys
                165                 170                 175

Asn Tyr Leu Ala Trp Tyr Gln Gln Lys Pro Gly Gln Ser Pro Lys Leu
            180                 185                 190

Leu Ile Tyr Trp Ala Ser Ala Arg Glu Ser Gly Val Pro Asp Arg Phe
        195                 200                 205
```

```
Thr Gly Ser Gly Ser Gly Thr Asp Phe Thr Leu Ser Ile Ser Ser Val
    210                 215                 220

Lys Thr Glu Asp Leu Ala Val Tyr Tyr Cys Gln Gln Tyr Tyr Ser Tyr
225                 230                 235                 240

Pro Leu Thr Phe Gly Ala Gly Thr Lys Leu Val Leu Lys
            245                 250

<210> SEQ ID NO 28
<211> LENGTH: 253
<212> TYPE: PRT
<213> ORGANISM: Artificial Sequence
<220> FEATURE:
<223> OTHER INFORMATION: Synthetic Construct

<400> SEQUENCE: 28

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Asp Ala Lys Lys Asp Ala Ala Lys Lys Asp Asp
        115                 120                 125

Ala Lys Lys Asp Asp Ala Lys Lys Asp Leu Gln Val Gln Leu Gln Gln
    130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Lys Tyr Asn Glu Arg Phe Lys Gly Lys Ala Thr Leu
        195                 200                 205

Thr Ala Asp Lys Ser Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 29
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is val or gln
<220> FEATURE:
```

```
<221> NAME/KEY: MISC_FEATURE
<222> LOCATION: (6)..(6)
<223> OTHER INFORMATION: Xaa is gln or glu
<220> FEATURE:
<221> NAME/KEY: MISC_FEATURE
<222> LOCATION: (8)..(8)
<223> OTHER INFORMATION: Xaa is asp or gly
<220> FEATURE:
<221> NAME/KEY: MISC_FEATURE
<222> LOCATION: (9)..(9)
<223> OTHER INFORMATION: Xaa is ala or pro
<220> FEATURE:
<221> NAME/KEY: MISC_FEATURE
<222> LOCATION: (10)..(10)
<223> OTHER INFORMATION: Xaa is glu or gly
<220> FEATURE:
<221> NAME/KEY: MISC_FEATURE
<222> LOCATION: (11)..(11)
<223> OTHER INFORMATION: Xaa is leu or val
<220> FEATURE:
<221> NAME/KEY: MISC_FEATURE
<222> LOCATION: (12)..(12)
<223> OTHER INFORMATION: Xaa is val or lys
<220> FEATURE:
<221> NAME/KEY: MISC_FEATURE
<222> LOCATION: (13)..(13)
<223> OTHER INFORMATION: Xaa is lys or arg
<220> FEATURE:
<221> NAME/KEY: MISC_FEATURE
<222> LOCATION: (15)..(15)
<223> OTHER INFORMATION: Xaa is gly or ser
<220> FEATURE:
<221> NAME/KEY: MISC_FEATURE
<222> LOCATION: (16)..(16)
<223> OTHER INFORMATION: Xaa is ala or gln
<220> FEATURE:
<221> NAME/KEY: MISC_FEATURE
<222> LOCATION: (17)..(17)
<223> OTHER INFORMATION: Xaa is ser or thr
<220> FEATURE:
<221> NAME/KEY: MISC_FEATURE
<222> LOCATION: (18)..(18)
<223> OTHER INFORMATION: Xaa is val or leu
<220> FEATURE:
<221> NAME/KEY: MISC_FEATURE
<222> LOCATION: (19)..(19)
<223> OTHER INFORMATION: Xaa is lys or ser
<220> FEATURE:
<221> NAME/KEY: MISC_FEATURE
<222> LOCATION: (20)..(20)
<223> OTHER INFORMATION: Xaa is ile, leu, or val
<220> FEATURE:
<221> NAME/KEY: MISC_FEATURE
<222> LOCATION: (21)..(21)
<223> OTHER INFORMATION: Xaa is ser or thr
<220> FEATURE:
<221> NAME/KEY: MISC_FEATURE
<222> LOCATION: (23)..(23)
<223> OTHER INFORMATION: Xaa is lys or thr
<220> FEATURE:
<221> NAME/KEY: MISC_FEATURE
<222> LOCATION: (24)..(24)
<223> OTHER INFORMATION: Xaa is ala or val
<220> FEATURE:
<221> NAME/KEY: MISC_FEATURE
<222> LOCATION: (31)..(31)
<223> OTHER INFORMATION: Xaa is thr or nothing
<220> FEATURE:
<221> NAME/KEY: MISC_FEATURE
<222> LOCATION: (39)..(39)
<223> OTHER INFORMATION: Xaa is lys or arg
<220> FEATURE:
<221> NAME/KEY: MISC_FEATURE
<222> LOCATION: (41)..(41)
<223> OTHER INFORMATION: Xaa is asn, lys, pro, or ala
<220> FEATURE:
<221> NAME/KEY: MISC_FEATURE
<222> LOCATION: (43)..(43)
<223> OTHER INFORMATION: Xaa is glu or gly
```

-continued

```
<220> FEATURE:
<221> NAME/KEY: MISC_FEATURE
<222> LOCATION: (44)..(44)
<223> OTHER INFORMATION: Xaa is gln or arg
<220> FEATURE:
<221> NAME/KEY: MISC_FEATURE
<222> LOCATION: (45)..(45)
<223> OTHER INFORMATION: Xaa is gly or arg
<220> FEATURE:
<221> NAME/KEY: MISC_FEATURE
<222> LOCATION: (49)..(49)
<223> OTHER INFORMATION: Xaa is ile or met
<220> FEATURE:
<221> NAME/KEY: MISC_FEATURE
<222> LOCATION: (52)..(52)
<223> OTHER INFORMATION: Xaa is phe or ile
<220> FEATURE:
<221> NAME/KEY: MISC_FEATURE
<222> LOCATION: (55)..(55)
<223> OTHER INFORMATION: Xaa is gly or gln
<220> FEATURE:
<221> NAME/KEY: MISC_FEATURE
<222> LOCATION: (57)..(57)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is phe or ile
<220> FEATURE:
<221> NAME/KEY: MISC_FEATURE
<222> LOCATION: (60)..(60)
<223> OTHER INFORMATION: Xaa is lys or arg
<220> FEATURE:
<221> NAME/KEY: MISC_FEATURE
<222> LOCATION: (62)..(62)
<223> OTHER INFORMATION: Xaa is asn or ser
<220> FEATURE:
<221> NAME/KEY: MISC_FEATURE
<222> LOCATION: (63)..(63)
<223> OTHER INFORMATION: Xaa is glu or gln
<220> FEATURE:
<221> NAME/KEY: MISC_FEATURE
<222> LOCATION: (64)..(64)
<223> OTHER INFORMATION: Xaa is arg or lys
<220> FEATURE:
<221> NAME/KEY: MISC_FEATURE
<222> LOCATION: (65)..(65)
<223> OTHER INFORMATION: Xaa is phe or tyr
<220> FEATURE:
<221> NAME/KEY: MISC_FEATURE
<222> LOCATION: (66)..(66)
<223> OTHER INFORMATION: Xaa is lys or gln
<220> FEATURE:
<221> NAME/KEY: MISC_FEATURE
<222> LOCATION: (68)..(68)
<223> OTHER INFORMATION: Xaa is lys or arg
<220> FEATURE:
<221> NAME/KEY: MISC_FEATURE
<222> LOCATION: (69)..(69)
<223> OTHER INFORMATION: Xaa is ala or val
<220> FEATURE:
<221> NAME/KEY: MISC_FEATURE
<222> LOCATION: (71)..(71)
<223> OTHER INFORMATION: Xaa is leu, met, or ile
<220> FEATURE:
<221> NAME/KEY: MISC_FEATURE
<222> LOCATION: (72)..(72)
<223> OTHER INFORMATION: Xaa is thr or leu
<220> FEATURE:
<221> NAME/KEY: MISC_FEATURE
<222> LOCATION: (73)..(73)
<223> OTHER INFORMATION: Xaa is ala, val, or arg
<220> FEATURE:
<221> NAME/KEY: MISC_FEATURE
<222> LOCATION: (75)..(75)
<223> OTHER INFORMATION: Xaa is lys or thr
<220> FEATURE:
<221> NAME/KEY: MISC_FEATURE
<222> LOCATION: (76)..(76)
```

```
<223> OTHER INFORMATION: Xaa is ser or pro
<220> FEATURE:
<221> NAME/KEY: MISC_FEATURE
<222> LOCATION: (77)..(77)
<223> OTHER INFORMATION: Xaa is ser, ala, or lys
<220> FEATURE:
<221> NAME/KEY: MISC_FEATURE
<222> LOCATION: (78)..(78)
<223> OTHER INFORMATION: Xaa is ser or asn
<220> FEATURE:
<221> NAME/KEY: MISC_FEATURE
<222> LOCATION: (79)..(79)
<223> OTHER INFORMATION: Xaa is thr or gln
<220> FEATURE:
<221> NAME/KEY: MISC_FEATURE
<222> LOCATION: (80)..(80)
<223> OTHER INFORMATION: Xaa is ala, val, or phe
<220> FEATURE:
<221> NAME/KEY: MISC_FEATURE
<222> LOCATION: (81)..(81)
<223> OTHER INFORMATION: Xaa is tyr or ser
<220> FEATURE:
<221> NAME/KEY: MISC_FEATURE
<222> LOCATION: (82)..(82)
<223> OTHER INFORMATION: Xaa is val, met, or leu
<220> FEATURE:
<221> NAME/KEY: MISC_FEATURE
<222> LOCATION: (83)..(83)
<223> OTHER INFORMATION: Xaa is gln, glu, or arg
<220> FEATURE:
<221> NAME/KEY: MISC_FEATURE
<222> LOCATION: (85)..(85)
<223> OTHER INFORMATION: Xaa is asn or ser
<220> FEATURE:
<221> NAME/KEY: MISC_FEATURE
<222> LOCATION: (87)..(87)
<223> OTHER INFORMATION: Xaa is leu or val
<220> FEATURE:
<221> NAME/KEY: MISC_FEATURE
<222> LOCATION: (88)..(88)
<223> OTHER INFORMATION: Xaa is thr, pro, or arg
<220> FEATURE:
<221> NAME/KEY: MISC_FEATURE
<222> LOCATION: (89)..(89)
<223> OTHER INFORMATION: Xaa is ser or ala
<220> FEATURE:
<221> NAME/KEY: MISC_FEATURE
<222> LOCATION: (90)..(90)
<223> OTHER INFORMATION: Xaa is glu, asn, or ala
<220> FEATURE:
<221> NAME/KEY: MISC_FEATURE
<222> LOCATION: (92)..(92)
<223> OTHER INFORMATION: Xaa is ser or thr
<220> FEATURE:
<221> NAME/KEY: MISC_FEATURE
<222> LOCATION: (96)..(96)
<223> OTHER INFORMATION: Xaa is phe or tyr
<220> FEATURE:
<221> NAME/KEY: MISC_FEATURE
<222> LOCATION: (98)..(98)
<223> OTHER INFORMATION: Xaa is thr, arg, or ala
<220> FEATURE:
<221> NAME/KEY: MISC_FEATURE
<222> LOCATION: (101)..(101)
<223> OTHER INFORMATION: Xaa is leu, phe, or tyr
<220> FEATURE:
<221> NAME/KEY: MISC_FEATURE
<222> LOCATION: (102)..(102)
<223> OTHER INFORMATION: Xaa is asn, tyr, or ser
<220> FEATURE:
<221> NAME/KEY: MISC_FEATURE
<222> LOCATION: (103)..(103)
<223> OTHER INFORMATION: Xaa is met or gly
<220> FEATURE:
<221> NAME/KEY: MISC_FEATURE
<222> LOCATION: (104)..(104)
<223> OTHER INFORMATION: Xaa is ala, asn, asp, or his
<220> FEATURE:
<221> NAME/KEY: MISC_FEATURE
```

```
<222> LOCATION: (105)..(105)
<223> OTHER INFORMATION: Xaa is tyr, ser, or nothing
<220> FEATURE:
<221> NAME/KEY: MISC_FEATURE
<222> LOCATION: (110)..(110)
<223> OTHER INFORMATION: Xaa is thr or ser
<220> FEATURE:
<221> NAME/KEY: MISC_FEATURE
<222> LOCATION: (111)..(111)
<223> OTHER INFORMATION: Xaa is ser, thr, or leu
<220> FEATURE:
<221> NAME/KEY: MISC_FEATURE
<222> LOCATION: (112)..(112)
<223> OTHER INFORMATION: Xaa is val or leu

<400> SEQUENCE: 29

Gln Val Gln Leu Xaa Xaa Ser Xaa Xaa Xaa Xaa Xaa Pro Xaa Xaa
1               5                   10                  15

Xaa Xaa Xaa Xaa Xaa Cys Xaa Xaa Ser Gly Tyr Thr Phe Thr Xaa Asp
            20                  25                  30

His Ala Ile His Trp Val Xaa Gln Xaa Pro Xaa Xaa Xaa Leu Trp Glu
            35                  40                  45

Xaa Gly Tyr Xaa Ser Pro Xaa Asn Xaa Asp Xaa Xaa Tyr Xaa Xaa Xaa
    50                  55                  60

Xaa Xaa Gly Xaa Xaa Thr Xaa Xaa Xaa Asp Xaa Xaa Xaa Xaa Xaa Xaa
65              70                  75                  80

Xaa Xaa Xaa Leu Xaa Ser Xaa Xaa Xaa Asp Xaa Ala Val Tyr Xaa
                85                  90                  95

Cys Xaa Arg Ser Xaa Xaa Xaa Xaa Xaa Trp Gly Gln Gly Xaa Xaa Xaa
            100                 105                 110

Thr Val Ser Ser
        115

<210> SEQ ID NO 30
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is ile or met
<220> FEATURE:
<221> NAME/KEY: MISC_FEATURE
<222> LOCATION: (5)..(5)
<223> OTHER INFORMATION: Xaa is phe or ile
<220> FEATURE:
<221> NAME/KEY: MISC_FEATURE
<222> LOCATION: (8)..(8)
<223> OTHER INFORMATION: Xaa is gly or gln
<220> FEATURE:
<221> NAME/KEY: MISC_FEATURE
<222> LOCATION: (10)..(10)
<223> OTHER INFORMATION: Xaa is asp or asn
<220> FEATURE:
<221> NAME/KEY: MISC_FEATURE
<222> LOCATION: (12)..(12)
<223> OTHER INFORMATION: Xaa is phe or ile
<220> FEATURE:
<221> NAME/KEY: MISC_FEATURE
<222> LOCATION: (13)..(13)
<223> OTHER INFORMATION: Xaa is lys or arg
<220> FEATURE:
<221> NAME/KEY: MISC_FEATURE
<222> LOCATION: (15)..(15)
<223> OTHER INFORMATION: Xaa is asn or ser
<220> FEATURE:
<221> NAME/KEY: MISC_FEATURE
<222> LOCATION: (16)..(16)
```

<223> OTHER INFORMATION: Xaa is glu or gln
<220> FEATURE:
<221> NAME/KEY: MISC_FEATURE
<222> LOCATION: (17)..(17)
<223> OTHER INFORMATION: Xaa is arg or lys
<220> FEATURE:
<221> NAME/KEY: MISC_FEATURE
<222> LOCATION: (18)..(18)
<223> OTHER INFORMATION: Xaa is phe or tyr
<220> FEATURE:
<221> NAME/KEY: MISC_FEATURE
<222> LOCATION: (19)..(19)
<223> OTHER INFORMATION: Xaa is lys or gln

<400> SEQUENCE: 30

Trp Xaa Gly Tyr Xaa Ser Pro Xaa Asn Xaa Asp Xaa Xaa Tyr Xaa Xaa
1               5                   10                  15

Xaa Xaa Xaa Gly
            20

<210> SEQ ID NO 31
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 31

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Xaa Asp Phe Xaa Tyr Asn Glu Arg Xaa
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (57)..(57)
<223> OTHER INFORMATION: Xaa can be any naturally occurring amino acid

```
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

<400> SEQUENCE: 32
```

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Thr Asp
            20                  25                  30

His Ala Ile His Trp Val Lys Gln Asn Pro Glu Gln Gly Leu Glu Trp
        35                  40                  45

Ile Gly Tyr Phe Ser Pro Gln Asn Xaa Asp Phe Xaa Tyr Asn Glu Arg
    50                  55                  60

Xaa Lys Gly Lys Ala Thr Leu Thr Ala Asp Lys Ser Ser Ser Thr Ala
65                  70                  75                  80

Tyr Val Gln Leu Asn Ser Leu Thr Ser Asn Asp Ser Ala Val Tyr Phe
                85                  90                  95

Cys Thr Arg Ser Leu Asn Met Ala Tyr Trp Gly Gln Gly Thr Ser Val
            100                 105                 110

Thr Val Ser Ser
            115

```
<210> SEQ ID NO 33
<211> LENGTH: 104
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

<400> SEQUENCE: 33
```

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Thr Asp
            20                  25                  30

His Ala Ile His Trp Val Lys Gln Asn Pro Glu Gln Gly Leu Glu Trp
        35                  40                  45

Ile Gly Tyr Ile Ser Pro Gln Asn Xaa Asp Ile Xaa Tyr Asn Glu Lys
    50                  55                  60

Xaa Lys Gly Lys Ala Thr Leu Thr Ala Asp Lys Ser Ser Ser Thr Ala
65                  70                  75                  80

Tyr Met Gln Leu Asn Ser Leu Thr Ser Asn Asp Ser Ala Val Tyr Phe
                85                  90                  95

Cys Arg Arg Ser Phe Tyr Gly Asn
            100

```
<210> SEQ ID NO 34
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

<400> SEQUENCE: 34

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Thr Asp
            20                  25                  30

His Ala Ile His Trp Val Lys Gln Lys Pro Glu Gln Gly Leu Glu Trp
        35                  40                  45

Ile Gly Tyr Ile Ser Pro Gln Asn Xaa Asp Ile Xaa Tyr Asn Glu Lys
    50                  55                  60

Xaa Lys Gly Lys Ala Thr Leu Thr Ala Asp Lys Pro Ser Asn Thr Val
65                  70                  75                  80

Tyr Met Gln Leu Asn Ser Leu Thr Ser Asn Asp Ser Ala Val Tyr Phe
                85                  90                  95

Cys Thr Arg Ser Leu Ser Gly Asp Ser Trp Gly Gln Gly Thr Thr Leu
            100                 105                 110

Thr Val Ser Ser
            115

<210> SEQ ID NO 35
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 35

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Xaa Asp Phe Xaa Tyr Asn Glu Arg Xaa
    50                  55                  60
```

```
Lys Gly Lys Ala Thr Leu Thr Ala Asp Thr Ser Ala Ser Thr Ala Tyr
 65                  70                  75                  80

Val Glu Leu Ser Ser Leu Pro Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser
        115

<210> SEQ ID NO 36
<211> LENGTH: 103
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 36

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Ile Ser Pro Gly Asn Xaa Asp Ile Xaa Tyr Asn Glu Lys Xaa
    50                  55                  60

Lys Gly Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Tyr Tyr Gly His
            100

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is asp or asn
<220> FEATURE:
<221> NAME/KEY: MISC_FEATURE
<222> LOCATION: (64)..(64)
<223> OTHER INFORMATION: Xaa is phe or tyr

<400> SEQUENCE: 37

Gln Val Gln Leu Val Gln Ser Gly Ala Glu Val Val Lys Pro Gly Ala
1               5                   10                  15
```

```
Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
            35                  40                  45

Gly Tyr Phe Ser Pro Gly Asn Xaa Asp Phe Xaa Tyr Ser Gln Lys Xaa
            50                  55                  60

Gln Gly Lys Ala Thr Leu Thr Ala Asp Thr Ser Ala Ser Thr Ala Tyr
 65                  70                  75                  80

Val Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 38

Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Asp His
            20                  25                  30

Ala Ile His Trp Val Arg Gln Asn Pro Gly Gln Arg Leu Glu Trp Met
            35                  40                  45

Gly Tyr Phe Ser Pro Gly Asn Xaa Asp Phe Xaa Tyr Ser Gln Lys Xaa
            50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser
        115

<210> SEQ ID NO 39
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
```

```
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
        115

<210> SEQ ID NO 40
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 40

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Xaa Asp Phe Xaa Tyr Asn Glu Arg Xaa
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Thr Leu Thr
            100                 105                 110

Val Ser Ser
```

```
<210> SEQ ID NO 41
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
            100                 105                 110

Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45
```

Gly Tyr Phe Ser Pro Gly Asn Xaa Asp Phe Xaa Tyr Ser Gln Lys Xaa
            50                  55                  60

Gln Gly Arg Val Thr Ile Thr Arg Asp Lys Ser Ala Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
                100                 105                 110

Val Ser Ser
        115

<210> SEQ ID NO 43
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)
<223> OTHER INFORMATION: Xaa is phe or tyr

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Arg Leu Glu Trp Met
            35                  40                  45

Gly Tyr Phe Ser Pro Gly Asn Xaa Asp Phe Xaa Tyr Ser Gln Lys Xaa
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
                100                 105                 110

Val Ser Ser
        115

<210> SEQ ID NO 44
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is asp or asn
<220> FEATURE:
<221> NAME/KEY: MISC_FEATURE
<222> LOCATION: (59)..(59)
<223> OTHER INFORMATION: Xaa is lys or arg
<220> FEATURE:
<221> NAME/KEY: MISC_FEATURE
<222> LOCATION: (64)..(64)

<223> OTHER INFORMATION: Xaa is phe or tyr

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
            100                 105                 110

Val Ser Ser
        115

<210> SEQ ID NO 45
<211> LENGTH: 113
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is ser or thr
<220> FEATURE:
<221> NAME/KEY: MISC_FEATURE
<222> LOCATION: (9)..(9)
<223> OTHER INFORMATION: Xaa is ser or asp
<220> FEATURE:
<221> NAME/KEY: MISC_FEATURE
<222> LOCATION: (12)..(12)
<223> OTHER INFORMATION: Xaa is pro or ala
<220> FEATURE:
<221> NAME/KEY: MISC_FEATURE
<222> LOCATION: (15)..(15)
<223> OTHER INFORMATION: Xaa is leu or val
<220> FEATURE:
<221> NAME/KEY: MISC_FEATURE
<222> LOCATION: (17)..(17)
<223> OTHER INFORMATION: Xaa is glu or asp
<220> FEATURE:
<221> NAME/KEY: MISC_FEATURE
<222> LOCATION: (19)..(19)
<223> OTHER INFORMATION: Xaa is val or ala
<220> FEATURE:
<221> NAME/KEY: MISC_FEATURE
<222> LOCATION: (21)..(21)
<223> OTHER INFORMATION: Xaa is leu or ile
<220> FEATURE:
<221> NAME/KEY: MISC_FEATURE
<222> LOCATION: (22)..(22)
<223> OTHER INFORMATION: Xaa is ser or asn
<220> FEATURE:
<221> NAME/KEY: MISC_FEATURE
<222> LOCATION: (29)..(29)
<223> OTHER INFORMATION: Xaa is leu or val
<220> FEATURE:
<221> NAME/KEY: MISC_FEATURE
<222> LOCATION: (33)..(33)
<223> OTHER INFORMATION: Xaa is gly or ser
<220> FEATURE:
<221> NAME/KEY: MISC_FEATURE
<222> LOCATION: (49)..(49)
<223> OTHER INFORMATION: Xaa is ser or pro

```
<220> FEATURE:
<221> NAME/KEY: MISC_FEATURE
<222> LOCATION: (59)..(59)
<223> OTHER INFORMATION: Xaa is ala or thr
<220> FEATURE:
<221> NAME/KEY: MISC_FEATURE
<222> LOCATION: (69)..(69)
<223> OTHER INFORMATION: Xaa is thr or ser
<220> FEATURE:
<221> NAME/KEY: MISC_FEATURE
<222> LOCATION: (70)..(70)
<223> OTHER INFORMATION: Xaa is ser or thr
<220> FEATURE:
<221> NAME/KEY: MISC_FEATURE
<222> LOCATION: (74)..(74)
<223> OTHER INFORMATION: Xaa is val or leu
<220> FEATURE:
<221> NAME/KEY: MISC_FEATURE
<222> LOCATION: (75)..(75)
<223> OTHER INFORMATION: Xaa is lys or gln
<220> FEATURE:
<221> NAME/KEY: MISC_FEATURE
<222> LOCATION: (76)..(76)
<223> OTHER INFORMATION: Xaa is thr or ala
<220> FEATURE:
<221> NAME/KEY: MISC_FEATURE
<222> LOCATION: (79)..(79)
<223> OTHER INFORMATION: Xaa is leu or val
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: MISC_FEATURE
<222> LOCATION: (86)..(86)
<223> OTHER INFORMATION: Xaa is ala or gln
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: MISC_FEATURE
<222> LOCATION: (90)..(90)
<223> OTHER INFORMATION: Xaa is leu or val
<220> FEATURE:
<221> NAME/KEY: MISC_FEATURE
<222> LOCATION: (91)..(91)
<223> OTHER INFORMATION: Xaa is val or glu
<220> FEATURE:
<221> NAME/KEY: MISC_FEATURE
<222> LOCATION: (92)..(92)
<223> OTHER INFORMATION: Xaa is leu or ile
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (110)..(112)
<223> OTHER INFORMATION: Xaa can be any naturally occurring amino acid

<400> SEQUENCE: 45

Asp Ile Val Met Xaa Gln Ser Pro Xaa Ser Leu Xaa Val Ser Xaa Gly
1               5                   10                  15

Xaa Lys Xaa Thr Xaa Xaa Cys Lys Ser Ser Gln Ser Xaa Leu Tyr Ser
            20                  25                  30

Xaa Asn His Lys Asn Tyr Leu Ala Trp Tyr Gln Gln Lys Pro Gly Gln
        35                  40                  45

Xaa Pro Lys Leu Leu Ile Tyr Trp Ala Ser Xaa Arg Glu Ser Gly Val
    50                  55                  60
```

```
Pro Asp Arg Phe Xaa Gly Ser Gly Ser Gly Thr Asp Phe Thr Leu Xaa
 65                  70                  75                  80

Ile Ser Ser Xaa Xaa Xaa Glu Asp Xaa Ala Val Tyr Tyr Cys Gln Gln
                 85                  90                  95

Tyr Tyr Ser Tyr Pro Leu Thr Phe Gly Xaa Gly Thr Lys Xaa Xaa Xaa
            100                 105                 110

Lys
```

```
<210> SEQ ID NO 46
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is leu or val
<220> FEATURE:
<221> NAME/KEY: MISC_FEATURE
<222> LOCATION: (10)..(10)
<223> OTHER INFORMATION: Xaa is gly or ser

<400> SEQUENCE: 46

Lys Ser Ser Gln Ser Xaa Leu Tyr Ser Xaa Asn His Lys Asn Tyr Leu
 1               5                  10                  15

Ala
```

```
<210> SEQ ID NO 47
<211> LENGTH: 113
<212> TYPE: PRT
<213> ORGANISM: Artificial Sequence
<220> FEATURE:
<223> OTHER INFORMATION: Synthetic Construct

<400> SEQUENCE: 47

Asp Ile Val Met Ser Gln Ser Pro Asp Ser Leu Ala Val Ser Leu Gly
 1               5                  10                  15

Glu Arg Val Thr Leu Asn Cys Lys Ser Ser Gln Ser Leu Leu Tyr Ser
                20                  25                  30

Gly Asn His Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys
```

```
<210> SEQ ID NO 48
<211> LENGTH: 113
<212> TYPE: PRT
<213> ORGANISM: Artificial Sequence
<220> FEATURE:
<223> OTHER INFORMATION: Synthetic Construct

<400> SEQUENCE: 48

Asp Ile Val Met Ser Gln Ser Pro Asp Ser Leu Ala Val Ser Leu Gly
 1               5                  10                  15
```

```
Glu Arg Val Thr Leu Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 49
<211> LENGTH: 113
<212> TYPE: PRT
<213> ORGANISM: Artificial Sequence
<220> FEATURE:
<223> OTHER INFORMATION: Synthetic Construct

<400> SEQUENCE: 49

Asp Ile Val Met Ser Gln Thr Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Ile
            100                 105                 110

Lys

<210> SEQ ID NO 50
<211> LENGTH: 113
<212> TYPE: PRT
<213> ORGANISM: Artificial Sequence
<220> FEATURE:
<223> OTHER INFORMATION: Synthetic Construct

<400> SEQUENCE: 50

Asp Ile Val Met Ser Gln Thr Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gln Gly Thr Lys Leu Glu Ile
            100                 105                 110

Lys

<210> SEQ ID NO 51
<211> LENGTH: 113
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Ser Gln Ser Pro Ser Ser Leu Pro Val Ser Val Gly
1               5                   10                  15

Asp Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Ile
            100                 105                 110

Lys

<210> SEQ ID NO 52
<211> LENGTH: 113
<212> TYPE: PRT
<213> ORGANISM: Artificial Sequence
<220> FEATURE:
<223> OTHER INFORMATION: Synthetic Construct

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn His Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys

<210> SEQ ID NO 53
<211> LENGTH: 113
<212> TYPE: PRT
<213> ORGANISM: Artificial Sequence
```

```
<220> FEATURE:
<223> OTHER INFORMATION: Synthetic Construct

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Gly Asn His Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys
```

TAG-72-BINDING CHIMERIC ANTIGEN RECEPTORS

CROSS-REFERENCE TO RELATED APPLICATIONS

This application claims benefit of U.S. Provisional Application No. 62/429,242, filed Dec. 2, 2016, and Application Ser. No. 62/449,896, filed Jan. 24, 2017, which are hereby incorporated herein by reference in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Disclosed herein are chimeric antigen receptor (CAR) polypeptides that can be used with adoptive cell transfer to target and kill TAG-72-expressing cancers. The disclosed CAR polypeptides contain in an ectodomain an anti-TAG-72 binding agent that can bind TAG-72-expressing cancer cells. The anti-TAG-72 binding agent is in some embodiments an antibody fragment that specifically binds TAG-72. For example, the antigen binding domain can be a Fab or a single-chain variable fragment (scFv) of an antibody that specifically binds TAG-72. The anti-TAG-72 binding agent is in some embodiments an aptamer that specifically binds TAG-72. For example, the anti-TAG-72 binding agent can be a peptide aptamer selected from a random sequence pool based on its ability to bind TAG-72. The anti-TAG-72 binding agent can also be a natural ligand of TAG-72, or a variant and/or fragment thereof capable of binding TAG-72.

In some embodiments, the anti-TAG-72 binding agent is an affinity maturated scFv. For example, the anti-TAG-72 scFv can comprise a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence DHAIH (SEQ ID NO:1), wherein the CDR2 sequence of the $V_H$ domain has an amino acid sequence selected from the group consisting of WIGYFSPGNDDFRYNERFKG (SEQ ID NO:3), WIGYFSPGNDDFKYNERYKG (SEQ ID NO:4), and WIGYFSPGNNDFKYNERFKG (SEQ ID NO:5), wherein the CDR3 sequence of the $V_H$ domain comprises the amino acid sequence LNMAY (SEQ ID NO:2), wherein the CDR1 sequence of the $V_L$ domain has an amino acid sequence selected from the group consisting of KSSQSLLYSGNQKNYLA (SEQ ID NO:9) and KSSQSLLYSGNHKNYLA (SEQ ID NO:12), wherein the CDR2 sequence of the $V_L$ domain comprises the amino acid sequence WASARES (SEQ ID NO:10), wherein the CDR3 sequence of the $V_L$ domain comprises the amino acid sequence KSSQSLLY-SGNHKNYLA (SEQ ID NO:12), or any combination thereof. Therefore, in some embodiments, the anti-TAG-72 scFv $V_H$ domain comprises the amino acid sequence SEQ ID NO:6, SEQ ID NO:7, or SEQ ID NO:8. In some embodiments, the anti-TAG-72 scFv $V_L$ domain comprises the amino acid sequence SEQ ID NO:13 or SEQ ID NO:14. Therefore, in some embodiments, the anti-TAG-72 scFv comprises an amino acid sequence selected from the group consisting of SEQ ID NO:16, SEQ ID NO:17, and SEQ ID NO:18.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to TAG-72.

Also disclosed is a method of providing an anti-tumor immunity in a subject with a TAG-72-expressing cancer that involves administering to the subject an effective amount of an immune effector cell genetically modified with a disclosed TAG-72-specific CAR.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
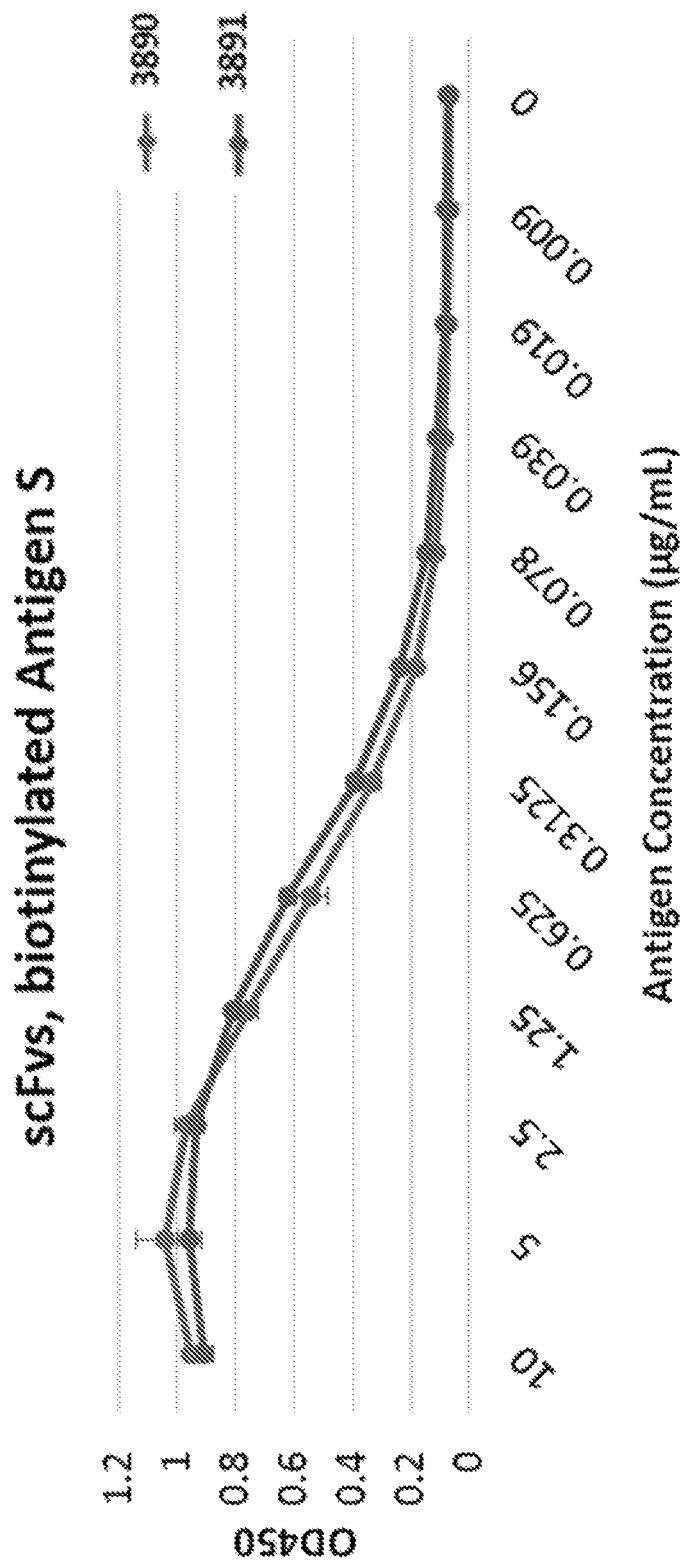
FIGS. 1A and 1B show binding of scFvs Ab3890 and Ab3891 to biotinylated antigen S FIG. 1A) and unmodified antigen S(FIG. 1B).

Disclosed herein are chimeric antigen receptors (CAR) that can specifically recognize tumor-associated antigens (TAA) on TAG-72-expressing cancers. Also disclosed are immune effector cells, such as T cells or Natural Killer (NK) cells, that are engineered to express these CARs. Therefore, also disclosed are methods for providing an anti-tumor immunity in a subject with TAG-72-expressing cancers that involves adoptive transfer of the disclosed immune effector cells engineered to express the disclosed TAG-72-specific CARs.

TAG-2-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a TAG-72-specific chimeric antigen receptor (CAR) that can be that can be expressed in immune effector cells to enhance antitumor activity against TAG-72-specific CARs.

The disclosed CAR is generally made up of three domains: an ectodomain, a transmembrane domain, and an endodomain. The ectodomain comprises the TAG-72-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain a signaling domain (SD) and optionally a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-TAG72-HG-TM-CSR-SD; or

SP-TAG72-HG-TM-CSR-SD, wherein "SP" represents an optional signal peptide,
wherein "TAG72" represents a TAG-72-binding region,
wherein "HG" represents an optional hinge domain,
wherein "TM" represents a transmembrane domain,
wherein "CSR" represents one or more co-stimulatory signaling regions,
wherein "SD" represents an intracellular signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3 domain. TanCAR T cell activation is achieved only when target cells co-express both targets.

A dual CAR T cell expresses two separate CARs with different ligand binding targets; one CAR includes only the CD3 domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ. CD3ε, CD32 (Fc gamma RIIa), DAP10, DAP12, CD79a, CD79b, FcγRIγ, FcγRIIIγ, FcεRIβ(FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3 chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3 signaling domain by itself or combined with any other desired cytoplasmic domain(s) useful in the context of the CAR of the invention. For example, the cytoplasmic domain of the CAR can comprise a CD3 chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-TAG-72 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS(CD278), 4-1BB(CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of TAG-72-binding region, co-stimulatory signaling regions, and intracellular signaling domain that can occur in the disclosed CARs. Tables 4 to 6 provide examples of combinations without either a signaling domain or a co-stimulatory signal region, i.e. so the CAR provides suboptimal activation upon binding to TAG-72 and requires a second CAR containing the missing domain to bind its respective antigen in order for the cell to be activated.

TABLE 1

First Generation CARs

| ScFv | Signal Domain |
|---|---|
| TAG-72 | CD8 |
| TAG-72 | CD3ζ |
| TAG-72 | CD3δ |
| TAG-72 | CD3γ |
| TAG-72 | CD3ε |
| TAG-72 | FcγRI-γ |
| TAG-72 | FcγRIII-γ |
| TAG-72 | FcεRIβ |
| TAG-72 | FcεRIγ |
| TAG-72 | DAP10 |
| TAG-72 | DAP12 |
| TAG-72 | CD32 |
| TAG-72 | CD79a |

TABLE 2

Second Generation CARs

| ScFv | Co-stimulatory Signal | Signal Domain | ScFv | Co-stimulatory Signal | Signal Domain |
|---|---|---|---|---|---|
| TAG-72 | CD28 | CD8 | TAG-72 | CD80 | FcεRIβ |
| TAG-72 | CD28 | CD3ζ | TAG-72 | CD80 | FcεRIγ |
| TAG-72 | CD28 | CD3δ | TAG-72 | CD80 | DAP10 |
| TAG-72 | CD28 | CD3γ | TAG-72 | CD80 | DAP12 |
| TAG-72 | CD28 | CD3ε | TAG-72 | CD80 | CD32 |
| TAG-72 | CD28 | FcγRI-γ | TAG-72 | CD80 | CD79a |
| TAG-72 | CD28 | FcγRIII-γ | TAG-72 | CD80 | CD79b |
| TAG-72 | CD28 | FcεRIβ | TAG-72 | CD86 | CD8 |
| TAG-72 | CD28 | FcεRIγ | TAG-72 | CD86 | CD3ζ |
| TAG-72 | CD28 | DAP10 | TAG-72 | CD86 | CD3δ |
| TAG-72 | CD28 | DAP12 | TAG-72 | CD86 | CD3γ |
| TAG-72 | CD28 | CD32 | TAG-72 | CD86 | CD3ε |
| TAG-72 | CD28 | CD79a | TAG-72 | CD86 | FcγRI-γ |
| TAG-72 | CD28 | CD79b | TAG-72 | CD86 | FcγRIII-γ |
| TAG-72 | CD8 | CD8 | TAG-72 | CD86 | FcεRIβ |
| TAG-72 | CD8 | CD3ζ | TAG-72 | CD86 | FcεRIγ |
| TAG-72 | CD8 | CD3δ | TAG-72 | CD86 | DAP10 |
| TAG-72 | CD8 | CD3γ | TAG-72 | CD86 | DAP12 |
| TAG-72 | CD8 | CD3ε | TAG-72 | CD86 | CD32 |
| TAG-72 | CD8 | FcγRI-γ | TAG-72 | CD86 | CD79a |
| TAG-72 | CD8 | FcγRIII-γ | TAG-72 | CD86 | CD79b |
| TAG-72 | CD8 | FcεRIβ | TAG-72 | OX40 | CD8 |
| TAG-72 | CD8 | FcεRIγ | TAG-72 | OX40 | CD3ζ |
| TAG-72 | CD8 | DAP10 | TAG-72 | OX40 | CD3δ |
| TAG-72 | CD8 | DAP12 | TAG-72 | OX40 | CD3γ |
| TAG-72 | CD8 | CD32 | TAG-72 | OX40 | CD3ε |
| TAG-72 | CD8 | CD79a | TAG-72 | OX40 | FcγRI-γ |
| TAG-72 | CD8 | CD79b | TAG-72 | OX40 | FcγRIII-γ |
| TAG-72 | CD4 | CD8 | TAG-72 | OX40 | FcεRIβ |
| TAG-72 | CD4 | CD3ζ | TAG-72 | OX40 | FcεRIγ |
| TAG-72 | CD4 | CD3δ | TAG-72 | OX40 | DAP10 |
| TAG-72 | CD4 | CD3γ | TAG-72 | OX40 | DAP12 |
| TAG-72 | CD4 | CD3ε | TAG-72 | OX40 | CD32 |
| TAG-72 | CD4 | FcγRI-γ | TAG-72 | OX40 | CD79a |
| TAG-72 | CD4 | FcγRIII-γ | TAG-72 | OX40 | CD79b |
| TAG-72 | CD4 | FcεRIβ | TAG-72 | DAP10 | CD8 |
| TAG-72 | CD4 | FcεRIγ | TAG-72 | DAP10 | CD3ζ |
| TAG-72 | CD4 | DAP10 | TAG-72 | DAP10 | CD3δ |
| TAG-72 | CD4 | DAP12 | TAG-72 | DAP10 | CD3γ |
| TAG-72 | CD4 | CD32 | TAG-72 | DAP10 | CD3ε |
| TAG-72 | CD4 | CD79a | TAG-72 | DAP10 | FcγRI-γ |
| TAG-72 | CD4 | CD79b | TAG-72 | DAP10 | FcγRIII-γ |
| TAG-72 | b2c | CD8 | TAG-72 | DAP10 | FcεRIβ |
| TAG-72 | b2c | CD3ζ | TAG-72 | DAP10 | FcεRIγ |
| TAG-72 | b2c | CD3δ | TAG-72 | DAP10 | DAP10 |
| TAG-72 | b2c | CD3γ | TAG-72 | DAP10 | DAP12 |
| TAG-72 | b2c | CD3ε | TAG-72 | DAP10 | CD32 |
| TAG-72 | b2c | FcγRI-γ | TAG-72 | DAP10 | CD79a |

TABLE 2-continued

Second Generation CARs

| ScFv | Co-stimulatory Signal | Signal Domain | ScFv | Co-stimulatory Signal | Signal Domain |
|---|---|---|---|---|---|
| TAG-72 | b2c | FcγRIII-γ | TAG-72 | DAP10 | CD79b |
| TAG-72 | b2c | FcεRIβ | TAG-72 | DAP12 | CD8 |
| TAG-72 | b2c | FcεRIγ | TAG-72 | DAP12 | CD3ζ |
| TAG-72 | b2c | DAP10 | TAG-72 | DAP12 | CD3δ |
| TAG-72 | b2c | DAP12 | TAG-72 | DAP12 | CD3γ |
| TAG-72 | b2c | CD32 | TAG-72 | DAP12 | CD3ε |
| TAG-72 | b2c | CD79a | TAG-72 | DAP12 | FcγRI-γ |
| TAG-72 | b2c | CD79b | TAG-72 | DAP12 | FcγRIII-γ |
| TAG-72 | CD137/41BB | CD8 | TAG-72 | DAP12 | FcεRIβ |
| TAG-72 | CD137/41BB | CD3ζ | TAG-72 | DAP12 | FcεRIγ |
| TAG-72 | CD137/41BB | CD3δ | TAG-72 | DAP12 | DAP10 |
| TAG-72 | CD137/41BB | CD3γ | TAG-72 | DAP12 | DAP12 |
| TAG-72 | CD137/41BB | CD3ε | TAG-72 | DAP12 | CD32 |
| TAG-72 | CD137/41BB | FcγRI-γ | TAG-72 | DAP12 | CD79a |
| TAG-72 | CD137/41BB | FcγRIII-γ | TAG-72 | DAP12 | CD79b |
| TAG-72 | CD137/41BB | FcεRIβ | TAG-72 | MyD88 | CD8 |
| TAG-72 | CD137/41BB | FcεRIγ | TAG-72 | MyD88 | CD3ζ |
| TAG-72 | CD137/41BB | DAP10 | TAG-72 | MyD88 | CD3δ |
| TAG-72 | CD137/41BB | DAP12 | TAG-72 | MyD88 | CD3γ |
| TAG-72 | CD137/41BB | CD32 | TAG-72 | MyD88 | CD3ε |
| TAG-72 | CD137/41BB | CD79a | TAG-72 | MyD88 | FcγRI-γ |
| TAG-72 | CD137/41BB | CD79b | TAG-72 | MyD88 | FcγRIII-γ |
| TAG-72 | ICOS | CD8 | TAG-72 | MyD88 | FcεRIβ |
| TAG-72 | ICOS | CD3ζ | TAG-72 | MyD88 | FcεRIγ |
| TAG-72 | ICOS | CD3δ | TAG-72 | MyD88 | DAP10 |
| TAG-72 | ICOS | CD3γ | TAG-72 | MyD88 | DAP12 |
| TAG-72 | ICOS | CD3ε | TAG-72 | MyD88 | CD32 |
| TAG-72 | ICOS | FcγRI-γ | TAG-72 | MyD88 | CD79a |
| TAG-72 | ICOS | FcγRIII-γ | TAG-72 | MyD88 | CD79b |
| TAG-72 | ICOS | FcεRIβ | TAG-72 | CD7 | CD8 |
| TAG-72 | ICOS | FcεRIγ | TAG-72 | CD7 | CD3ζ |
| TAG-72 | ICOS | DAP10 | TAG-72 | CD7 | CD3δ |
| TAG-72 | ICOS | DAP12 | TAG-72 | CD7 | CD3γ |
| TAG-72 | ICOS | CD32 | TAG-72 | CD7 | CD3ε |
| TAG-72 | ICOS | CD79a | TAG-72 | CD7 | FcγRI-γ |
| TAG-72 | ICOS | CD79b | TAG-72 | CD7 | FcγRIII-γ |
| TAG-72 | CD27 | CD8 | TAG-72 | CD7 | FcεRIβ |
| TAG-72 | CD27 | CD3ζ | TAG-72 | CD7 | FcεRIγ |
| TAG-72 | CD27 | CD3δ | TAG-72 | CD7 | DAP10 |
| TAG-72 | CD27 | CD3γ | TAG-72 | CD7 | DAP12 |
| TAG-72 | CD27 | CD3ε | TAG-72 | CD7 | CD32 |
| TAG-72 | CD27 | FcγRI-γ | TAG-72 | CD7 | CD79a |
| TAG-72 | CD27 | FcγRIII-γ | TAG-72 | CD7 | CD79b |
| TAG-72 | CD27 | FcεRIβ | TAG-72 | BTNL3 | CD8 |
| TAG-72 | CD27 | FcεRIγ | TAG-72 | BTNL3 | CD3ζ |
| TAG-72 | CD27 | DAP10 | TAG-72 | BTNL3 | CD3δ |
| TAG-72 | CD27 | DAP12 | TAG-72 | BTNL3 | CD3γ |
| TAG-72 | CD27 | CD32 | TAG-72 | BTNL3 | CD3ε |
| TAG-72 | CD27 | CD79a | TAG-72 | BTNL3 | FcγRI-γ |
| TAG-72 | CD27 | CD79b | TAG-72 | BTNL3 | FcγRIII-γ |
| TAG-72 | CD28δ | CD8 | TAG-72 | BTNL3 | FcεRIβ |
| TAG-72 | CD28δ | CD3ζ | TAG-72 | BTNL3 | FcεRIγ |
| TAG-72 | CD28δ | CD3δ | TAG-72 | BTNL3 | DAP10 |
| TAG-72 | CD28δ | CD3γ | TAG-72 | BTNL3 | DAP12 |
| TAG-72 | CD28δ | CD3ε | TAG-72 | BTNL3 | CD32 |
| TAG-72 | CD28δ | FcγRI-γ | TAG-72 | BTNL3 | CD79a |
| TAG-72 | CD28δ | FcγRIII-γ | TAG-72 | BTNL3 | CD79b |
| TAG-72 | CD28δ | FcεRIβ | TAG-72 | NKG2D | CD8 |
| TAG-72 | CD28δ | FcεRIγ | TAG-72 | NKG2D | CD3ζ |
| TAG-72 | CD28δ | DAP10 | TAG-72 | NKG2D | CD3δ |
| TAG-72 | CD28δ | DAP12 | TAG-72 | NKG2D | CD3γ |
| TAG-72 | CD28δ | CD32 | TAG-72 | NKG2D | CD3ε |
| TAG-72 | CD28δ | CD79a | TAG-72 | NKG2D | FcγRI-γ |
| TAG-72 | CD28δ | CD79b | TAG-72 | NKG2D | FcγRIII-γ |
| TAG-72 | CD80 | CD8 | TAG-72 | NKG2D | FcεRIβ |
| TAG-72 | CD80 | CD3ζ | TAG-72 | NKG2D | FcεRIγ |
| TAG-72 | CD80 | CD3δ | TAG-72 | NKG2D | DAP10 |
| TAG-72 | CD80 | CD3γ | TAG-72 | NKG2D | DAP12 |
| TAG-72 | CD80 | CD3ε | TAG-72 | NKG2D | CD32 |
| TAG-72 | CD80 | FcγRI-γ | TAG-72 | NKG2D | CD79a |
| TAG-72 | CD80 | FcγRIII-γ | TAG-72 | NKG2D | CD79b |

TABLE 3

| ScFv | Co-stimulatory Signal | Co-stimulatory Signal | Signal Domain |
|---|---|---|---|
| | Third Generation CARs | | |
| TAG-72 | CD28 | CD28 | CD8 |
| TAG-72 | CD28 | CD28 | CD3ζ |
| TAG-72 | CD28 | CD28 | CD3δ |
| TAG-72 | CD28 | CD28 | CD3γ |
| TAG-72 | CD28 | CD28 | CD3ε |
| TAG-72 | CD28 | CD28 | FcγRI-γ |
| TAG-72 | CD28 | CD28 | FcγRIII-γ |
| TAG-72 | CD28 | CD28 | FcεRIβ |
| TAG-72 | CD28 | CD28 | FcεRIγ |
| TAG-72 | CD28 | CD28 | DAP10 |
| TAG-72 | CD28 | CD28 | DAP12 |
| TAG-72 | CD28 | CD28 | CD32 |
| TAG-72 | CD28 | CD28 | CD79a |
| TAG-72 | CD28 | CD28 | CD79b |
| TAG-72 | CD28 | CD8 | CD8 |
| TAG-72 | CD28 | CD8 | CD3ζ |
| TAG-72 | CD28 | CD8 | CD3δ |
| TAG-72 | CD28 | CD8 | CD3γ |
| TAG-72 | CD28 | CD8 | CD3ε |
| TAG-72 | CD28 | CD8 | FcγRI-γ |
| TAG-72 | CD28 | CD8 | FcγRIII-γ |
| TAG-72 | CD28 | CD8 | FcεRIβ |
| TAG-72 | CD28 | CD8 | FcεRIγ |
| TAG-72 | CD28 | CD8 | DAP10 |
| TAG-72 | CD28 | CD8 | DAP12 |
| TAG-72 | CD28 | CD8 | CD32 |
| TAG-72 | CD28 | CD8 | CD79a |
| TAG-72 | CD28 | CD8 | CD79b |
| TAG-72 | CD28 | CD4 | CD8 |
| TAG-72 | CD28 | CD4 | CD3ζ |
| TAG-72 | CD28 | CD4 | CD3δ |
| TAG-72 | CD28 | CD4 | CD3γ |
| TAG-72 | CD28 | CD4 | CD3ε |
| TAG-72 | CD28 | CD4 | FcγRI-γ |
| TAG-72 | CD28 | CD4 | FcγRIII-γ |
| TAG-72 | CD28 | CD4 | FcεRIβ |
| TAG-72 | CD28 | CD4 | FcεRIγ |
| TAG-72 | CD28 | CD4 | DAP10 |
| TAG-72 | CD28 | CD4 | DAP12 |
| TAG-72 | CD28 | CD4 | CD32 |
| TAG-72 | CD28 | CD4 | CD79a |
| TAG-72 | CD28 | CD4 | CD79b |
| TAG-72 | CD28 | b2c | CD8 |
| TAG-72 | CD28 | b2c | CD3ζ |
| TAG-72 | CD28 | b2c | CD3δ |
| TAG-72 | CD28 | b2c | CD3γ |
| TAG-72 | CD28 | b2c | CD3ε |
| TAG-72 | CD28 | b2c | FcγRI-γ |
| TAG-72 | CD28 | b2c | FcγRIII-γ |
| TAG-72 | CD28 | b2c | FcεRIβ |
| TAG-72 | CD28 | b2c | FcεRIγ |
| TAG-72 | CD28 | b2c | DAP10 |
| TAG-72 | CD28 | b2c | DAP12 |
| TAG-72 | CD28 | b2c | CD32 |
| TAG-72 | CD28 | b2c | CD79a |
| TAG-72 | CD28 | b2c | CD79b |
| TAG-72 | CD28 | CD137/41BB | CD8 |
| TAG-72 | CD28 | CD137/41BB | CD3ζ |
| TAG-72 | CD28 | CD137/41BB | CD3δ |
| TAG-72 | CD28 | CD137/41BB | CD3γ |
| TAG-72 | CD28 | CD137/41BB | CD3ε |
| TAG-72 | CD28 | CD137/41BB | FcγRI-γ |
| TAG-72 | CD28 | CD137/41BB | FcγRIII-γ |
| TAG-72 | CD28 | CD137/41BB | FcεRIβ |
| TAG-72 | CD28 | CD137/41BB | FcεRIγ |
| TAG-72 | CD28 | CD137/41BB | DAP10 |
| TAG-72 | CD28 | CD137/41BB | DAP12 |
| TAG-72 | CD28 | CD137/41BB | CD32 |
| TAG-72 | CD28 | CD137/41BB | CD79a |
| TAG-72 | CD28 | CD137/41BB | CD79b |
| TAG-72 | CD28 | ICOS | CD8 |
| TAG-72 | CD28 | ICOS | CD3ζ |
| TAG-72 | CD28 | ICOS | CD3δ |
| TAG-72 | CD28 | ICOS | CD3γ |
| TAG-72 | CD28 | ICOS | CD3ε |
| TAG-72 | CD28 | ICOS | FcγRI-γ |
| TAG-72 | CD28 | ICOS | FcγRIII-γ |
| TAG-72 | CD28 | ICOS | FcεRIβ |
| TAG-72 | CD28 | ICOS | FcεRIγ |
| TAG-72 | CD28 | ICOS | DAP10 |
| TAG-72 | CD28 | ICOS | DAP12 |
| TAG-72 | CD28 | ICOS | CD32 |
| TAG-72 | CD28 | ICOS | CD79a |
| TAG-72 | CD28 | ICOS | CD79b |
| TAG-72 | CD28 | CD27 | CD8 |
| TAG-72 | CD28 | CD27 | CD3ζ |
| TAG-72 | CD28 | CD27 | CD3δ |
| TAG-72 | CD28 | CD27 | CD3γ |
| TAG-72 | CD28 | CD27 | CD3ε |
| TAG-72 | CD28 | CD27 | FcγRI-γ |
| TAG-72 | CD28 | CD27 | FcγRIII-γ |
| TAG-72 | CD28 | CD27 | FcεRIβ |
| TAG-72 | CD28 | CD27 | FcεRIγ |
| TAG-72 | CD28 | CD27 | DAP10 |
| TAG-72 | CD28 | CD27 | DAP12 |
| TAG-72 | CD28 | CD27 | CD32 |
| TAG-72 | CD28 | CD27 | CD79a |
| TAG-72 | CD28 | CD27 | CD79b |
| TAG-72 | CD28 | CD28δ | CD8 |
| TAG-72 | CD28 | CD28δ | CD3ζ |
| TAG-72 | CD28 | CD28δ | CD3δ |
| TAG-72 | CD28 | CD28δ | CD3γ |
| TAG-72 | CD28 | CD28δ | CD3ε |
| TAG-72 | CD28 | CD28δ | FcγRI-γ |
| TAG-72 | CD28 | CD28δ | FcγRIII-γ |
| TAG-72 | CD28 | CD28δ | FcεRIβ |
| TAG-72 | CD28 | CD28δ | FcεRIγ |
| TAG-72 | CD28 | CD28δ | DAP10 |
| TAG-72 | CD28 | CD28δ | DAP12 |
| TAG-72 | CD28 | CD28δ | CD32 |
| TAG-72 | CD28 | CD28δ | CD79a |
| TAG-72 | CD28 | CD28δ | CD79b |
| TAG-72 | CD28 | CD80 | CD8 |
| TAG-72 | CD28 | CD80 | CD3ζ |
| TAG-72 | CD28 | CD80 | CD3δ |
| TAG-72 | CD28 | CD80 | CD3γ |
| TAG-72 | CD28 | CD80 | CD3ε |
| TAG-72 | CD28 | CD80 | FcγRI-γ |
| TAG-72 | CD28 | CD80 | FcγRIII-γ |
| TAG-72 | CD28 | CD80 | FcεRIβ |
| TAG-72 | CD28 | CD80 | FcεRIγ |
| TAG-72 | CD28 | CD80 | DAP10 |
| TAG-72 | CD28 | CD80 | DAP12 |
| TAG-72 | CD28 | CD80 | CD32 |
| TAG-72 | CD28 | CD80 | CD79a |
| TAG-72 | CD28 | CD80 | CD79b |
| TAG-72 | CD28 | CD86 | CD8 |
| TAG-72 | CD28 | CD86 | CD3ζ |
| TAG-72 | CD28 | CD86 | CD3δ |
| TAG-72 | CD28 | CD86 | CD3γ |
| TAG-72 | CD28 | CD86 | CD3ε |
| TAG-72 | CD28 | CD86 | FcγRI-γ |
| TAG-72 | CD28 | CD86 | FcγRIII-γ |
| TAG-72 | CD28 | CD86 | FcεRIβ |
| TAG-72 | CD28 | CD86 | FcεRIγ |
| TAG-72 | CD28 | CD86 | DAP10 |
| TAG-72 | CD28 | CD86 | DAP12 |
| TAG-72 | CD28 | CD86 | CD32 |
| TAG-72 | CD28 | CD86 | CD79a |
| TAG-72 | CD28 | CD86 | CD79b |
| TAG-72 | CD28 | OX40 | CD8 |
| TAG-72 | CD28 | OX40 | CD3ζ |
| TAG-72 | CD28 | OX40 | CD3δ |
| TAG-72 | CD28 | OX40 | CD3γ |
| TAG-72 | CD28 | OX40 | CD3ε |
| TAG-72 | CD28 | OX40 | FcγRI-γ |
| TAG-72 | CD28 | OX40 | FcγRIII-γ |
| TAG-72 | CD28 | OX40 | FcεRIβ |
| TAG-72 | CD28 | OX40 | FcεRIγ |
| TAG-72 | CD28 | OX40 | DAP10 |

TABLE 3-continued

Third Generation CARs

| ScFv | Co-stimulatory Signal | Co-stimulatory Signal | Signal Domain |
|---|---|---|---|
| TAG-72 | CD28 | OX40 | DAP12 |
| TAG-72 | CD28 | OX40 | CD32 |
| TAG-72 | CD28 | OX40 | CD79a |
| TAG-72 | CD28 | OX40 | CD79b |
| TAG-72 | CD28 | DAP10 | CD8 |
| TAG-72 | CD28 | DAP10 | CD3ζ |
| TAG-72 | CD28 | DAP10 | CD3δ |
| TAG-72 | CD28 | DAP10 | CD3γ |
| TAG-72 | CD28 | DAP10 | CD3ε |
| TAG-72 | CD28 | DAP10 | FcγRI-γ |
| TAG-72 | CD28 | DAP10 | FcγRIII-γ |
| TAG-72 | CD28 | DAP10 | FcεRIβ |
| TAG-72 | CD28 | DAP10 | FcεRIγ |
| TAG-72 | CD28 | DAP10 | DAP10 |
| TAG-72 | CD28 | DAP10 | DAP12 |
| TAG-72 | CD28 | DAP10 | CD32 |
| TAG-72 | CD28 | DAP10 | CD79a |
| TAG-72 | CD28 | DAP10 | CD79b |
| TAG-72 | CD28 | DAP12 | CD8 |
| TAG-72 | CD28 | DAP12 | CD3ζ |
| TAG-72 | CD28 | DAP12 | CD3δ |
| TAG-72 | CD28 | DAP12 | CD3γ |
| TAG-72 | CD28 | DAP12 | CD3ε |
| TAG-72 | CD28 | DAP12 | FcγRI-γ |
| TAG-72 | CD28 | DAP12 | FcγRIII-γ |
| TAG-72 | CD28 | DAP12 | FcεRIβ |
| TAG-72 | CD28 | DAP12 | FcεRIγ |
| TAG-72 | CD28 | DAP12 | DAP10 |
| TAG-72 | CD28 | DAP12 | DAP12 |
| TAG-72 | CD28 | DAP12 | CD32 |
| TAG-72 | CD28 | DAP12 | CD79a |
| TAG-72 | CD28 | DAP12 | CD79b |
| TAG-72 | CD28 | MyD88 | CD8 |
| TAG-72 | CD28 | MyD88 | CD3ζ |
| TAG-72 | CD28 | MyD88 | CD3δ |
| TAG-72 | CD28 | MyD88 | CD3γ |
| TAG-72 | CD28 | MyD88 | CD3ε |
| TAG-72 | CD28 | MyD88 | FcγRI-γ |
| TAG-72 | CD28 | MyD88 | FcγRIII-γ |
| TAG-72 | CD28 | MyD88 | FcεRIβ |
| TAG-72 | CD28 | MyD88 | FcεRIγ |
| TAG-72 | CD28 | MyD88 | DAP10 |
| TAG-72 | CD28 | MyD88 | DAP12 |
| TAG-72 | CD28 | MyD88 | CD32 |
| TAG-72 | CD28 | MyD88 | CD79a |
| TAG-72 | CD28 | MyD88 | CD79b |
| TAG-72 | CD28 | CD7 | CD8 |
| TAG-72 | CD28 | CD7 | CD3ζ |
| TAG-72 | CD28 | CD7 | CD3δ |
| TAG-72 | CD28 | CD7 | CD3γ |
| TAG-72 | CD28 | CD7 | CD3ε |
| TAG-72 | CD28 | CD7 | FcγRI-γ |
| TAG-72 | CD28 | CD7 | FcγRIII-γ |
| TAG-72 | CD28 | CD7 | FcεRIβ |
| TAG-72 | CD28 | CD7 | FcεRIγ |
| TAG-72 | CD28 | CD7 | DAP10 |
| TAG-72 | CD28 | CD7 | DAP12 |
| TAG-72 | CD28 | CD7 | CD32 |
| TAG-72 | CD28 | CD7 | CD79a |
| TAG-72 | CD28 | CD7 | CD79b |
| TAG-72 | CD28 | BTNL3 | CD8 |
| TAG-72 | CD28 | BTNL3 | CD3ζ |
| TAG-72 | CD28 | BTNL3 | CD3δ |
| TAG-72 | CD28 | BTNL3 | CD3γ |
| TAG-72 | CD28 | BTNL3 | CD3ε |
| TAG-72 | CD28 | BTNL3 | FcγRI-γ |
| TAG-72 | CD28 | BTNL3 | FcγRIII-γ |
| TAG-72 | CD28 | BTNL3 | FcεRIβ |
| TAG-72 | CD28 | BTNL3 | FcεRIγ |
| TAG-72 | CD28 | BTNL3 | DAP10 |
| TAG-72 | CD28 | BTNL3 | DAP12 |
| TAG-72 | CD28 | BTNL3 | CD32 |
| TAG-72 | CD28 | BTNL3 | CD79a |
| TAG-72 | CD28 | BTNL3 | CD79b |
| TAG-72 | CD28 | NKG2D | CD8 |
| TAG-72 | CD28 | NKG2D | CD3ζ |
| TAG-72 | CD28 | NKG2D | CD3δ |
| TAG-72 | CD28 | NKG2D | CD3γ |
| TAG-72 | CD28 | NKG2D | CD3ε |
| TAG-72 | CD28 | NKG2D | FcγRI-γ |
| TAG-72 | CD28 | NKG2D | FcγRIII-γ |
| TAG-72 | CD28 | NKG2D | FcεRIβ |
| TAG-72 | CD28 | NKG2D | FcεRIγ |
| TAG-72 | CD28 | NKG2D | DAP10 |
| TAG-72 | CD28 | NKG2D | DAP12 |
| TAG-72 | CD28 | NKG2D | CD32 |
| TAG-72 | CD28 | NKG2D | CD79a |
| TAG-72 | CD28 | NKG2D | CD79b |
| TAG-72 | CD8 | CD28 | CD8 |
| TAG-72 | CD8 | CD28 | CD3ζ |
| TAG-72 | CD8 | CD28 | CD3δ |
| TAG-72 | CD8 | CD28 | CD3γ |
| TAG-72 | CD8 | CD28 | CD3ε |
| TAG-72 | CD8 | CD28 | FcγRI-γ |
| TAG-72 | CD8 | CD28 | FcγRIII-γ |
| TAG-72 | CD8 | CD28 | FcεRIβ |
| TAG-72 | CD8 | CD28 | FcεRIγ |
| TAG-72 | CD8 | CD28 | DAP10 |
| TAG-72 | CD8 | CD28 | DAP12 |
| TAG-72 | CD8 | CD28 | CD32 |
| TAG-72 | CD8 | CD28 | CD79a |
| TAG-72 | CD8 | CD28 | CD79b |
| TAG-72 | CD8 | CD8 | CD8 |
| TAG-72 | CD8 | CD8 | CD3ζ |
| TAG-72 | CD8 | CD8 | CD3δ |
| TAG-72 | CD8 | CD8 | CD3γ |
| TAG-72 | CD8 | CD8 | CD3ε |
| TAG-72 | CD8 | CD8 | FcγRI-γ |
| TAG-72 | CD8 | CD8 | FcγRIII-γ |
| TAG-72 | CD8 | CD8 | FcεRIβ |
| TAG-72 | CD8 | CD8 | FcεRIγ |
| TAG-72 | CD8 | CD8 | DAP10 |
| TAG-72 | CD8 | CD8 | DAP12 |
| TAG-72 | CD8 | CD8 | CD32 |
| TAG-72 | CD8 | CD8 | CD79a |
| TAG-72 | CD8 | CD8 | CD79b |
| TAG-72 | CD8 | CD4 | CD8 |
| TAG-72 | CD8 | CD4 | CD3ζ |
| TAG-72 | CD8 | CD4 | CD3δ |
| TAG-72 | CD8 | CD4 | CD3γ |
| TAG-72 | CD8 | CD4 | CD3ε |
| TAG-72 | CD8 | CD4 | FcγRI-γ |
| TAG-72 | CD8 | CD4 | FcγRIII-γ |
| TAG-72 | CD8 | CD4 | FcεRIβ |
| TAG-72 | CD8 | CD4 | FcεRIγ |
| TAG-72 | CD8 | CD4 | DAP10 |
| TAG-72 | CD8 | CD4 | DAP12 |
| TAG-72 | CD8 | CD4 | CD32 |
| TAG-72 | CD8 | CD4 | CD79a |
| TAG-72 | CD8 | CD4 | CD79b |
| TAG-72 | CD8 | b2c | CD8 |
| TAG-72 | CD8 | b2c | CD3ζ |
| TAG-72 | CD8 | b2c | CD3δ |
| TAG-72 | CD8 | b2c | CD3γ |
| TAG-72 | CD8 | b2c | CD3ε |
| TAG-72 | CD8 | b2c | FcγRI-γ |
| TAG-72 | CD8 | b2c | FcγRIII-γ |
| TAG-72 | CD8 | b2c | FcεRIβ |
| TAG-72 | CD8 | b2c | FcεRIγ |
| TAG-72 | CD8 | b2c | DAP10 |
| TAG-72 | CD8 | b2c | DAP12 |
| TAG-72 | CD8 | b2c | CD32 |
| TAG-72 | CD8 | b2c | CD79a |
| TAG-72 | CD8 | b2c | CD79b |
| TAG-72 | CD8 | CD137/41BB | CD8 |
| TAG-72 | CD8 | CD137/41BB | CD3ζ |
| TAG-72 | CD8 | CD137/41BB | CD3δ |
| TAG-72 | CD8 | CD137/41BB | CD3γ |
| TAG-72 | CD8 | CD137/41BB | CD3ε |
| TAG-72 | CD8 | CD137/41BB | FcγRI-γ |

TABLE 3-continued

Third Generation CARs

| ScFv | Co-stimulatory Signal | Co-stimulatory Signal | Signal Domain |
|---|---|---|---|
| TAG-72 | CD8 | CD137/41BB | FcγRIII-γ |
| TAG-72 | CD8 | CD137/41BB | FcεRIβ |
| TAG-72 | CD8 | CD137/41BB | FcεRIγ |
| TAG-72 | CD8 | CD137/41BB | DAP10 |
| TAG-72 | CD8 | CD137/41BB | DAP12 |
| TAG-72 | CD8 | CD137/41BB | CD32 |
| TAG-72 | CD8 | CD137/41BB | CD79a |
| TAG-72 | CD8 | CD137/41BB | CD79b |
| TAG-72 | CD8 | ICOS | CD8 |
| TAG-72 | CD8 | ICOS | CD3ζ |
| TAG-72 | CD8 | ICOS | CD3δ |
| TAG-72 | CD8 | ICOS | CD3γ |
| TAG-72 | CD8 | ICOS | CD3ε |
| TAG-72 | CD8 | ICOS | FcγRI-γ |
| TAG-72 | CD8 | ICOS | FcγRIII-γ |
| TAG-72 | CD8 | ICOS | FcεRIβ |
| TAG-72 | CD8 | ICOS | FcεRIγ |
| TAG-72 | CD8 | ICOS | DAP10 |
| TAG-72 | CD8 | ICOS | DAP12 |
| TAG-72 | CD8 | ICOS | CD32 |
| TAG-72 | CD8 | ICOS | CD79a |
| TAG-72 | CD8 | ICOS | CD79b |
| TAG-72 | CD8 | CD27 | CD8 |
| TAG-72 | CD8 | CD27 | CD3ζ |
| TAG-72 | CD8 | CD27 | CD3δ |
| TAG-72 | CD8 | CD27 | CD3γ |
| TAG-72 | CD8 | CD27 | CD3ε |
| TAG-72 | CD8 | CD27 | FcγRI-γ |
| TAG-72 | CD8 | CD27 | FcγRIII-γ |
| TAG-72 | CD8 | CD27 | FcεRIβ |
| TAG-72 | CD8 | CD27 | FcεRIγ |
| TAG-72 | CD8 | CD27 | DAP10 |
| TAG-72 | CD8 | CD27 | DAP12 |
| TAG-72 | CD8 | CD27 | CD32 |
| TAG-72 | CD8 | CD27 | CD79a |
| TAG-72 | CD8 | CD27 | CD79b |
| TAG-72 | CD8 | CD28δ | CD8 |
| TAG-72 | CD8 | CD28δ | CD3ζ |
| TAG-72 | CD8 | CD28δ | CD3δ |
| TAG-72 | CD8 | CD28δ | CD3γ |
| TAG-72 | CD8 | CD28δ | CD3ε |
| TAG-72 | CD8 | CD28δ | FcγRI-γ |
| TAG-72 | CD8 | CD28δ | FcγRIII-γ |
| TAG-72 | CD8 | CD28δ | FcεRIβ |
| TAG-72 | CD8 | CD28δ | FcεRIγ |
| TAG-72 | CD8 | CD28δ | DAP10 |
| TAG-72 | CD8 | CD28δ | DAP12 |
| TAG-72 | CD8 | CD28δ | CD32 |
| TAG-72 | CD8 | CD28δ | CD79a |
| TAG-72 | CD8 | CD28δ | CD79b |
| TAG-72 | CD8 | CD80 | CD8 |
| TAG-72 | CD8 | CD80 | CD3ζ |
| TAG-72 | CD8 | CD80 | CD3δ |
| TAG-72 | CD8 | CD80 | CD3γ |
| TAG-72 | CD8 | CD80 | CD3ε |
| TAG-72 | CD8 | CD80 | FcγRI-γ |
| TAG-72 | CD8 | CD80 | FcγRIII-γ |
| TAG-72 | CD8 | CD80 | FcεRIβ |
| TAG-72 | CD8 | CD80 | FcεRIγ |
| TAG-72 | CD8 | CD80 | DAP10 |
| TAG-72 | CD8 | CD80 | DAP12 |
| TAG-72 | CD8 | CD80 | CD32 |
| TAG-72 | CD8 | CD80 | CD79a |
| TAG-72 | CD8 | CD80 | CD79b |
| TAG-72 | CD8 | CD86 | CD8 |
| TAG-72 | CD8 | CD86 | CD3ζ |
| TAG-72 | CD8 | CD86 | CD3δ |
| TAG-72 | CD8 | CD86 | CD3γ |
| TAG-72 | CD8 | CD86 | CD3ε |
| TAG-72 | CD8 | CD86 | FcγRI-γ |
| TAG-72 | CD8 | CD86 | FcγRIII-γ |
| TAG-72 | CD8 | CD86 | FcεRIβ |
| TAG-72 | CD8 | CD86 | FcεRIγ |
| TAG-72 | CD8 | CD86 | DAP10 |
| TAG-72 | CD8 | CD86 | DAP12 |
| TAG-72 | CD8 | CD86 | CD32 |
| TAG-72 | CD8 | CD86 | CD79a |
| TAG-72 | CD8 | CD86 | CD79b |
| TAG-72 | CD8 | OX40 | CD8 |
| TAG-72 | CD8 | OX40 | CD3ζ |
| TAG-72 | CD8 | OX40 | CD3δ |
| TAG-72 | CD8 | OX40 | CD3γ |
| TAG-72 | CD8 | OX40 | CD3ε |
| TAG-72 | CD8 | OX40 | FcγRI-γ |
| TAG-72 | CD8 | OX40 | FcγRIII-γ |
| TAG-72 | CD8 | OX40 | FcεRIβ |
| TAG-72 | CD8 | OX40 | FcεRIγ |
| TAG-72 | CD8 | OX40 | DAP10 |
| TAG-72 | CD8 | OX40 | DAP12 |
| TAG-72 | CD8 | OX40 | CD32 |
| TAG-72 | CD8 | OX40 | CD79a |
| TAG-72 | CD8 | OX40 | CD79b |
| TAG-72 | CD8 | DAP10 | CD8 |
| TAG-72 | CD8 | DAP10 | CD3ζ |
| TAG-72 | CD8 | DAP10 | CD3δ |
| TAG-72 | CD8 | DAP10 | CD3γ |
| TAG-72 | CD8 | DAP10 | CD3ε |
| TAG-72 | CD8 | DAP10 | FcγRI-γ |
| TAG-72 | CD8 | DAP10 | FcγRIII-γ |
| TAG-72 | CD8 | DAP10 | FcεRIβ |
| TAG-72 | CD8 | DAP10 | FcεRIγ |
| TAG-72 | CD8 | DAP10 | DAP10 |
| TAG-72 | CD8 | DAP10 | DAP12 |
| TAG-72 | CD8 | DAP10 | CD32 |
| TAG-72 | CD8 | DAP10 | CD79a |
| TAG-72 | CD8 | DAP10 | CD79b |
| TAG-72 | CD8 | DAP12 | CD8 |
| TAG-72 | CD8 | DAP12 | CD3ζ |
| TAG-72 | CD8 | DAP12 | CD3δ |
| TAG-72 | CD8 | DAP12 | CD3γ |
| TAG-72 | CD8 | DAP12 | CD3ε |
| TAG-72 | CD8 | DAP12 | FcγRI-γ |
| TAG-72 | CD8 | DAP12 | FcγRIII-γ |
| TAG-72 | CD8 | DAP12 | FcεRIβ |
| TAG-72 | CD8 | DAP12 | FcεRIγ |
| TAG-72 | CD8 | DAP12 | DAP10 |
| TAG-72 | CD8 | DAP12 | DAP12 |
| TAG-72 | CD8 | DAP12 | CD32 |
| TAG-72 | CD8 | DAP12 | CD79a |
| TAG-72 | CD8 | DAP12 | CD79b |
| TAG-72 | CD8 | MyD88 | CD8 |
| TAG-72 | CD8 | MyD88 | CD3ζ |
| TAG-72 | CD8 | MyD88 | CD3δ |
| TAG-72 | CD8 | MyD88 | CD3γ |
| TAG-72 | CD8 | MyD88 | CD3ε |
| TAG-72 | CD8 | MyD88 | FcγRI-γ |
| TAG-72 | CD8 | MyD88 | FcγRIII-γ |
| TAG-72 | CD8 | MyD88 | FcεRIβ |
| TAG-72 | CD8 | MyD88 | FcεRIγ |
| TAG-72 | CD8 | MyD88 | DAP10 |
| TAG-72 | CD8 | MyD88 | DAP12 |
| TAG-72 | CD8 | MyD88 | CD32 |
| TAG-72 | CD8 | MyD88 | CD79a |
| TAG-72 | CD8 | MyD88 | CD79b |
| TAG-72 | CD8 | CD7 | CD8 |
| TAG-72 | CD8 | CD7 | CD3ζ |
| TAG-72 | CD8 | CD7 | CD3δ |
| TAG-72 | CD8 | CD7 | CD3γ |
| TAG-72 | CD8 | CD7 | CD3ε |
| TAG-72 | CD8 | CD7 | FcγRI-γ |
| TAG-72 | CD8 | CD7 | FcγRIII-γ |
| TAG-72 | CD8 | CD7 | FcεRIβ |
| TAG-72 | CD8 | CD7 | FcεRIγ |
| TAG-72 | CD8 | CD7 | DAP10 |
| TAG-72 | CD8 | CD7 | DAP12 |
| TAG-72 | CD8 | CD7 | CD32 |
| TAG-72 | CD8 | CD7 | CD79a |
| TAG-72 | CD8 | CD7 | CD79b |
| TAG-72 | CD8 | BTNL3 | CD8 |
| TAG-72 | CD8 | BTNL3 | CD3ζ |

TABLE 3-continued

| Third Generation CARs | | | |
|---|---|---|---|
| ScFv | Co-stimulatory Signal | Co-stimulatory Signal | Signal Domain |
| TAG-72 | CD8 | BTNL3 | CD3δ |
| TAG-72 | CD8 | BTNL3 | CD3γ |
| TAG-72 | CD8 | BTNL3 | CD3ε |
| TAG-72 | CD8 | BTNL3 | FcγRI-γ |
| TAG-72 | CD8 | BTNL3 | FcγRIII-γ |
| TAG-72 | CD8 | BTNL3 | FcεRIβ |
| TAG-72 | CD8 | BTNL3 | FcεRIγ |
| TAG-72 | CD8 | BTNL3 | DAP10 |
| TAG-72 | CD8 | BTNL3 | DAP12 |
| TAG-72 | CD8 | BTNL3 | CD32 |
| TAG-72 | CD8 | BTNL3 | CD79a |
| TAG-72 | CD8 | BTNL3 | CD79b |
| TAG-72 | CD8 | NKG2D | CD8 |
| TAG-72 | CD8 | NKG2D | CD3ζ |
| TAG-72 | CD8 | NKG2D | CD3δ |
| TAG-72 | CD8 | NKG2D | CD3γ |
| TAG-72 | CD8 | NKG2D | CD3ε |
| TAG-72 | CD8 | NKG2D | FcγRI-γ |
| TAG-72 | CD8 | NKG2D | FcγRIII-γ |
| TAG-72 | CD8 | NKG2D | FcεRIβ |
| TAG-72 | CD8 | NKG2D | FcεRIγ |
| TAG-72 | CD8 | NKG2D | DAP10 |
| TAG-72 | CD8 | NKG2D | DAP12 |
| TAG-72 | CD8 | NKG2D | CD32 |
| TAG-72 | CD8 | NKG2D | CD79a |
| TAG-72 | CD8 | NKG2D | CD79b |
| TAG-72 | CD4 | CD28 | CD8 |
| TAG-72 | CD4 | CD28 | CD3ζ |
| TAG-72 | CD4 | CD28 | CD3δ |
| TAG-72 | CD4 | CD28 | CD3γ |
| TAG-72 | CD4 | CD28 | CD3ε |
| TAG-72 | CD4 | CD28 | FcγRI-γ |
| TAG-72 | CD4 | CD28 | FcγRIII-γ |
| TAG-72 | CD4 | CD28 | FcεRIβ |
| TAG-72 | CD4 | CD28 | FcεRIγ |
| TAG-72 | CD4 | CD28 | DAP10 |
| TAG-72 | CD4 | CD28 | DAP12 |
| TAG-72 | CD4 | CD28 | CD32 |
| TAG-72 | CD4 | CD28 | CD79a |
| TAG-72 | CD4 | CD28 | CD79b |
| TAG-72 | CD4 | CD8 | CD8 |
| TAG-72 | CD4 | CD8 | CD3ζ |
| TAG-72 | CD4 | CD8 | CD3δ |
| TAG-72 | CD4 | CD8 | CD3γ |
| TAG-72 | CD4 | CD8 | CD3ε |
| TAG-72 | CD4 | CD8 | FcγRI-γ |
| TAG-72 | CD4 | CD8 | FcγRIII-γ |
| TAG-72 | CD4 | CD8 | FcεRIβ |
| TAG-72 | CD4 | CD8 | FcεRIγ |
| TAG-72 | CD4 | CD8 | DAP10 |
| TAG-72 | CD4 | CD8 | DAP12 |
| TAG-72 | CD4 | CD8 | CD32 |
| TAG-72 | CD4 | CD8 | CD79a |
| TAG-72 | CD4 | CD8 | CD79b |
| TAG-72 | CD4 | CD4 | CD8 |
| TAG-72 | CD4 | CD4 | CD3ζ |
| TAG-72 | CD4 | CD4 | CD3δ |
| TAG-72 | CD4 | CD4 | CD3γ |
| TAG-72 | CD4 | CD4 | CD3ε |
| TAG-72 | CD4 | CD4 | FcγRI-γ |
| TAG-72 | CD4 | CD4 | FcγRIII-γ |
| TAG-72 | CD4 | CD4 | FcεRIβ |
| TAG-72 | CD4 | CD4 | FcεRIγ |
| TAG-72 | CD4 | CD4 | DAP10 |
| TAG-72 | CD4 | CD4 | DAP12 |
| TAG-72 | CD4 | CD4 | CD32 |
| TAG-72 | CD4 | CD4 | CD79a |
| TAG-72 | CD4 | CD4 | CD79b |
| TAG-72 | CD4 | b2c | CD8 |
| TAG-72 | CD4 | b2c | CD3ζ |
| TAG-72 | CD4 | b2c | CD3δ |
| TAG-72 | CD4 | b2c | CD3γ |
| TAG-72 | CD4 | b2c | CD3ε |
| TAG-72 | CD4 | b2c | FcγRI-γ |
| TAG-72 | CD4 | b2c | FcγRIII-γ |
| TAG-72 | CD4 | b2c | FcεRIβ |
| TAG-72 | CD4 | b2c | FcεRIγ |
| TAG-72 | CD4 | b2c | DAP10 |
| TAG-72 | CD4 | b2c | DAP12 |
| TAG-72 | CD4 | b2c | CD32 |
| TAG-72 | CD4 | b2c | CD79a |
| TAG-72 | CD4 | b2c | CD79b |
| TAG-72 | CD4 | CD137/41BB | CD8 |
| TAG-72 | CD4 | CD137/41BB | CD3ζ |
| TAG-72 | CD4 | CD137/41BB | CD3δ |
| TAG-72 | CD4 | CD137/41BB | CD3γ |
| TAG-72 | CD4 | CD137/41BB | CD3ε |
| TAG-72 | CD4 | CD137/41BB | FcγRI-γ |
| TAG-72 | CD4 | CD137/41BB | FcγRIII-γ |
| TAG-72 | CD4 | CD137/41BB | FcεRIβ |
| TAG-72 | CD4 | CD137/41BB | FcεRIγ |
| TAG-72 | CD4 | CD137/41BB | DAP10 |
| TAG-72 | CD4 | CD137/41BB | DAP12 |
| TAG-72 | CD4 | CD137/41BB | CD32 |
| TAG-72 | CD4 | CD137/41BB | CD79a |
| TAG-72 | CD4 | CD137/41BB | CD79b |
| TAG-72 | CD4 | ICOS | CD8 |
| TAG-72 | CD4 | ICOS | CD3ζ |
| TAG-72 | CD4 | ICOS | CD3δ |
| TAG-72 | CD4 | ICOS | CD3γ |
| TAG-72 | CD4 | ICOS | CD3ε |
| TAG-72 | CD4 | ICOS | FcγRI-γ |
| TAG-72 | CD4 | ICOS | FcγRIII-γ |
| TAG-72 | CD4 | ICOS | FcεRIβ |
| TAG-72 | CD4 | ICOS | FcεRIγ |
| TAG-72 | CD4 | ICOS | DAP10 |
| TAG-72 | CD4 | ICOS | DAP12 |
| TAG-72 | CD4 | ICOS | CD32 |
| TAG-72 | CD4 | ICOS | CD79a |
| TAG-72 | CD4 | ICOS | CD79b |
| TAG-72 | CD4 | CD27 | CD8 |
| TAG-72 | CD4 | CD27 | CD3ζ |
| TAG-72 | CD4 | CD27 | CD3δ |
| TAG-72 | CD4 | CD27 | CD3γ |
| TAG-72 | CD4 | CD27 | CD3ε |
| TAG-72 | CD4 | CD27 | FcγRI-γ |
| TAG-72 | CD4 | CD27 | FcγRIII-γ |
| TAG-72 | CD4 | CD27 | FcεRIβ |
| TAG-72 | CD4 | CD27 | FcεRIγ |
| TAG-72 | CD4 | CD27 | DAP10 |
| TAG-72 | CD4 | CD27 | DAP12 |
| TAG-72 | CD4 | CD27 | CD32 |
| TAG-72 | CD4 | CD27 | CD79a |
| TAG-72 | CD4 | CD27 | CD79b |
| TAG-72 | CD4 | CD28δ | CD8 |
| TAG-72 | CD4 | CD28δ | CD3ζ |
| TAG-72 | CD4 | CD28δ | CD3δ |
| TAG-72 | CD4 | CD28δ | CD3γ |
| TAG-72 | CD4 | CD28δ | CD3ε |
| TAG-72 | CD4 | CD28δ | FcγRI-γ |
| TAG-72 | CD4 | CD28δ | FcγRIII-γ |
| TAG-72 | CD4 | CD28δ | FcεRIβ |
| TAG-72 | CD4 | CD28δ | FcεRIγ |
| TAG-72 | CD4 | CD28δ | DAP10 |
| TAG-72 | CD4 | CD28δ | DAP12 |
| TAG-72 | CD4 | CD28δ | CD32 |
| TAG-72 | CD4 | CD28δ | CD79a |
| TAG-72 | CD4 | CD28δ | CD79b |
| TAG-72 | CD4 | CD80 | CD8 |
| TAG-72 | CD4 | CD80 | CD3ζ |
| TAG-72 | CD4 | CD80 | CD3δ |
| TAG-72 | CD4 | CD80 | CD3γ |
| TAG-72 | CD4 | CD80 | CD3ε |
| TAG-72 | CD4 | CD80 | FcγRI-γ |
| TAG-72 | CD4 | CD80 | FcγRIII-γ |
| TAG-72 | CD4 | CD80 | FcεRIβ |
| TAG-72 | CD4 | CD80 | FcεRIγ |
| TAG-72 | CD4 | CD80 | DAP10 |
| TAG-72 | CD4 | CD80 | DAP12 |
| TAG-72 | CD4 | CD80 | CD32 |

TABLE 3-continued

Third Generation CARs

| ScFv | Co-stimulatory Signal | Co-stimulatory Signal | Signal Domain |
|---|---|---|---|
| TAG-72 | CD4 | CD80 | CD79a |
| TAG-72 | CD4 | CD80 | CD79b |
| TAG-72 | CD4 | CD86 | CD8 |
| TAG-72 | CD4 | CD86 | CD3ζ |
| TAG-72 | CD4 | CD86 | CD3δ |
| TAG-72 | CD4 | CD86 | CD3γ |
| TAG-72 | CD4 | CD86 | CD3ε |
| TAG-72 | CD4 | CD86 | FcγRI-γ |
| TAG-72 | CD4 | CD86 | FcγRIII-γ |
| TAG-72 | CD4 | CD86 | FcεRIβ |
| TAG-72 | CD4 | CD86 | FcεRIγ |
| TAG-72 | CD4 | CD86 | DAP10 |
| TAG-72 | CD4 | CD86 | DAP12 |
| TAG-72 | CD4 | CD86 | CD32 |
| TAG-72 | CD4 | CD86 | CD79a |
| TAG-72 | CD4 | CD86 | CD79b |
| TAG-72 | CD4 | OX40 | CD8 |
| TAG-72 | CD4 | OX40 | CD3ζ |
| TAG-72 | CD4 | OX40 | CD3δ |
| TAG-72 | CD4 | OX40 | CD3γ |
| TAG-72 | CD4 | OX40 | CD3ε |
| TAG-72 | CD4 | OX40 | FcγRI-γ |
| TAG-72 | CD4 | OX40 | FcγRIII-γ |
| TAG-72 | CD4 | OX40 | FcεRIβ |
| TAG-72 | CD4 | OX40 | FcεRIγ |
| TAG-72 | CD4 | OX40 | DAP10 |
| TAG-72 | CD4 | OX40 | DAP12 |
| TAG-72 | CD4 | OX40 | CD32 |
| TAG-72 | CD4 | OX40 | CD79a |
| TAG-72 | CD4 | OX40 | CD79b |
| TAG-72 | CD4 | DAP10 | CD8 |
| TAG-72 | CD4 | DAP10 | CD3ζ |
| TAG-72 | CD4 | DAP10 | CD3δ |
| TAG-72 | CD4 | DAP10 | CD3γ |
| TAG-72 | CD4 | DAP10 | CD3ε |
| TAG-72 | CD4 | DAP10 | FcγRI-γ |
| TAG-72 | CD4 | DAP10 | FcγRIII-γ |
| TAG-72 | CD4 | DAP10 | FcεRIβ |
| TAG-72 | CD4 | DAP10 | FcεRIγ |
| TAG-72 | CD4 | DAP10 | DAP10 |
| TAG-72 | CD4 | DAP10 | DAP12 |
| TAG-72 | CD4 | DAP10 | CD32 |
| TAG-72 | CD4 | DAP10 | CD79a |
| TAG-72 | CD4 | DAP10 | CD79b |
| TAG-72 | CD4 | DAP12 | CD8 |
| TAG-72 | CD4 | DAP12 | CD3ζ |
| TAG-72 | CD4 | DAP12 | CD3δ |
| TAG-72 | CD4 | DAP12 | CD3γ |
| TAG-72 | CD4 | DAP12 | CD3ε |
| TAG-72 | CD4 | DAP12 | FcγRI-γ |
| TAG-72 | CD4 | DAP12 | FcγRIII-γ |
| TAG-72 | CD4 | DAP12 | FcεRIβ |
| TAG-72 | CD4 | DAP12 | FcεRIγ |
| TAG-72 | CD4 | DAP12 | DAP10 |
| TAG-72 | CD4 | DAP12 | DAP12 |
| TAG-72 | CD4 | DAP12 | CD32 |
| TAG-72 | CD4 | DAP12 | CD79a |
| TAG-72 | CD4 | DAP12 | CD79b |
| TAG-72 | CD4 | MyD88 | CD8 |
| TAG-72 | CD4 | MyD88 | CD3ζ |
| TAG-72 | CD4 | MyD88 | CD3δ |
| TAG-72 | CD4 | MyD88 | CD3γ |
| TAG-72 | CD4 | MyD88 | CD3ε |
| TAG-72 | CD4 | MyD88 | FcγRI-γ |
| TAG-72 | CD4 | MyD88 | FcγRIII-γ |
| TAG-72 | CD4 | MyD88 | FcεRIβ |
| TAG-72 | CD4 | MyD88 | FcεRIγ |
| TAG-72 | CD4 | MyD88 | DAP10 |
| TAG-72 | CD4 | MyD88 | DAP12 |
| TAG-72 | CD4 | MyD88 | CD32 |
| TAG-72 | CD4 | MyD88 | CD79a |
| TAG-72 | CD4 | MyD88 | CD79b |
| TAG-72 | CD4 | CD7 | CD8 |
| TAG-72 | CD4 | CD7 | CD3ζ |
| TAG-72 | CD4 | CD7 | CD3δ |
| TAG-72 | CD4 | CD7 | CD3γ |
| TAG-72 | CD4 | CD7 | CD3ε |
| TAG-72 | CD4 | CD7 | FcγRI-γ |
| TAG-72 | CD4 | CD7 | FcγRIII-γ |
| TAG-72 | CD4 | CD7 | FcεRIβ |
| TAG-72 | CD4 | CD7 | FcεRIγ |
| TAG-72 | CD4 | CD7 | DAP10 |
| TAG-72 | CD4 | CD7 | DAP12 |
| TAG-72 | CD4 | CD7 | CD32 |
| TAG-72 | CD4 | CD7 | CD79a |
| TAG-72 | CD4 | CD7 | CD79b |
| TAG-72 | CD4 | BTNL3 | CD8 |
| TAG-72 | CD4 | BTNL3 | CD3ζ |
| TAG-72 | CD4 | BTNL3 | CD3δ |
| TAG-72 | CD4 | BTNL3 | CD3γ |
| TAG-72 | CD4 | BTNL3 | CD3ε |
| TAG-72 | CD4 | BTNL3 | FcγRI-γ |
| TAG-72 | CD4 | BTNL3 | FcγRIII-γ |
| TAG-72 | CD4 | BTNL3 | FcεRIβ |
| TAG-72 | CD4 | BTNL3 | FcεRIγ |
| TAG-72 | CD4 | BTNL3 | DAP10 |
| TAG-72 | CD4 | BTNL3 | DAP12 |
| TAG-72 | CD4 | BTNL3 | CD32 |
| TAG-72 | CD4 | BTNL3 | CD79a |
| TAG-72 | CD4 | BTNL3 | CD79b |
| TAG-72 | CD4 | NKG2D | CD8 |
| TAG-72 | CD4 | NKG2D | CD3ζ |
| TAG-72 | CD4 | NKG2D | CD3δ |
| TAG-72 | CD4 | NKG2D | CD3γ |
| TAG-72 | CD4 | NKG2D | CD3ε |
| TAG-72 | CD4 | NKG2D | FcγRI-γ |
| TAG-72 | CD4 | NKG2D | FcγRIII-γ |
| TAG-72 | CD4 | NKG2D | FcεRIβ |
| TAG-72 | CD4 | NKG2D | FcεRIγ |
| TAG-72 | CD4 | NKG2D | DAP10 |
| TAG-72 | CD4 | NKG2D | DAP12 |
| TAG-72 | CD4 | NKG2D | CD32 |
| TAG-72 | CD4 | NKG2D | CD79a |
| TAG-72 | CD4 | NKG2D | CD79b |
| TAG-72 | b2c | CD28 | CD8 |
| TAG-72 | b2c | CD28 | CD3ζ |
| TAG-72 | b2c | CD28 | CD3δ |
| TAG-72 | b2c | CD28 | CD3γ |
| TAG-72 | b2c | CD28 | CD3ε |
| TAG-72 | b2c | CD28 | FcγRI-γ |
| TAG-72 | b2c | CD28 | FcγRIII-γ |
| TAG-72 | b2c | CD28 | FcεRIβ |
| TAG-72 | b2c | CD28 | FcεRIγ |
| TAG-72 | b2c | CD28 | DAP10 |
| TAG-72 | b2c | CD28 | DAP12 |
| TAG-72 | b2c | CD28 | CD32 |
| TAG-72 | b2c | CD28 | CD79a |
| TAG-72 | b2c | CD28 | CD79b |
| TAG-72 | b2c | CD8 | CD8 |
| TAG-72 | b2c | CD8 | CD3ζ |
| TAG-72 | b2c | CD8 | CD3δ |
| TAG-72 | b2c | CD8 | CD3γ |
| TAG-72 | b2c | CD8 | CD3ε |
| TAG-72 | b2c | CD8 | FcγRI-γ |
| TAG-72 | b2c | CD8 | FcγRIII-γ |
| TAG-72 | b2c | CD8 | FcεRIβ |
| TAG-72 | b2c | CD8 | FcεRIγ |
| TAG-72 | b2c | CD8 | DAP10 |
| TAG-72 | b2c | CD8 | DAP12 |
| TAG-72 | b2c | CD8 | CD32 |
| TAG-72 | b2c | CD8 | CD79a |
| TAG-72 | b2c | CD8 | CD79b |
| TAG-72 | b2c | CD4 | CD8 |
| TAG-72 | b2c | CD4 | CD3ζ |
| TAG-72 | b2c | CD4 | CD3δ |
| TAG-72 | b2c | CD4 | CD3γ |
| TAG-72 | b2c | CD4 | CD3ε |
| TAG-72 | b2c | CD4 | FcγRI-γ |
| TAG-72 | b2c | CD4 | FcγRIII-γ |
| TAG-72 | b2c | CD4 | FcεRIβ |

TABLE 3-continued

Third Generation CARs

| ScFv | Co-stimulatory Signal | Co-stimulatory Signal | Signal Domain |
|---|---|---|---|
| TAG-72 | b2c | CD4 | FcεRIγ |
| TAG-72 | b2c | CD4 | DAP10 |
| TAG-72 | b2c | CD4 | DAP12 |
| TAG-72 | b2c | CD4 | CD32 |
| TAG-72 | b2c | CD4 | CD79a |
| TAG-72 | b2c | CD4 | CD79b |
| TAG-72 | b2c | b2c | CD8 |
| TAG-72 | b2c | b2c | CD3ζ |
| TAG-72 | b2c | b2c | CD3δ |
| TAG-72 | b2c | b2c | CD3γ |
| TAG-72 | b2c | b2c | CD3ε |
| TAG-72 | b2c | b2c | FcγRI-γ |
| TAG-72 | b2c | b2c | FcγRIII-γ |
| TAG-72 | b2c | b2c | FcεRIβ |
| TAG-72 | b2c | b2c | FcεRIγ |
| TAG-72 | b2c | b2c | DAP10 |
| TAG-72 | b2c | b2c | DAP12 |
| TAG-72 | b2c | b2c | CD32 |
| TAG-72 | b2c | b2c | CD79a |
| TAG-72 | b2c | b2c | CD79b |
| TAG-72 | b2c | CD137/41BB | CD8 |
| TAG-72 | b2c | CD137/41BB | CD3ζ |
| TAG-72 | b2c | CD137/41BB | CD3δ |
| TAG-72 | b2c | CD137/41BB | CD3γ |
| TAG-72 | b2c | CD137/41BB | CD3ε |
| TAG-72 | b2c | CD137/41BB | FcγRI-γ |
| TAG-72 | b2c | CD137/41BB | FcγRIII-γ |
| TAG-72 | b2c | CD137/41BB | FcεRIβ |
| TAG-72 | b2c | CD137/41BB | FcεRIγ |
| TAG-72 | b2c | CD137/41BB | DAP10 |
| TAG-72 | b2c | CD137/41BB | DAP12 |
| TAG-72 | b2c | CD137/41BB | CD32 |
| TAG-72 | b2c | CD137/41BB | CD79a |
| TAG-72 | b2c | CD137/41BB | CD79b |
| TAG-72 | b2c | ICOS | CD8 |
| TAG-72 | b2c | ICOS | CD3ζ |
| TAG-72 | b2c | ICOS | CD3δ |
| TAG-72 | b2c | ICOS | CD3γ |
| TAG-72 | b2c | ICOS | CD3ε |
| TAG-72 | b2c | ICOS | FcγRI-γ |
| TAG-72 | b2c | ICOS | FcγRIII-γ |
| TAG-72 | b2c | ICOS | FcεRIβ |
| TAG-72 | b2c | ICOS | FcεRIγ |
| TAG-72 | b2c | ICOS | DAP10 |
| TAG-72 | b2c | ICOS | DAP12 |
| TAG-72 | b2c | ICOS | CD32 |
| TAG-72 | b2c | ICOS | CD79a |
| TAG-72 | b2c | ICOS | CD79b |
| TAG-72 | b2c | CD27 | CD8 |
| TAG-72 | b2c | CD27 | CD3ζ |
| TAG-72 | b2c | CD27 | CD3δ |
| TAG-72 | b2c | CD27 | CD3γ |
| TAG-72 | b2c | CD27 | CD3ε |
| TAG-72 | b2c | CD27 | FcγRI-γ |
| TAG-72 | b2c | CD27 | FcγRIII-γ |
| TAG-72 | b2c | CD27 | FcεRIβ |
| TAG-72 | b2c | CD27 | FcεRIγ |
| TAG-72 | b2c | CD27 | DAP10 |
| TAG-72 | b2c | CD27 | DAP12 |
| TAG-72 | b2c | CD27 | CD32 |
| TAG-72 | b2c | CD27 | CD79a |
| TAG-72 | b2c | CD27 | CD79b |
| TAG-72 | b2c | CD28δ | CD8 |
| TAG-72 | b2c | CD28δ | CD3ζ |
| TAG-72 | b2c | CD28δ | CD3δ |
| TAG-72 | b2c | CD28δ | CD3γ |
| TAG-72 | b2c | CD28δ | CD3ε |
| TAG-72 | b2c | CD28δ | FcγRI-γ |
| TAG-72 | b2c | CD28δ | FcγRIII-γ |
| TAG-72 | b2c | CD28δ | FcεRIβ |
| TAG-72 | b2c | CD28δ | FcεRIγ |
| TAG-72 | b2c | CD28δ | DAP10 |
| TAG-72 | b2c | CD28δ | DAP12 |
| TAG-72 | b2c | CD28δ | CD32 |
| TAG-72 | b2c | CD28δ | CD79a |
| TAG-72 | b2c | CD28δ | CD79b |
| TAG-72 | b2c | CD80 | CD8 |
| TAG-72 | b2c | CD80 | CD3ζ |
| TAG-72 | b2c | CD80 | CD3δ |
| TAG-72 | b2c | CD80 | CD3γ |
| TAG-72 | b2c | CD80 | CD3ε |
| TAG-72 | b2c | CD80 | FcγRI-γ |
| TAG-72 | b2c | CD80 | FcγRIII-γ |
| TAG-72 | b2c | CD80 | FcεRIβ |
| TAG-72 | b2c | CD80 | FcεRIγ |
| TAG-72 | b2c | CD80 | DAP10 |
| TAG-72 | b2c | CD80 | DAP12 |
| TAG-72 | b2c | CD80 | CD32 |
| TAG-72 | b2c | CD80 | CD79a |
| TAG-72 | b2c | CD80 | CD79b |
| TAG-72 | b2c | CD86 | CD8 |
| TAG-72 | b2c | CD86 | CD3ζ |
| TAG-72 | b2c | CD86 | CD3δ |
| TAG-72 | b2c | CD86 | CD3γ |
| TAG-72 | b2c | CD86 | CD3ε |
| TAG-72 | b2c | CD86 | FcγRI-γ |
| TAG-72 | b2c | CD86 | FcγRIII-γ |
| TAG-72 | b2c | CD86 | FcεRIβ |
| TAG-72 | b2c | CD86 | FcεRIγ |
| TAG-72 | b2c | CD86 | DAP10 |
| TAG-72 | b2c | CD86 | DAP12 |
| TAG-72 | b2c | CD86 | CD32 |
| TAG-72 | b2c | CD86 | CD79a |
| TAG-72 | b2c | CD86 | CD79b |
| TAG-72 | b2c | OX40 | CD8 |
| TAG-72 | b2c | OX40 | CD3ζ |
| TAG-72 | b2c | OX40 | CD3δ |
| TAG-72 | b2c | OX40 | CD3γ |
| TAG-72 | b2c | OX40 | CD3ε |
| TAG-72 | b2c | OX40 | FcγRI-γ |
| TAG-72 | b2c | OX40 | FcγRIII-γ |
| TAG-72 | b2c | OX40 | FcεRIβ |
| TAG-72 | b2c | OX40 | FcεRIγ |
| TAG-72 | b2c | OX40 | DAP10 |
| TAG-72 | b2c | OX40 | DAP12 |
| TAG-72 | b2c | OX40 | CD32 |
| TAG-72 | b2c | OX40 | CD79a |
| TAG-72 | b2c | OX40 | CD79b |
| TAG-72 | b2c | DAP10 | CD8 |
| TAG-72 | b2c | DAP10 | CD3ζ |
| TAG-72 | b2c | DAP10 | CD3δ |
| TAG-72 | b2c | DAP10 | CD3γ |
| TAG-72 | b2c | DAP10 | CD3ε |
| TAG-72 | b2c | DAP10 | FcγRI-γ |
| TAG-72 | b2c | DAP10 | FcγRIII-γ |
| TAG-72 | b2c | DAP10 | FcεRIβ |
| TAG-72 | b2c | DAP10 | FcεRIγ |
| TAG-72 | b2c | DAP10 | DAP10 |
| TAG-72 | b2c | DAP10 | DAP12 |
| TAG-72 | b2c | DAP10 | CD32 |
| TAG-72 | b2c | DAP10 | CD79a |
| TAG-72 | b2c | DAP10 | CD79b |
| TAG-72 | b2c | DAP12 | CD8 |
| TAG-72 | b2c | DAP12 | CD3ζ |
| TAG-72 | b2c | DAP12 | CD3δ |
| TAG-72 | b2c | DAP12 | CD3γ |
| TAG-72 | b2c | DAP12 | CD3ε |
| TAG-72 | b2c | DAP12 | FcγRI-γ |
| TAG-72 | b2c | DAP12 | FcγRIII-γ |
| TAG-72 | b2c | DAP12 | FcεRIβ |
| TAG-72 | b2c | DAP12 | FcεRIγ |
| TAG-72 | b2c | DAP12 | DAP10 |
| TAG-72 | b2c | DAP12 | DAP12 |
| TAG-72 | b2c | DAP12 | CD32 |
| TAG-72 | b2c | DAP12 | CD79a |
| TAG-72 | b2c | DAP12 | CD79b |
| TAG-72 | b2c | MyD88 | CD8 |
| TAG-72 | b2c | MyD88 | CD3ζ |
| TAG-72 | b2c | MyD88 | CD3δ |
| TAG-72 | b2c | MyD88 | CD3γ |

TABLE 3-continued

Third Generation CARs

| ScFv | Co-stimulatory Signal | Co-stimulatory Signal | Signal Domain |
|---|---|---|---|
| TAG-72 | b2c | MyD88 | CD3ε |
| TAG-72 | b2c | MyD88 | FcγRI-γ |
| TAG-72 | b2c | MyD88 | FcγRIII-γ |
| TAG-72 | b2c | MyD88 | FcεRIβ |
| TAG-72 | b2c | MyD88 | FcεRIγ |
| TAG-72 | b2c | MyD88 | DAP10 |
| TAG-72 | b2c | MyD88 | DAP12 |
| TAG-72 | b2c | MyD88 | CD32 |
| TAG-72 | b2c | MyD88 | CD79a |
| TAG-72 | b2c | MyD88 | CD79b |
| TAG-72 | b2c | CD7 | CD8 |
| TAG-72 | b2c | CD7 | CD3ζ |
| TAG-72 | b2c | CD7 | CD3δ |
| TAG-72 | b2c | CD7 | CD3γ |
| TAG-72 | b2c | CD7 | CD3ε |
| TAG-72 | b2c | CD7 | FcγRI-γ |
| TAG-72 | b2c | CD7 | FcγRIII-γ |
| TAG-72 | b2c | CD7 | FcεRIβ |
| TAG-72 | b2c | CD7 | FcεRIγ |
| TAG-72 | b2c | CD7 | DAP10 |
| TAG-72 | b2c | CD7 | DAP12 |
| TAG-72 | b2c | CD7 | CD32 |
| TAG-72 | b2c | CD7 | CD79a |
| TAG-72 | b2c | CD7 | CD79b |
| TAG-72 | b2c | BTNL3 | CD8 |
| TAG-72 | b2c | BTNL3 | CD3ζ |
| TAG-72 | b2c | BTNL3 | CD3δ |
| TAG-72 | b2c | BTNL3 | CD3γ |
| TAG-72 | b2c | BTNL3 | CD3ε |
| TAG-72 | b2c | BTNL3 | FcγRI-γ |
| TAG-72 | b2c | BTNL3 | FcγRIII-γ |
| TAG-72 | b2c | BTNL3 | FcεRIβ |
| TAG-72 | b2c | BTNL3 | FcεRIγ |
| TAG-72 | b2c | BTNL3 | DAP10 |
| TAG-72 | b2c | BTNL3 | DAP12 |
| TAG-72 | b2c | BTNL3 | CD32 |
| TAG-72 | b2c | BTNL3 | CD79a |
| TAG-72 | b2c | BTNL3 | CD79b |
| TAG-72 | b2c | NKG2D | CD8 |
| TAG-72 | b2c | NKG2D | CD3ζ |
| TAG-72 | b2c | NKG2D | CD3δ |
| TAG-72 | b2c | NKG2D | CD3γ |
| TAG-72 | b2c | NKG2D | CD3ε |
| TAG-72 | b2c | NKG2D | FcγRI-γ |
| TAG-72 | b2c | NKG2D | FcγRIII-γ |
| TAG-72 | b2c | NKG2D | FcεRIβ |
| TAG-72 | b2c | NKG2D | FcεRIγ |
| TAG-72 | b2c | NKG2D | DAP10 |
| TAG-72 | b2c | NKG2D | DAP12 |
| TAG-72 | b2c | NKG2D | CD32 |
| TAG-72 | b2c | NKG2D | CD79a |
| TAG-72 | b2c | NKG2D | CD79b |
| TAG-72 | CD137/41BB | CD28 | CD8 |
| TAG-72 | CD137/41BB | CD28 | CD3ζ |
| TAG-72 | CD137/41BB | CD28 | CD3δ |
| TAG-72 | CD137/41BB | CD28 | CD3γ |
| TAG-72 | CD137/41BB | CD28 | CD3ε |
| TAG-72 | CD137/41BB | CD28 | FcγRI-γ |
| TAG-72 | CD137/41BB | CD28 | FcγRIII-γ |
| TAG-72 | CD137/41BB | CD28 | FcεRIβ |
| TAG-72 | CD137/41BB | CD28 | FcεRIγ |
| TAG-72 | CD137/41BB | CD28 | DAP10 |
| TAG-72 | CD137/41BB | CD28 | DAP12 |
| TAG-72 | CD137/41BB | CD28 | CD32 |
| TAG-72 | CD137/41BB | CD28 | CD79a |
| TAG-72 | CD137/41BB | CD28 | CD79b |
| TAG-72 | CD137/41BB | CD8 | CD8 |
| TAG-72 | CD137/41BB | CD8 | CD3ζ |
| TAG-72 | CD137/41BB | CD8 | CD3δ |
| TAG-72 | CD137/41BB | CD8 | CD3γ |
| TAG-72 | CD137/41BB | CD8 | CD3ε |
| TAG-72 | CD137/41BB | CD8 | FcγRI-γ |
| TAG-72 | CD137/41BB | CD8 | FcγRIII-γ |
| TAG-72 | CD137/41BB | CD8 | FcεRIβ |
| TAG-72 | CD137/41BB | CD8 | FcεRIγ |
| TAG-72 | CD137/41BB | CD8 | DAP10 |
| TAG-72 | CD137/41BB | CD8 | DAP12 |
| TAG-72 | CD137/41BB | CD8 | CD32 |
| TAG-72 | CD137/41BB | CD8 | CD79a |
| TAG-72 | CD137/41BB | CD8 | CD79b |
| TAG-72 | CD137/41BB | CD4 | CD8 |
| TAG-72 | CD137/41BB | CD4 | CD3ζ |
| TAG-72 | CD137/41BB | CD4 | CD3δ |
| TAG-72 | CD137/41BB | CD4 | CD3γ |
| TAG-72 | CD137/41BB | CD4 | CD3ε |
| TAG-72 | CD137/41BB | CD4 | FcγRI-γ |
| TAG-72 | CD137/41BB | CD4 | FcγRIII-γ |
| TAG-72 | CD137/41BB | CD4 | FcεRIβ |
| TAG-72 | CD137/41BB | CD4 | FcεRIγ |
| TAG-72 | CD137/41BB | CD4 | DAP10 |
| TAG-72 | CD137/41BB | CD4 | DAP12 |
| TAG-72 | CD137/41BB | CD4 | CD32 |
| TAG-72 | CD137/41BB | CD4 | CD79a |
| TAG-72 | CD137/41BB | CD4 | CD79b |
| TAG-72 | CD137/41BB | b2c | CD8 |
| TAG-72 | CD137/41BB | b2c | CD3ζ |
| TAG-72 | CD137/41BB | b2c | CD3δ |
| TAG-72 | CD137/41BB | b2c | CD3γ |
| TAG-72 | CD137/41BB | b2c | CD3ε |
| TAG-72 | CD137/41BB | b2c | FcγRI-γ |
| TAG-72 | CD137/41BB | b2c | FcγRIII-γ |
| TAG-72 | CD137/41BB | b2c | FcεRIβ |
| TAG-72 | CD137/41BB | b2c | FcεRIγ |
| TAG-72 | CD137/41BB | b2c | DAP10 |
| TAG-72 | CD137/41BB | b2c | DAP12 |
| TAG-72 | CD137/41BB | b2c | CD32 |
| TAG-72 | CD137/41BB | b2c | CD79a |
| TAG-72 | CD137/41BB | b2c | CD79b |
| TAG-72 | CD137/41BB | CD137/41BB | CD8 |
| TAG-72 | CD137/41BB | CD137/41BB | CD3ζ |
| TAG-72 | CD137/41BB | CD137/41BB | CD3δ |
| TAG-72 | CD137/41BB | CD137/41BB | CD3γ |
| TAG-72 | CD137/41BB | CD137/41BB | CD3ε |
| TAG-72 | CD137/41BB | CD137/41BB | FcγRI-γ |
| TAG-72 | CD137/41BB | CD137/41BB | FcγRIII-γ |
| TAG-72 | CD137/41BB | CD137/41BB | FcεRIβ |
| TAG-72 | CD137/41BB | CD137/41BB | FcεRIγ |
| TAG-72 | CD137/41BB | CD137/41BB | DAP10 |
| TAG-72 | CD137/41BB | CD137/41BB | DAP12 |
| TAG-72 | CD137/41BB | CD137/41BB | CD32 |
| TAG-72 | CD137/41BB | CD137/41BB | CD79a |
| TAG-72 | CD137/41BB | CD137/41BB | CD79b |
| TAG-72 | CD137/41BB | ICOS | CD8 |
| TAG-72 | CD137/41BB | ICOS | CD3ζ |
| TAG-72 | CD137/41BB | ICOS | CD3δ |
| TAG-72 | CD137/41BB | ICOS | CD3γ |
| TAG-72 | CD137/41BB | ICOS | CD3ε |
| TAG-72 | CD137/41BB | ICOS | FcγRI-γ |
| TAG-72 | CD137/41BB | ICOS | FcγRIII-γ |
| TAG-72 | CD137/41BB | ICOS | FcεRIβ |
| TAG-72 | CD137/41BB | ICOS | FcεRIγ |
| TAG-72 | CD137/41BB | ICOS | DAP10 |
| TAG-72 | CD137/41BB | ICOS | DAP12 |
| TAG-72 | CD137/41BB | ICOS | CD32 |
| TAG-72 | CD137/41BB | ICOS | CD79a |
| TAG-72 | CD137/41BB | ICOS | CD79b |
| TAG-72 | CD137/41BB | CD27 | CD8 |
| TAG-72 | CD137/41BB | CD27 | CD3ζ |
| TAG-72 | CD137/41BB | CD27 | CD3δ |
| TAG-72 | CD137/41BB | CD27 | CD3γ |
| TAG-72 | CD137/41BB | CD27 | CD3ε |
| TAG-72 | CD137/41BB | CD27 | FcγRI-γ |
| TAG-72 | CD137/41BB | CD27 | FcγRIII-γ |
| TAG-72 | CD137/41BB | CD27 | FcεRIβ |
| TAG-72 | CD137/41BB | CD27 | FcεRIγ |
| TAG-72 | CD137/41BB | CD27 | DAP10 |
| TAG-72 | CD137/41BB | CD27 | DAP12 |
| TAG-72 | CD137/41BB | CD27 | CD32 |
| TAG-72 | CD137/41BB | CD27 | CD79a |
| TAG-72 | CD137/41BB | CD27 | CD79b |

TABLE 3-continued

Third Generation CARs

| ScFv | Co-stimulatory Signal | Co-stimulatory Signal | Signal Domain |
|---|---|---|---|
| TAG-72 | CD137/41BB | CD28δ | CD8 |
| TAG-72 | CD137/41BB | CD28δ | CD3ζ |
| TAG-72 | CD137/41BB | CD28δ | CD3δ |
| TAG-72 | CD137/41BB | CD28δ | CD3γ |
| TAG-72 | CD137/41BB | CD28δ | CD3ε |
| TAG-72 | CD137/41BB | CD28δ | FcγRI-γ |
| TAG-72 | CD137/41BB | CD28δ | FcγRIII-γ |
| TAG-72 | CD137/41BB | CD28δ | FcεRIβ |
| TAG-72 | CD137/41BB | CD28δ | FcεRIγ |
| TAG-72 | CD137/41BB | CD28δ | DAP10 |
| TAG-72 | CD137/41BB | CD28δ | DAP12 |
| TAG-72 | CD137/41BB | CD28δ | CD32 |
| TAG-72 | CD137/41BB | CD28δ | CD79a |
| TAG-72 | CD137/41BB | CD28δ | CD79b |
| TAG-72 | CD137/41BB | CD80 | CD8 |
| TAG-72 | CD137/41BB | CD80 | CD3ζ |
| TAG-72 | CD137/41BB | CD80 | CD3δ |
| TAG-72 | CD137/41BB | CD80 | CD3γ |
| TAG-72 | CD137/41BB | CD80 | CD3ε |
| TAG-72 | CD137/41BB | CD80 | FcγRI-γ |
| TAG-72 | CD137/41BB | CD80 | FcγRIII-γ |
| TAG-72 | CD137/41BB | CD80 | FcεRIβ |
| TAG-72 | CD137/41BB | CD80 | FcεRIγ |
| TAG-72 | CD137/41BB | CD80 | DAP10 |
| TAG-72 | CD137/41BB | CD80 | DAP12 |
| TAG-72 | CD137/41BB | CD80 | CD32 |
| TAG-72 | CD137/41BB | CD80 | CD79a |
| TAG-72 | CD137/41BB | CD80 | CD79b |
| TAG-72 | CD137/41BB | CD86 | CD8 |
| TAG-72 | CD137/41BB | CD86 | CD3ζ |
| TAG-72 | CD137/41BB | CD86 | CD3δ |
| TAG-72 | CD137/41BB | CD86 | CD3γ |
| TAG-72 | CD137/41BB | CD86 | CD3ε |
| TAG-72 | CD137/41BB | CD86 | FcγRI-γ |
| TAG-72 | CD137/41BB | CD86 | FcγRIII-γ |
| TAG-72 | CD137/41BB | CD86 | FcεRIβ |
| TAG-72 | CD137/41BB | CD86 | FcεRIγ |
| TAG-72 | CD137/41BB | CD86 | DAP10 |
| TAG-72 | CD137/41BB | CD86 | DAP12 |
| TAG-72 | CD137/41BB | CD86 | CD32 |
| TAG-72 | CD137/41BB | CD86 | CD79a |
| TAG-72 | CD137/41BB | CD86 | CD79b |
| TAG-72 | CD137/41BB | OX40 | CD8 |
| TAG-72 | CD137/41BB | OX40 | CD3ζ |
| TAG-72 | CD137/41BB | OX40 | CD3δ |
| TAG-72 | CD137/41BB | OX40 | CD3γ |
| TAG-72 | CD137/41BB | OX40 | CD3ε |
| TAG-72 | CD137/41BB | OX40 | FcγRI-γ |
| TAG-72 | CD137/41BB | OX40 | FcγRIII-γ |
| TAG-72 | CD137/41BB | OX40 | FcεRIβ |
| TAG-72 | CD137/41BB | OX40 | FcεRIγ |
| TAG-72 | CD137/41BB | OX40 | DAP10 |
| TAG-72 | CD137/41BB | OX40 | DAP12 |
| TAG-72 | CD137/41BB | OX40 | CD32 |
| TAG-72 | CD137/41BB | OX40 | CD79a |
| TAG-72 | CD137/41BB | OX40 | CD79b |
| TAG-72 | CD137/41BB | DAP10 | CD8 |
| TAG-72 | CD137/41BB | DAP10 | CD3ζ |
| TAG-72 | CD137/41BB | DAP10 | CD3δ |
| TAG-72 | CD137/41BB | DAP10 | CD3γ |
| TAG-72 | CD137/41BB | DAP10 | CD3ε |
| TAG-72 | CD137/41BB | DAP10 | FcγRI-γ |
| TAG-72 | CD137/41BB | DAP10 | FcγRIII-γ |
| TAG-72 | CD137/41BB | DAP10 | FcεRIβ |
| TAG-72 | CD137/41BB | DAP10 | FcεRIγ |
| TAG-72 | CD137/41BB | DAP10 | DAP10 |
| TAG-72 | CD137/41BB | DAP10 | DAP12 |
| TAG-72 | CD137/41BB | DAP10 | CD32 |
| TAG-72 | CD137/41BB | DAP10 | CD79a |
| TAG-72 | CD137/41BB | DAP10 | CD79b |
| TAG-72 | CD137/41BB | DAP12 | CD8 |
| TAG-72 | CD137/41BB | DAP12 | CD3ζ |
| TAG-72 | CD137/41BB | DAP12 | CD3δ |
| TAG-72 | CD137/41BB | DAP12 | CD3γ |
| TAG-72 | CD137/41BB | DAP12 | CD3ε |
| TAG-72 | CD137/41BB | DAP12 | FcγRI-γ |
| TAG-72 | CD137/41BB | DAP12 | FcγRIII-γ |
| TAG-72 | CD137/41BB | DAP12 | FcεRIβ |
| TAG-72 | CD137/41BB | DAP12 | FcεRIγ |
| TAG-72 | CD137/41BB | DAP12 | DAP10 |
| TAG-72 | CD137/41BB | DAP12 | DAP12 |
| TAG-72 | CD137/41BB | DAP12 | CD32 |
| TAG-72 | CD137/41BB | DAP12 | CD79a |
| TAG-72 | CD137/41BB | DAP12 | CD79b |
| TAG-72 | CD137/41BB | MyD88 | CD8 |
| TAG-72 | CD137/41BB | MyD88 | CD3ζ |
| TAG-72 | CD137/41BB | MyD88 | CD3δ |
| TAG-72 | CD137/41BB | MyD88 | CD3γ |
| TAG-72 | CD137/41BB | MyD88 | CD3ε |
| TAG-72 | CD137/41BB | MyD88 | FcγRI-γ |
| TAG-72 | CD137/41BB | MyD88 | FcγRIII-γ |
| TAG-72 | CD137/41BB | MyD88 | FcεRIβ |
| TAG-72 | CD137/41BB | MyD88 | FcεRIγ |
| TAG-72 | CD137/41BB | MyD88 | DAP10 |
| TAG-72 | CD137/41BB | MyD88 | DAP12 |
| TAG-72 | CD137/41BB | MyD88 | CD32 |
| TAG-72 | CD137/41BB | MyD88 | CD79a |
| TAG-72 | CD137/41BB | MyD88 | CD79b |
| TAG-72 | CD137/41BB | CD7 | CD8 |
| TAG-72 | CD137/41BB | CD7 | CD3ζ |
| TAG-72 | CD137/41BB | CD7 | CD3δ |
| TAG-72 | CD137/41BB | CD7 | CD3γ |
| TAG-72 | CD137/41BB | CD7 | CD3ε |
| TAG-72 | CD137/41BB | CD7 | FcγRI-γ |
| TAG-72 | CD137/41BB | CD7 | FcγRIII-γ |
| TAG-72 | CD137/41BB | CD7 | FcεRIβ |
| TAG-72 | CD137/41BB | CD7 | FcεRIγ |
| TAG-72 | CD137/41BB | CD7 | DAP10 |
| TAG-72 | CD137/41BB | CD7 | DAP12 |
| TAG-72 | CD137/41BB | CD7 | CD32 |
| TAG-72 | CD137/41BB | CD7 | CD79a |
| TAG-72 | CD137/41BB | CD7 | CD79b |
| TAG-72 | CD137/41BB | BTNL3 | CD8 |
| TAG-72 | CD137/41BB | BTNL3 | CD3ζ |
| TAG-72 | CD137/41BB | BTNL3 | CD3δ |
| TAG-72 | CD137/41BB | BTNL3 | CD3γ |
| TAG-72 | CD137/41BB | BTNL3 | CD3ε |
| TAG-72 | CD137/41BB | BTNL3 | FcγRI-γ |
| TAG-72 | CD137/41BB | BTNL3 | FcγRIII-γ |
| TAG-72 | CD137/41BB | BTNL3 | FcεRIβ |
| TAG-72 | CD137/41BB | BTNL3 | FcεRIγ |
| TAG-72 | CD137/41BB | BTNL3 | DAP10 |
| TAG-72 | CD137/41BB | BTNL3 | DAP12 |
| TAG-72 | CD137/41BB | BTNL3 | CD32 |
| TAG-72 | CD137/41BB | BTNL3 | CD79a |
| TAG-72 | CD137/41BB | BTNL3 | CD79b |
| TAG-72 | CD137/41BB | NKG2D | CD8 |
| TAG-72 | CD137/41BB | NKG2D | CD3ζ |
| TAG-72 | CD137/41BB | NKG2D | CD3δ |
| TAG-72 | CD137/41BB | NKG2D | CD3γ |
| TAG-72 | CD137/41BB | NKG2D | CD3ε |
| TAG-72 | CD137/41BB | NKG2D | FcγRI-γ |
| TAG-72 | CD137/41BB | NKG2D | FcγRIII-γ |
| TAG-72 | CD137/41BB | NKG2D | FcεRIβ |
| TAG-72 | CD137/41BB | NKG2D | FcεRIγ |
| TAG-72 | CD137/41BB | NKG2D | DAP10 |
| TAG-72 | CD137/41BB | NKG2D | DAP12 |
| TAG-72 | CD137/41BB | NKG2D | CD32 |
| TAG-72 | CD137/41BB | NKG2D | CD79a |
| TAG-72 | CD137/41BB | NKG2D | CD79b |
| TAG-72 | ICOS | CD28 | CD8 |
| TAG-72 | ICOS | CD28 | CD3ζ |
| TAG-72 | ICOS | CD28 | CD3δ |
| TAG-72 | ICOS | CD28 | CD3γ |
| TAG-72 | ICOS | CD28 | CD3ε |
| TAG-72 | ICOS | CD28 | FcγRI-γ |
| TAG-72 | ICOS | CD28 | FcγRIII-γ |
| TAG-72 | ICOS | CD28 | FcεRIβ |
| TAG-72 | ICOS | CD28 | FcεRIγ |
| TAG-72 | ICOS | CD28 | DAP10 |

TABLE 3-continued

Third Generation CARs

| ScFv | Co-stimulatory Signal | Co-stimulatory Signal | Signal Domain |
|---|---|---|---|
| TAG-72 | ICOS | CD28 | DAP12 |
| TAG-72 | ICOS | CD28 | CD32 |
| TAG-72 | ICOS | CD28 | CD79a |
| TAG-72 | ICOS | CD28 | CD79b |
| TAG-72 | ICOS | CD8 | CD8 |
| TAG-72 | ICOS | CD8 | CD3ζ |
| TAG-72 | ICOS | CD8 | CD3δ |
| TAG-72 | ICOS | CD8 | CD3γ |
| TAG-72 | ICOS | CD8 | CD3ε |
| TAG-72 | ICOS | CD8 | FcγRI-γ |
| TAG-72 | ICOS | CD8 | FcγRIII-γ |
| TAG-72 | ICOS | CD8 | FcεRIβ |
| TAG-72 | ICOS | CD8 | FcεRIγ |
| TAG-72 | ICOS | CD8 | DAP10 |
| TAG-72 | ICOS | CD8 | DAP12 |
| TAG-72 | ICOS | CD8 | CD32 |
| TAG-72 | ICOS | CD8 | CD79a |
| TAG-72 | ICOS | CD8 | CD79b |
| TAG-72 | ICOS | CD4 | CD8 |
| TAG-72 | ICOS | CD4 | CD3ζ |
| TAG-72 | ICOS | CD4 | CD3δ |
| TAG-72 | ICOS | CD4 | CD3γ |
| TAG-72 | ICOS | CD4 | CD3ε |
| TAG-72 | ICOS | CD4 | FcγRI-γ |
| TAG-72 | ICOS | CD4 | FcγRIII-γ |
| TAG-72 | ICOS | CD4 | FcεRIβ |
| TAG-72 | ICOS | CD4 | FcεRIγ |
| TAG-72 | ICOS | CD4 | DAP10 |
| TAG-72 | ICOS | CD4 | DAP12 |
| TAG-72 | ICOS | CD4 | CD32 |
| TAG-72 | ICOS | CD4 | CD79a |
| TAG-72 | ICOS | CD4 | CD79b |
| TAG-72 | ICOS | b2c | CD8 |
| TAG-72 | ICOS | b2c | CD3ζ |
| TAG-72 | ICOS | b2c | CD3δ |
| TAG-72 | ICOS | b2c | CD3γ |
| TAG-72 | ICOS | b2c | CD3ε |
| TAG-72 | ICOS | b2c | FcγRI-γ |
| TAG-72 | ICOS | b2c | FcγRIII-γ |
| TAG-72 | ICOS | b2c | FcεRIβ |
| TAG-72 | ICOS | b2c | FcεRIγ |
| TAG-72 | ICOS | b2c | DAP10 |
| TAG-72 | ICOS | b2c | DAP12 |
| TAG-72 | ICOS | b2c | CD32 |
| TAG-72 | ICOS | b2c | CD79a |
| TAG-72 | ICOS | b2c | CD79b |
| TAG-72 | ICOS | CD137/41BB | CD8 |
| TAG-72 | ICOS | CD137/41BB | CD3ζ |
| TAG-72 | ICOS | CD137/41BB | CD3δ |
| TAG-72 | ICOS | CD137/41BB | CD3γ |
| TAG-72 | ICOS | CD137/41BB | CD3ε |
| TAG-72 | ICOS | CD137/41BB | FcγRI-γ |
| TAG-72 | ICOS | CD137/41BB | FcγRIII-γ |
| TAG-72 | ICOS | CD137/41BB | FcεRIβ |
| TAG-72 | ICOS | CD137/41BB | FcεRIγ |
| TAG-72 | ICOS | CD137/41BB | DAP10 |
| TAG-72 | ICOS | CD137/41BB | DAP12 |
| TAG-72 | ICOS | CD137/41BB | CD32 |
| TAG-72 | ICOS | CD137/41BB | CD79a |
| TAG-72 | ICOS | CD137/41BB | CD79b |
| TAG-72 | ICOS | ICOS | CD8 |
| TAG-72 | ICOS | ICOS | CD3ζ |
| TAG-72 | ICOS | ICOS | CD3δ |
| TAG-72 | ICOS | ICOS | CD3γ |
| TAG-72 | ICOS | ICOS | CD3ε |
| TAG-72 | ICOS | ICOS | FcγRI-γ |
| TAG-72 | ICOS | ICOS | FcγRIII-γ |
| TAG-72 | ICOS | ICOS | FcεRIβ |
| TAG-72 | ICOS | ICOS | FcεRIγ |
| TAG-72 | ICOS | ICOS | DAP10 |
| TAG-72 | ICOS | ICOS | DAP12 |
| TAG-72 | ICOS | ICOS | CD32 |
| TAG-72 | ICOS | ICOS | CD79a |
| TAG-72 | ICOS | ICOS | CD79b |
| TAG-72 | ICOS | CD27 | CD8 |
| TAG-72 | ICOS | CD27 | CD3ζ |
| TAG-72 | ICOS | CD27 | CD3δ |
| TAG-72 | ICOS | CD27 | CD3γ |
| TAG-72 | ICOS | CD27 | CD3ε |
| TAG-72 | ICOS | CD27 | FcγRI-γ |
| TAG-72 | ICOS | CD27 | FcγRIII-γ |
| TAG-72 | ICOS | CD27 | FcεRIβ |
| TAG-72 | ICOS | CD27 | FcεRIγ |
| TAG-72 | ICOS | CD27 | DAP10 |
| TAG-72 | ICOS | CD27 | DAP12 |
| TAG-72 | ICOS | CD27 | CD32 |
| TAG-72 | ICOS | CD27 | CD79a |
| TAG-72 | ICOS | CD27 | CD79b |
| TAG-72 | ICOS | CD28δ | CD8 |
| TAG-72 | ICOS | CD28δ | CD3ζ |
| TAG-72 | ICOS | CD28δ | CD3δ |
| TAG-72 | ICOS | CD28δ | CD3γ |
| TAG-72 | ICOS | CD28δ | CD3ε |
| TAG-72 | ICOS | CD28δ | FcγRI-γ |
| TAG-72 | ICOS | CD28δ | FcγRIII-γ |
| TAG-72 | ICOS | CD28δ | FcεRIβ |
| TAG-72 | ICOS | CD28δ | FcεRIγ |
| TAG-72 | ICOS | CD28δ | DAP10 |
| TAG-72 | ICOS | CD28δ | DAP12 |
| TAG-72 | ICOS | CD28δ | CD32 |
| TAG-72 | ICOS | CD28δ | CD79a |
| TAG-72 | ICOS | CD28δ | CD79b |
| TAG-72 | ICOS | CD80 | CD8 |
| TAG-72 | ICOS | CD80 | CD3ζ |
| TAG-72 | ICOS | CD80 | CD3δ |
| TAG-72 | ICOS | CD80 | CD3γ |
| TAG-72 | ICOS | CD80 | CD3ε |
| TAG-72 | ICOS | CD80 | FcγRI-γ |
| TAG-72 | ICOS | CD80 | FcγRIII-γ |
| TAG-72 | ICOS | CD80 | FcεRIβ |
| TAG-72 | ICOS | CD80 | FcεRIγ |
| TAG-72 | ICOS | CD80 | DAP10 |
| TAG-72 | ICOS | CD80 | DAP12 |
| TAG-72 | ICOS | CD80 | CD32 |
| TAG-72 | ICOS | CD80 | CD79a |
| TAG-72 | ICOS | CD80 | CD79b |
| TAG-72 | ICOS | CD86 | CD8 |
| TAG-72 | ICOS | CD86 | CD3ζ |
| TAG-72 | ICOS | CD86 | CD3δ |
| TAG-72 | ICOS | CD86 | CD3γ |
| TAG-72 | ICOS | CD86 | CD3ε |
| TAG-72 | ICOS | CD86 | FcγRI-γ |
| TAG-72 | ICOS | CD86 | FcγRIII-γ |
| TAG-72 | ICOS | CD86 | FcεRIβ |
| TAG-72 | ICOS | CD86 | FcεRIγ |
| TAG-72 | ICOS | CD86 | DAP10 |
| TAG-72 | ICOS | CD86 | DAP12 |
| TAG-72 | ICOS | CD86 | CD32 |
| TAG-72 | ICOS | CD86 | CD79a |
| TAG-72 | ICOS | CD86 | CD79b |
| TAG-72 | ICOS | OX40 | CD8 |
| TAG-72 | ICOS | OX40 | CD3ζ |
| TAG-72 | ICOS | OX40 | CD3δ |
| TAG-72 | ICOS | OX40 | CD3γ |
| TAG-72 | ICOS | OX40 | CD3ε |
| TAG-72 | ICOS | OX40 | FcγRI-γ |
| TAG-72 | ICOS | OX40 | FcγRIII-γ |
| TAG-72 | ICOS | OX40 | FcεRIβ |
| TAG-72 | ICOS | OX40 | FcεRIγ |
| TAG-72 | ICOS | OX40 | DAP10 |
| TAG-72 | ICOS | OX40 | DAP12 |
| TAG-72 | ICOS | OX40 | CD32 |
| TAG-72 | ICOS | OX40 | CD79a |
| TAG-72 | ICOS | OX40 | CD79b |
| TAG-72 | ICOS | DAP10 | CD8 |
| TAG-72 | ICOS | DAP10 | CD3ζ |
| TAG-72 | ICOS | DAP10 | CD3δ |
| TAG-72 | ICOS | DAP10 | CD3γ |
| TAG-72 | ICOS | DAP10 | CD3ε |
| TAG-72 | ICOS | DAP10 | FcγRI-γ |

TABLE 3-continued

Third Generation CARs

| ScFv | Co-stimulatory Signal | Co-stimulatory Signal | Signal Domain |
|---|---|---|---|
| TAG-72 | ICOS | DAP10 | FcγRIII-γ |
| TAG-72 | ICOS | DAP10 | FcεRIβ |
| TAG-72 | ICOS | DAP10 | FcεRIγ |
| TAG-72 | ICOS | DAP10 | DAP10 |
| TAG-72 | ICOS | DAP10 | DAP12 |
| TAG-72 | ICOS | DAP10 | CD32 |
| TAG-72 | ICOS | DAP10 | CD79a |
| TAG-72 | ICOS | DAP10 | CD79b |
| TAG-72 | ICOS | DAP12 | CD8 |
| TAG-72 | ICOS | DAP12 | CD3ζ |
| TAG-72 | ICOS | DAP12 | CD3δ |
| TAG-72 | ICOS | DAP12 | CD3γ |
| TAG-72 | ICOS | DAP12 | CD3ε |
| TAG-72 | ICOS | DAP12 | FcγRI-γ |
| TAG-72 | ICOS | DAP12 | FcγRIII-γ |
| TAG-72 | ICOS | DAP12 | FcεRIβ |
| TAG-72 | ICOS | DAP12 | FcεRIγ |
| TAG-72 | ICOS | DAP12 | DAP10 |
| TAG-72 | ICOS | DAP12 | DAP12 |
| TAG-72 | ICOS | DAP12 | CD32 |
| TAG-72 | ICOS | DAP12 | CD79a |
| TAG-72 | ICOS | DAP12 | CD79b |
| TAG-72 | ICOS | MyD88 | CD8 |
| TAG-72 | ICOS | MyD88 | CD3ζ |
| TAG-72 | ICOS | MyD88 | CD3δ |
| TAG-72 | ICOS | MyD88 | CD3γ |
| TAG-72 | ICOS | MyD88 | CD3ε |
| TAG-72 | ICOS | MyD88 | FcγRI-γ |
| TAG-72 | ICOS | MyD88 | FcγRIII-γ |
| TAG-72 | ICOS | MyD88 | FcεRIβ |
| TAG-72 | ICOS | MyD88 | FcεRIγ |
| TAG-72 | ICOS | MyD88 | DAP10 |
| TAG-72 | ICOS | MyD88 | DAP12 |
| TAG-72 | ICOS | MyD88 | CD32 |
| TAG-72 | ICOS | MyD88 | CD79a |
| TAG-72 | ICOS | MyD88 | CD79b |
| TAG-72 | ICOS | CD7 | CD8 |
| TAG-72 | ICOS | CD7 | CD3ζ |
| TAG-72 | ICOS | CD7 | CD3δ |
| TAG-72 | ICOS | CD7 | CD3γ |
| TAG-72 | ICOS | CD7 | CD3ε |
| TAG-72 | ICOS | CD7 | FcγRI-γ |
| TAG-72 | ICOS | CD7 | FcγRIII-γ |
| TAG-72 | ICOS | CD7 | FcεRIβ |
| TAG-72 | ICOS | CD7 | FcεRIγ |
| TAG-72 | ICOS | CD7 | DAP10 |
| TAG-72 | ICOS | CD7 | DAP12 |
| TAG-72 | ICOS | CD7 | CD32 |
| TAG-72 | ICOS | CD7 | CD79a |
| TAG-72 | ICOS | CD7 | CD79b |
| TAG-72 | ICOS | BTNL3 | CD8 |
| TAG-72 | ICOS | BTNL3 | CD3ζ |
| TAG-72 | ICOS | BTNL3 | CD3δ |
| TAG-72 | ICOS | BTNL3 | CD3γ |
| TAG-72 | ICOS | BTNL3 | CD3ε |
| TAG-72 | ICOS | BTNL3 | FcγRI-γ |
| TAG-72 | ICOS | BTNL3 | FcγRIII-γ |
| TAG-72 | ICOS | BTNL3 | FcεRIβ |
| TAG-72 | ICOS | BTNL3 | FcεRIγ |
| TAG-72 | ICOS | BTNL3 | DAP10 |
| TAG-72 | ICOS | BTNL3 | DAP12 |
| TAG-72 | ICOS | BTNL3 | CD32 |
| TAG-72 | ICOS | BTNL3 | CD79a |
| TAG-72 | ICOS | BTNL3 | CD79b |
| TAG-72 | ICOS | NKG2D | CD8 |
| TAG-72 | ICOS | NKG2D | CD3ζ |
| TAG-72 | ICOS | NKG2D | CD3δ |
| TAG-72 | ICOS | NKG2D | CD3γ |
| TAG-72 | ICOS | NKG2D | CD3ε |
| TAG-72 | ICOS | NKG2D | FcγRI-γ |
| TAG-72 | ICOS | NKG2D | FcγRIII-γ |
| TAG-72 | ICOS | NKG2D | FcεRIβ |
| TAG-72 | ICOS | NKG2D | FcεRIγ |
| TAG-72 | ICOS | NKG2D | DAP10 |
| TAG-72 | ICOS | NKG2D | DAP12 |
| TAG-72 | ICOS | NKG2D | CD32 |
| TAG-72 | ICOS | NKG2D | CD79a |
| TAG-72 | ICOS | NKG2D | CD79b |
| TAG-72 | CD27 | CD28 | CD8 |
| TAG-72 | CD27 | CD28 | CD3ζ |
| TAG-72 | CD27 | CD28 | CD3δ |
| TAG-72 | CD27 | CD28 | CD3γ |
| TAG-72 | CD27 | CD28 | CD3ε |
| TAG-72 | CD27 | CD28 | FcγRI-γ |
| TAG-72 | CD27 | CD28 | FcγRIII-γ |
| TAG-72 | CD27 | CD28 | FcεRIβ |
| TAG-72 | CD27 | CD28 | FcεRIγ |
| TAG-72 | CD27 | CD28 | DAP10 |
| TAG-72 | CD27 | CD28 | DAP12 |
| TAG-72 | CD27 | CD28 | CD32 |
| TAG-72 | CD27 | CD28 | CD79a |
| TAG-72 | CD27 | CD28 | CD79b |
| TAG-72 | CD27 | CD8 | CD8 |
| TAG-72 | CD27 | CD8 | CD3ζ |
| TAG-72 | CD27 | CD8 | CD3δ |
| TAG-72 | CD27 | CD8 | CD3γ |
| TAG-72 | CD27 | CD8 | CD3ε |
| TAG-72 | CD27 | CD8 | FcγRI-γ |
| TAG-72 | CD27 | CD8 | FcγRIII-γ |
| TAG-72 | CD27 | CD8 | FcεRIβ |
| TAG-72 | CD27 | CD8 | FcεRIγ |
| TAG-72 | CD27 | CD8 | DAP10 |
| TAG-72 | CD27 | CD8 | DAP12 |
| TAG-72 | CD27 | CD8 | CD32 |
| TAG-72 | CD27 | CD8 | CD79a |
| TAG-72 | CD27 | CD8 | CD79b |
| TAG-72 | CD27 | CD4 | CD8 |
| TAG-72 | CD27 | CD4 | CD3ζ |
| TAG-72 | CD27 | CD4 | CD3δ |
| TAG-72 | CD27 | CD4 | CD3γ |
| TAG-72 | CD27 | CD4 | CD3ε |
| TAG-72 | CD27 | CD4 | FcγRI-γ |
| TAG-72 | CD27 | CD4 | FcγRIII-γ |
| TAG-72 | CD27 | CD4 | FcεRIβ |
| TAG-72 | CD27 | CD4 | FcεRIγ |
| TAG-72 | CD27 | CD4 | DAP10 |
| TAG-72 | CD27 | CD4 | DAP12 |
| TAG-72 | CD27 | CD4 | CD32 |
| TAG-72 | CD27 | CD4 | CD79a |
| TAG-72 | CD27 | CD4 | CD79b |
| TAG-72 | CD27 | b2c | CD8 |
| TAG-72 | CD27 | b2c | CD3ζ |
| TAG-72 | CD27 | b2c | CD3δ |
| TAG-72 | CD27 | b2c | CD3γ |
| TAG-72 | CD27 | b2c | CD3ε |
| TAG-72 | CD27 | b2c | FcγRI-γ |
| TAG-72 | CD27 | b2c | FcγRIII-γ |
| TAG-72 | CD27 | b2c | FcεRIβ |
| TAG-72 | CD27 | b2c | FcεRIγ |
| TAG-72 | CD27 | b2c | DAP10 |
| TAG-72 | CD27 | b2c | DAP12 |
| TAG-72 | CD27 | b2c | CD32 |
| TAG-72 | CD27 | b2c | CD79a |
| TAG-72 | CD27 | b2c | CD79b |
| TAG-72 | CD27 | CD137/41BB | CD8 |
| TAG-72 | CD27 | CD137/41BB | CD3ζ |
| TAG-72 | CD27 | CD137/41BB | CD3δ |
| TAG-72 | CD27 | CD137/41BB | CD3γ |
| TAG-72 | CD27 | CD137/41BB | CD3ε |
| TAG-72 | CD27 | CD137/41BB | FcγRI-γ |
| TAG-72 | CD27 | CD137/41BB | FcγRIII-γ |
| TAG-72 | CD27 | CD137/41BB | FcεRIβ |
| TAG-72 | CD27 | CD137/41BB | FcεRIγ |
| TAG-72 | CD27 | CD137/41BB | DAP10 |
| TAG-72 | CD27 | CD137/41BB | DAP12 |
| TAG-72 | CD27 | CD137/41BB | CD32 |
| TAG-72 | CD27 | CD137/41BB | CD79a |
| TAG-72 | CD27 | CD137/41BB | CD79b |
| TAG-72 | CD27 | ICOS | CD8 |
| TAG-72 | CD27 | ICOS | CD3ζ |

TABLE 3-continued

Third Generation CARs

| ScFv | Co-stimulatory Signal | Co-stimulatory Signal | Signal Domain |
|---|---|---|---|
| TAG-72 | CD27 | ICOS | CD3δ |
| TAG-72 | CD27 | ICOS | CD3γ |
| TAG-72 | CD27 | ICOS | CD3ε |
| TAG-72 | CD27 | ICOS | FcγRI-γ |
| TAG-72 | CD27 | ICOS | FcγRIII-γ |
| TAG-72 | CD27 | ICOS | FcεRIβ |
| TAG-72 | CD27 | ICOS | FcεRIγ |
| TAG-72 | CD27 | ICOS | DAP10 |
| TAG-72 | CD27 | ICOS | DAP12 |
| TAG-72 | CD27 | ICOS | CD32 |
| TAG-72 | CD27 | ICOS | CD79a |
| TAG-72 | CD27 | ICOS | CD79b |
| TAG-72 | CD27 | CD27 | CD8 |
| TAG-72 | CD27 | CD27 | CD3ζ |
| TAG-72 | CD27 | CD27 | CD3δ |
| TAG-72 | CD27 | CD27 | CD3γ |
| TAG-72 | CD27 | CD27 | CD3ε |
| TAG-72 | CD27 | CD27 | FcγRI-γ |
| TAG-72 | CD27 | CD27 | FcγRIII-γ |
| TAG-72 | CD27 | CD27 | FcεRIβ |
| TAG-72 | CD27 | CD27 | FcεRIγ |
| TAG-72 | CD27 | CD27 | DAP10 |
| TAG-72 | CD27 | CD27 | DAP12 |
| TAG-72 | CD27 | CD27 | CD32 |
| TAG-72 | CD27 | CD27 | CD79a |
| TAG-72 | CD27 | CD27 | CD79b |
| TAG-72 | CD27 | CD28δ | CD8 |
| TAG-72 | CD27 | CD28δ | CD3ζ |
| TAG-72 | CD27 | CD28δ | CD3δ |
| TAG-72 | CD27 | CD28δ | CD3γ |
| TAG-72 | CD27 | CD28δ | CD3ε |
| TAG-72 | CD27 | CD28δ | FcγRI-γ |
| TAG-72 | CD27 | CD28δ | FcγRIII-γ |
| TAG-72 | CD27 | CD28δ | FcεRIβ |
| TAG-72 | CD27 | CD28δ | FcεRIγ |
| TAG-72 | CD27 | CD28δ | DAP10 |
| TAG-72 | CD27 | CD28δ | DAP12 |
| TAG-72 | CD27 | CD28δ | CD32 |
| TAG-72 | CD27 | CD28δ | CD79a |
| TAG-72 | CD27 | CD28δ | CD79b |
| TAG-72 | CD27 | CD80 | CD8 |
| TAG-72 | CD27 | CD80 | CD3ζ |
| TAG-72 | CD27 | CD80 | CD3δ |
| TAG-72 | CD27 | CD80 | CD3γ |
| TAG-72 | CD27 | CD80 | CD3ε |
| TAG-72 | CD27 | CD80 | FcγRI-γ |
| TAG-72 | CD27 | CD80 | FcγRIII-γ |
| TAG-72 | CD27 | CD80 | FcεRIβ |
| TAG-72 | CD27 | CD80 | FcεRIγ |
| TAG-72 | CD27 | CD80 | DAP10 |
| TAG-72 | CD27 | CD80 | DAP12 |
| TAG-72 | CD27 | CD80 | CD32 |
| TAG-72 | CD27 | CD80 | CD79a |
| TAG-72 | CD27 | CD80 | CD79b |
| TAG-72 | CD27 | CD86 | CD8 |
| TAG-72 | CD27 | CD86 | CD3ζ |
| TAG-72 | CD27 | CD86 | CD3δ |
| TAG-72 | CD27 | CD86 | CD3γ |
| TAG-72 | CD27 | CD86 | CD3ε |
| TAG-72 | CD27 | CD86 | FcγRI-γ |
| TAG-72 | CD27 | CD86 | FcγRIII-γ |
| TAG-72 | CD27 | CD86 | FcεRIβ |
| TAG-72 | CD27 | CD86 | FcεRIγ |
| TAG-72 | CD27 | CD86 | DAP10 |
| TAG-72 | CD27 | CD86 | DAP12 |
| TAG-72 | CD27 | CD86 | CD32 |
| TAG-72 | CD27 | CD86 | CD79a |
| TAG-72 | CD27 | CD86 | CD79b |
| TAG-72 | CD27 | OX40 | CD8 |
| TAG-72 | CD27 | OX40 | CD3ζ |
| TAG-72 | CD27 | OX40 | CD3δ |
| TAG-72 | CD27 | OX40 | CD3γ |
| TAG-72 | CD27 | OX40 | CD3ε |
| TAG-72 | CD27 | OX40 | FcγRI-γ |
| TAG-72 | CD27 | OX40 | FcγRIII-γ |
| TAG-72 | CD27 | OX40 | FcεRIβ |
| TAG-72 | CD27 | OX40 | FcεRIγ |
| TAG-72 | CD27 | OX40 | DAP10 |
| TAG-72 | CD27 | OX40 | DAP12 |
| TAG-72 | CD27 | OX40 | CD32 |
| TAG-72 | CD27 | OX40 | CD79a |
| TAG-72 | CD27 | OX40 | CD79b |
| TAG-72 | CD27 | DAP10 | CD8 |
| TAG-72 | CD27 | DAP10 | CD3ζ |
| TAG-72 | CD27 | DAP10 | CD3δ |
| TAG-72 | CD27 | DAP10 | CD3γ |
| TAG-72 | CD27 | DAP10 | CD3ε |
| TAG-72 | CD27 | DAP10 | FcγRI-γ |
| TAG-72 | CD27 | DAP10 | FcγRIII-γ |
| TAG-72 | CD27 | DAP10 | FcεRIβ |
| TAG-72 | CD27 | DAP10 | FcεRIγ |
| TAG-72 | CD27 | DAP10 | DAP10 |
| TAG-72 | CD27 | DAP10 | DAP12 |
| TAG-72 | CD27 | DAP10 | CD32 |
| TAG-72 | CD27 | DAP10 | CD79a |
| TAG-72 | CD27 | DAP10 | CD79b |
| TAG-72 | CD27 | DAP12 | CD8 |
| TAG-72 | CD27 | DAP12 | CD3ζ |
| TAG-72 | CD27 | DAP12 | CD3δ |
| TAG-72 | CD27 | DAP12 | CD3γ |
| TAG-72 | CD27 | DAP12 | CD3ε |
| TAG-72 | CD27 | DAP12 | FcγRI-γ |
| TAG-72 | CD27 | DAP12 | FcγRIII-γ |
| TAG-72 | CD27 | DAP12 | FcεRIβ |
| TAG-72 | CD27 | DAP12 | FcεRIγ |
| TAG-72 | CD27 | DAP12 | DAP10 |
| TAG-72 | CD27 | DAP12 | DAP12 |
| TAG-72 | CD27 | DAP12 | CD32 |
| TAG-72 | CD27 | DAP12 | CD79a |
| TAG-72 | CD27 | DAP12 | CD79b |
| TAG-72 | CD27 | MyD88 | CD8 |
| TAG-72 | CD27 | MyD88 | CD3ζ |
| TAG-72 | CD27 | MyD88 | CD3δ |
| TAG-72 | CD27 | MyD88 | CD3γ |
| TAG-72 | CD27 | MyD88 | CD3ε |
| TAG-72 | CD27 | MyD88 | FcγRI-γ |
| TAG-72 | CD27 | MyD88 | FcγRIII-γ |
| TAG-72 | CD27 | MyD88 | FcεRIβ |
| TAG-72 | CD27 | MyD88 | FcεRIγ |
| TAG-72 | CD27 | MyD88 | DAP10 |
| TAG-72 | CD27 | MyD88 | DAP12 |
| TAG-72 | CD27 | MyD88 | CD32 |
| TAG-72 | CD27 | MyD88 | CD79a |
| TAG-72 | CD27 | MyD88 | CD79b |
| TAG-72 | CD27 | CD7 | CD8 |
| TAG-72 | CD27 | CD7 | CD3ζ |
| TAG-72 | CD27 | CD7 | CD3δ |
| TAG-72 | CD27 | CD7 | CD3γ |
| TAG-72 | CD27 | CD7 | CD3ε |
| TAG-72 | CD27 | CD7 | FcγRI-γ |
| TAG-72 | CD27 | CD7 | FcγRIII-γ |
| TAG-72 | CD27 | CD7 | FcεRIβ |
| TAG-72 | CD27 | CD7 | FcεRIγ |
| TAG-72 | CD27 | CD7 | DAP10 |
| TAG-72 | CD27 | CD7 | DAP12 |
| TAG-72 | CD27 | CD7 | CD32 |
| TAG-72 | CD27 | CD7 | CD79a |
| TAG-72 | CD27 | CD7 | CD79b |
| TAG-72 | CD27 | BTNL3 | CD8 |
| TAG-72 | CD27 | BTNL3 | CD3ζ |
| TAG-72 | CD27 | BTNL3 | CD3δ |
| TAG-72 | CD27 | BTNL3 | CD3γ |
| TAG-72 | CD27 | BTNL3 | CD3ε |
| TAG-72 | CD27 | BTNL3 | FcγRI-γ |
| TAG-72 | CD27 | BTNL3 | FcγRIII-γ |
| TAG-72 | CD27 | BTNL3 | FcεRIβ |
| TAG-72 | CD27 | BTNL3 | FcεRIγ |
| TAG-72 | CD27 | BTNL3 | DAP10 |
| TAG-72 | CD27 | BTNL3 | DAP12 |
| TAG-72 | CD27 | BTNL3 | CD32 |

TABLE 3-continued

Third Generation CARs

| ScFv | Co-stimulatory Signal | Co-stimulatory Signal | Signal Domain |
|---|---|---|---|
| TAG-72 | CD27 | BTNL3 | CD79a |
| TAG-72 | CD27 | BTNL3 | CD79b |
| TAG-72 | CD27 | NKG2D | CD8 |
| TAG-72 | CD27 | NKG2D | CD3ζ |
| TAG-72 | CD27 | NKG2D | CD3δ |
| TAG-72 | CD27 | NKG2D | CD3γ |
| TAG-72 | CD27 | NKG2D | CD3ε |
| TAG-72 | CD27 | NKG2D | FcγRI-γ |
| TAG-72 | CD27 | NKG2D | FcγRIII-γ |
| TAG-72 | CD27 | NKG2D | FcεRIβ |
| TAG-72 | CD27 | NKG2D | FcεRIγ |
| TAG-72 | CD27 | NKG2D | DAP10 |
| TAG-72 | CD27 | NKG2D | DAP12 |
| TAG-72 | CD27 | NKG2D | CD32 |
| TAG-72 | CD27 | NKG2D | CD79a |
| TAG-72 | CD27 | NKG2D | CD79b |
| TAG-72 | CD28δ | CD28 | CD8 |
| TAG-72 | CD28δ | CD28 | CD3ζ |
| TAG-72 | CD28δ | CD28 | CD3δ |
| TAG-72 | CD28δ | CD28 | CD3γ |
| TAG-72 | CD28δ | CD28 | CD3ε |
| TAG-72 | CD28δ | CD28 | FcγRI-γ |
| TAG-72 | CD28δ | CD28 | FcγRIII-γ |
| TAG-72 | CD28δ | CD28 | FcεRIβ |
| TAG-72 | CD28δ | CD28 | FcεRIγ |
| TAG-72 | CD28δ | CD28 | DAP10 |
| TAG-72 | CD28δ | CD28 | DAP12 |
| TAG-72 | CD28δ | CD28 | CD32 |
| TAG-72 | CD28δ | CD28 | CD79a |
| TAG-72 | CD28δ | CD28 | CD79b |
| TAG-72 | CD28δ | CD8 | CD8 |
| TAG-72 | CD28δ | CD8 | CD3ζ |
| TAG-72 | CD28δ | CD8 | CD3δ |
| TAG-72 | CD28δ | CD8 | CD3γ |
| TAG-72 | CD28δ | CD8 | CD3ε |
| TAG-72 | CD28δ | CD8 | FcγRI-γ |
| TAG-72 | CD28δ | CD8 | FcγRIII-γ |
| TAG-72 | CD28δ | CD8 | FcεRIβ |
| TAG-72 | CD28δ | CD8 | FcεRIγ |
| TAG-72 | CD28δ | CD8 | DAP10 |
| TAG-72 | CD28δ | CD8 | DAP12 |
| TAG-72 | CD28δ | CD8 | CD32 |
| TAG-72 | CD28δ | CD8 | CD79a |
| TAG-72 | CD28δ | CD8 | CD79b |
| TAG-72 | CD28δ | CD4 | CD8 |
| TAG-72 | CD28δ | CD4 | CD3ζ |
| TAG-72 | CD28δ | CD4 | CD3δ |
| TAG-72 | CD28δ | CD4 | CD3γ |
| TAG-72 | CD28δ | CD4 | CD3ε |
| TAG-72 | CD28δ | CD4 | FcγRI-γ |
| TAG-72 | CD28δ | CD4 | FcγRIII-γ |
| TAG-72 | CD28δ | CD4 | FcεRIβ |
| TAG-72 | CD28δ | CD4 | FcεRIγ |
| TAG-72 | CD28δ | CD4 | DAP10 |
| TAG-72 | CD28δ | CD4 | DAP12 |
| TAG-72 | CD28δ | CD4 | CD32 |
| TAG-72 | CD28δ | CD4 | CD79a |
| TAG-72 | CD28δ | CD4 | CD79b |
| TAG-72 | CD28δ | b2c | CD8 |
| TAG-72 | CD28δ | b2c | CD3ζ |
| TAG-72 | CD28δ | b2c | CD3δ |
| TAG-72 | CD28δ | b2c | CD3γ |
| TAG-72 | CD28δ | b2c | CD3ε |
| TAG-72 | CD28δ | b2c | FcγRI-γ |
| TAG-72 | CD28δ | b2c | FcγRIII-γ |
| TAG-72 | CD28δ | b2c | FcεRIβ |
| TAG-72 | CD28δ | b2c | FcεRIγ |
| TAG-72 | CD28δ | b2c | DAP10 |
| TAG-72 | CD28δ | b2c | DAP12 |
| TAG-72 | CD28δ | b2c | CD32 |
| TAG-72 | CD28δ | b2c | CD79a |
| TAG-72 | CD28δ | b2c | CD79b |
| TAG-72 | CD28δ | CD137/41BB | CD8 |
| TAG-72 | CD28δ | CD137/41BB | CD3ζ |
| TAG-72 | CD28δ | CD137/41BB | CD3δ |
| TAG-72 | CD28δ | CD137/41BB | CD3γ |
| TAG-72 | CD28δ | CD137/41BB | CD3ε |
| TAG-72 | CD28δ | CD137/41BB | FcγRI-γ |
| TAG-72 | CD28δ | CD137/41BB | FcγRIII-γ |
| TAG-72 | CD28δ | CD137/41BB | FcεRIβ |
| TAG-72 | CD28δ | CD137/41BB | FcεRIγ |
| TAG-72 | CD28δ | CD137/41BB | DAP10 |
| TAG-72 | CD28δ | CD137/41BB | DAP12 |
| TAG-72 | CD28δ | CD137/41BB | CD32 |
| TAG-72 | CD28δ | CD137/41BB | CD79a |
| TAG-72 | CD28δ | CD137/41BB | CD79b |
| TAG-72 | CD28δ | ICOS | CD8 |
| TAG-72 | CD28δ | ICOS | CD3ζ |
| TAG-72 | CD28δ | ICOS | CD3δ |
| TAG-72 | CD28δ | ICOS | CD3ε |
| TAG-72 | CD28δ | ICOS | FcγRI-γ |
| TAG-72 | CD28δ | ICOS | FcγRIII-γ |
| TAG-72 | CD28δ | ICOS | FcεRIβ |
| TAG-72 | CD28δ | ICOS | FcεRIγ |
| TAG-72 | CD28δ | ICOS | DAP10 |
| TAG-72 | CD28δ | ICOS | DAP12 |
| TAG-72 | CD28δ | ICOS | CD32 |
| TAG-72 | CD28δ | ICOS | CD79a |
| TAG-72 | CD28δ | ICOS | CD79b |
| TAG-72 | CD28δ | CD27 | CD8 |
| TAG-72 | CD28δ | CD27 | CD3ζ |
| TAG-72 | CD28δ | CD27 | CD3δ |
| TAG-72 | CD28δ | CD27 | CD3γ |
| TAG-72 | CD28δ | CD27 | CD3ε |
| TAG-72 | CD28δ | CD27 | FcγRI-γ |
| TAG-72 | CD28δ | CD27 | FcγRIII-γ |
| TAG-72 | CD28δ | CD27 | FcεRIβ |
| TAG-72 | CD28δ | CD27 | FcεRIγ |
| TAG-72 | CD28δ | CD27 | DAP10 |
| TAG-72 | CD28δ | CD27 | DAP12 |
| TAG-72 | CD28δ | CD27 | CD32 |
| TAG-72 | CD28δ | CD27 | CD79a |
| TAG-72 | CD28δ | CD27 | CD79b |
| TAG-72 | CD28δ | CD28δ | CD8 |
| TAG-72 | CD28δ | CD28δ | CD3ζ |
| TAG-72 | CD28δ | CD28δ | CD3δ |
| TAG-72 | CD28δ | CD28δ | CD3γ |
| TAG-72 | CD28δ | CD28δ | CD3ε |
| TAG-72 | CD28δ | CD28δ | FcγRI-γ |
| TAG-72 | CD28δ | CD28δ | FcγRIII-γ |
| TAG-72 | CD28δ | CD28δ | FcεRIβ |
| TAG-72 | CD28δ | CD28δ | FcεRIγ |
| TAG-72 | CD28δ | CD28δ | DAP10 |
| TAG-72 | CD28δ | CD28δ | DAP12 |
| TAG-72 | CD28δ | CD28δ | CD32 |
| TAG-72 | CD28δ | CD28δ | CD79a |
| TAG-72 | CD28δ | CD28δ | CD79b |
| TAG-72 | CD28δ | CD80 | CD8 |
| TAG-72 | CD28δ | CD80 | CD3ζ |
| TAG-72 | CD28δ | CD80 | CD3δ |
| TAG-72 | CD28δ | CD80 | CD3γ |
| TAG-72 | CD28δ | CD80 | CD3ε |
| TAG-72 | CD28δ | CD80 | FcγRI-γ |
| TAG-72 | CD28δ | CD80 | FcγRIII-γ |
| TAG-72 | CD28δ | CD80 | FcεRIβ |
| TAG-72 | CD28δ | CD80 | FcεRIγ |
| TAG-72 | CD28δ | CD80 | DAP10 |
| TAG-72 | CD28δ | CD80 | DAP12 |
| TAG-72 | CD28δ | CD80 | CD32 |
| TAG-72 | CD28δ | CD80 | CD79a |
| TAG-72 | CD28δ | CD80 | CD79b |
| TAG-72 | CD28δ | CD86 | CD8 |
| TAG-72 | CD28δ | CD86 | CD3ζ |
| TAG-72 | CD28δ | CD86 | CD3δ |
| TAG-72 | CD28δ | CD86 | CD3γ |
| TAG-72 | CD28δ | CD86 | CD3ε |
| TAG-72 | CD28δ | CD86 | FcγRI-γ |
| TAG-72 | CD28δ | CD86 | FcγRIII-γ |
| TAG-72 | CD28δ | CD86 | FcεRIβ |

TABLE 3-continued

Third Generation CARs

| ScFv | Co-stimulatory Signal | Co-stimulatory Signal | Signal Domain |
|---|---|---|---|
| TAG-72 | CD28δ | CD86 | FcεRIγ |
| TAG-72 | CD28δ | CD86 | DAP10 |
| TAG-72 | CD28δ | CD86 | DAP12 |
| TAG-72 | CD28δ | CD86 | CD32 |
| TAG-72 | CD28δ | CD86 | CD79a |
| TAG-72 | CD28δ | CD86 | CD79b |
| TAG-72 | CD28δ | OX40 | CD8 |
| TAG-72 | CD28δ | OX40 | CD3ζ |
| TAG-72 | CD28δ | OX40 | CD3δ |
| TAG-72 | CD28δ | OX40 | CD3γ |
| TAG-72 | CD28δ | OX40 | CD3ε |
| TAG-72 | CD28δ | OX40 | FcγRI-γ |
| TAG-72 | CD28δ | OX40 | FcγRIII-γ |
| TAG-72 | CD28δ | OX40 | FcεRIβ |
| TAG-72 | CD28δ | OX40 | FcεRIγ |
| TAG-72 | CD28δ | OX40 | DAP10 |
| TAG-72 | CD28δ | OX40 | DAP12 |
| TAG-72 | CD28δ | OX40 | CD32 |
| TAG-72 | CD28δ | OX40 | CD79a |
| TAG-72 | CD28δ | OX40 | CD79b |
| TAG-72 | CD28δ | DAP10 | CD8 |
| TAG-72 | CD28δ | DAP10 | CD3ζ |
| TAG-72 | CD28δ | DAP10 | CD3δ |
| TAG-72 | CD28δ | DAP10 | CD3γ |
| TAG-72 | CD28δ | DAP10 | CD3ε |
| TAG-72 | CD28δ | DAP10 | FcγRI-γ |
| TAG-72 | CD28δ | DAP10 | FcγRIII-γ |
| TAG-72 | CD28δ | DAP10 | FcεRIβ |
| TAG-72 | CD28δ | DAP10 | FcεRIγ |
| TAG-72 | CD28δ | DAP10 | DAP10 |
| TAG-72 | CD28δ | DAP10 | DAP12 |
| TAG-72 | CD28δ | DAP10 | CD32 |
| TAG-72 | CD28δ | DAP10 | CD79a |
| TAG-72 | CD28δ | DAP10 | CD79b |
| TAG-72 | CD28δ | DAP12 | CD8 |
| TAG-72 | CD28δ | DAP12 | CD3ζ |
| TAG-72 | CD28δ | DAP12 | CD3δ |
| TAG-72 | CD28δ | DAP12 | CD3γ |
| TAG-72 | CD28δ | DAP12 | CD3ε |
| TAG-72 | CD28δ | DAP12 | FcγRI-γ |
| TAG-72 | CD28δ | DAP12 | FcγRIII-γ |
| TAG-72 | CD28δ | DAP12 | FcεRIβ |
| TAG-72 | CD28δ | DAP12 | FcεRIγ |
| TAG-72 | CD28δ | DAP12 | DAP10 |
| TAG-72 | CD28δ | DAP12 | DAP12 |
| TAG-72 | CD28δ | DAP12 | CD32 |
| TAG-72 | CD28δ | DAP12 | CD79a |
| TAG-72 | CD28δ | DAP12 | CD79b |
| TAG-72 | CD28δ | MyD88 | CD8 |
| TAG-72 | CD28δ | MyD88 | CD3ζ |
| TAG-72 | CD28δ | MyD88 | CD3δ |
| TAG-72 | CD28δ | MyD88 | CD3γ |
| TAG-72 | CD28δ | MyD88 | CD3ε |
| TAG-72 | CD28δ | MyD88 | FcγRI-γ |
| TAG-72 | CD28δ | MyD88 | FcγRIII-γ |
| TAG-72 | CD28δ | MyD88 | FcεRIβ |
| TAG-72 | CD28δ | MyD88 | FcεRIγ |
| TAG-72 | CD28δ | MyD88 | DAP10 |
| TAG-72 | CD28δ | MyD88 | DAP12 |
| TAG-72 | CD28δ | MyD88 | CD32 |
| TAG-72 | CD28δ | MyD88 | CD79a |
| TAG-72 | CD28δ | MyD88 | CD79b |
| TAG-72 | CD28δ | CD7 | CD8 |
| TAG-72 | CD28δ | CD7 | CD3ζ |
| TAG-72 | CD28δ | CD7 | CD3δ |
| TAG-72 | CD28δ | CD7 | CD3γ |
| TAG-72 | CD28δ | CD7 | CD3ε |
| TAG-72 | CD28δ | CD7 | FcγRI-γ |
| TAG-72 | CD28δ | CD7 | FcγRIII-γ |
| TAG-72 | CD28δ | CD7 | FcεRIβ |
| TAG-72 | CD28δ | CD7 | FcεRIγ |
| TAG-72 | CD28δ | CD7 | DAP10 |
| TAG-72 | CD28δ | CD7 | DAP12 |
| TAG-72 | CD28δ | CD7 | CD32 |
| TAG-72 | CD28δ | CD7 | CD79a |
| TAG-72 | CD28δ | CD7 | CD79b |
| TAG-72 | CD28δ | BTNL3 | CD8 |
| TAG-72 | CD28δ | BTNL3 | CD3ζ |
| TAG-72 | CD28δ | BTNL3 | CD3δ |
| TAG-72 | CD28δ | BTNL3 | CD3γ |
| TAG-72 | CD28δ | BTNL3 | CD3ε |
| TAG-72 | CD28δ | BTNL3 | FcγRI-γ |
| TAG-72 | CD28δ | BTNL3 | FcγRIII-γ |
| TAG-72 | CD28δ | BTNL3 | FcεRIβ |
| TAG-72 | CD28δ | BTNL3 | FcεRIγ |
| TAG-72 | CD28δ | BTNL3 | DAP10 |
| TAG-72 | CD28δ | BTNL3 | DAP12 |
| TAG-72 | CD28δ | BTNL3 | CD32 |
| TAG-72 | CD28δ | BTNL3 | CD79a |
| TAG-72 | CD28δ | BTNL3 | CD79b |
| TAG-72 | CD28δ | NKG2D | CD8 |
| TAG-72 | CD28δ | NKG2D | CD3ζ |
| TAG-72 | CD28δ | NKG2D | CD3δ |
| TAG-72 | CD28δ | NKG2D | CD3γ |
| TAG-72 | CD28δ | NKG2D | CD3ε |
| TAG-72 | CD28δ | NKG2D | FcγRI-γ |
| TAG-72 | CD28δ | NKG2D | FcγRIII-γ |
| TAG-72 | CD28δ | NKG2D | FcεRIβ |
| TAG-72 | CD28δ | NKG2D | FcεRIγ |
| TAG-72 | CD28δ | NKG2D | DAP10 |
| TAG-72 | CD28δ | NKG2D | DAP12 |
| TAG-72 | CD28δ | NKG2D | CD32 |
| TAG-72 | CD28δ | NKG2D | CD79a |
| TAG-72 | CD28δ | NKG2D | CD79b |
| TAG-72 | CD80 | CD28 | CD8 |
| TAG-72 | CD80 | CD28 | CD3ζ |
| TAG-72 | CD80 | CD28 | CD3δ |
| TAG-72 | CD80 | CD28 | CD3γ |
| TAG-72 | CD80 | CD28 | CD3ε |
| TAG-72 | CD80 | CD28 | FcγRI-γ |
| TAG-72 | CD80 | CD28 | FcγRIII-γ |
| TAG-72 | CD80 | CD28 | FcεRIβ |
| TAG-72 | CD80 | CD28 | FcεRIγ |
| TAG-72 | CD80 | CD28 | DAP10 |
| TAG-72 | CD80 | CD28 | DAP12 |
| TAG-72 | CD80 | CD28 | CD32 |
| TAG-72 | CD80 | CD28 | CD79a |
| TAG-72 | CD80 | CD28 | CD79b |
| TAG-72 | CD80 | CD8 | CD8 |
| TAG-72 | CD80 | CD8 | CD3ζ |
| TAG-72 | CD80 | CD8 | CD3δ |
| TAG-72 | CD80 | CD8 | CD3γ |
| TAG-72 | CD80 | CD8 | CD3ε |
| TAG-72 | CD80 | CD8 | FcγRI-γ |
| TAG-72 | CD80 | CD8 | FcγRIII-γ |
| TAG-72 | CD80 | CD8 | FcεRIβ |
| TAG-72 | CD80 | CD8 | FcεRIγ |
| TAG-72 | CD80 | CD8 | DAP10 |
| TAG-72 | CD80 | CD8 | DAP12 |
| TAG-72 | CD80 | CD8 | CD32 |
| TAG-72 | CD80 | CD8 | CD79a |
| TAG-72 | CD80 | CD8 | CD79b |
| TAG-72 | CD80 | CD4 | CD8 |
| TAG-72 | CD80 | CD4 | CD3ζ |
| TAG-72 | CD80 | CD4 | CD3δ |
| TAG-72 | CD80 | CD4 | CD3γ |
| TAG-72 | CD80 | CD4 | CD3ε |
| TAG-72 | CD80 | CD4 | FcγRI-γ |
| TAG-72 | CD80 | CD4 | FcγRIII-γ |
| TAG-72 | CD80 | CD4 | FcεRIβ |
| TAG-72 | CD80 | CD4 | FcεRIγ |
| TAG-72 | CD80 | CD4 | DAP10 |
| TAG-72 | CD80 | CD4 | DAP12 |
| TAG-72 | CD80 | CD4 | CD32 |
| TAG-72 | CD80 | CD4 | CD79a |
| TAG-72 | CD80 | CD4 | CD79b |
| TAG-72 | CD80 | b2c | CD8 |
| TAG-72 | CD80 | b2c | CD3ζ |
| TAG-72 | CD80 | b2c | CD3δ |
| TAG-72 | CD80 | b2c | CD3γ |

TABLE 3-continued

Third Generation CARs

| ScFv | Co-stimulatory Signal | Co-stimulatory Signal | Signal Domain |
|---|---|---|---|
| TAG-72 | CD80 | b2c | CD3ε |
| TAG-72 | CD80 | b2c | FcγRI-γ |
| TAG-72 | CD80 | b2c | FcγRIII-γ |
| TAG-72 | CD80 | b2c | FcεRIβ |
| TAG-72 | CD80 | b2c | FcεRIγ |
| TAG-72 | CD80 | b2c | DAP10 |
| TAG-72 | CD80 | b2c | DAP12 |
| TAG-72 | CD80 | b2c | CD32 |
| TAG-72 | CD80 | b2c | CD79a |
| TAG-72 | CD80 | b2c | CD79b |
| TAG-72 | CD80 | CD137/41BB | CD8 |
| TAG-72 | CD80 | CD137/41BB | CD3ζ |
| TAG-72 | CD80 | CD137/41BB | CD3δ |
| TAG-72 | CD80 | CD137/41BB | CD3γ |
| TAG-72 | CD80 | CD137/41BB | CD3ε |
| TAG-72 | CD80 | CD137/41BB | FcγRI-γ |
| TAG-72 | CD80 | CD137/41BB | FcγRIII-γ |
| TAG-72 | CD80 | CD137/41BB | FcεRIβ |
| TAG-72 | CD80 | CD137/41BB | FcεRIγ |
| TAG-72 | CD80 | CD137/41BB | DAP10 |
| TAG-72 | CD80 | CD137/41BB | DAP12 |
| TAG-72 | CD80 | CD137/41BB | CD32 |
| TAG-72 | CD80 | CD137/41BB | CD79a |
| TAG-72 | CD80 | CD137/41BB | CD79b |
| TAG-72 | CD80 | ICOS | CD8 |
| TAG-72 | CD80 | ICOS | CD3ζ |
| TAG-72 | CD80 | ICOS | CD3δ |
| TAG-72 | CD80 | ICOS | CD3γ |
| TAG-72 | CD80 | ICOS | CD3ε |
| TAG-72 | CD80 | ICOS | FcγRI-γ |
| TAG-72 | CD80 | ICOS | FcγRIII-γ |
| TAG-72 | CD80 | ICOS | FcεRIβ |
| TAG-72 | CD80 | ICOS | FcεRIγ |
| TAG-72 | CD80 | ICOS | DAP10 |
| TAG-72 | CD80 | ICOS | DAP12 |
| TAG-72 | CD80 | ICOS | CD32 |
| TAG-72 | CD80 | ICOS | CD79a |
| TAG-72 | CD80 | ICOS | CD79b |
| TAG-72 | CD80 | CD27 | CD8 |
| TAG-72 | CD80 | CD27 | CD3ζ |
| TAG-72 | CD80 | CD27 | CD3δ |
| TAG-72 | CD80 | CD27 | CD3γ |
| TAG-72 | CD80 | CD27 | CD3ε |
| TAG-72 | CD80 | CD27 | FcγRI-γ |
| TAG-72 | CD80 | CD27 | FcγRIII-γ |
| TAG-72 | CD80 | CD27 | FcεRIβ |
| TAG-72 | CD80 | CD27 | FcεRIγ |
| TAG-72 | CD80 | CD27 | DAP10 |
| TAG-72 | CD80 | CD27 | DAP12 |
| TAG-72 | CD80 | CD27 | CD32 |
| TAG-72 | CD80 | CD27 | CD79a |
| TAG-72 | CD80 | CD27 | CD79b |
| TAG-72 | CD80 | CD28δ | CD8 |
| TAG-72 | CD80 | CD28δ | CD3ζ |
| TAG-72 | CD80 | CD28δ | CD3δ |
| TAG-72 | CD80 | CD28δ | CD3γ |
| TAG-72 | CD80 | CD28δ | CD3ε |
| TAG-72 | CD80 | CD28δ | FcγRI-γ |
| TAG-72 | CD80 | CD28δ | FcγRIII-γ |
| TAG-72 | CD80 | CD28δ | FcεRIβ |
| TAG-72 | CD80 | CD28δ | FcεRIγ |
| TAG-72 | CD80 | CD28δ | DAP10 |
| TAG-72 | CD80 | CD28δ | DAP12 |
| TAG-72 | CD80 | CD28δ | CD32 |
| TAG-72 | CD80 | CD28δ | CD79a |
| TAG-72 | CD80 | CD28δ | CD79b |
| TAG-72 | CD80 | CD80 | CD8 |
| TAG-72 | CD80 | CD80 | CD3ζ |
| TAG-72 | CD80 | CD80 | CD3δ |
| TAG-72 | CD80 | CD80 | CD3γ |
| TAG-72 | CD80 | CD80 | CD3ε |
| TAG-72 | CD80 | CD80 | FcγRI-γ |
| TAG-72 | CD80 | CD80 | FcγRIII-γ |
| TAG-72 | CD80 | CD80 | FcεRIβ |
| TAG-72 | CD80 | CD80 | FcεRIγ |
| TAG-72 | CD80 | CD80 | DAP10 |
| TAG-72 | CD80 | CD80 | DAP12 |
| TAG-72 | CD80 | CD80 | CD32 |
| TAG-72 | CD80 | CD80 | CD79a |
| TAG-72 | CD80 | CD80 | CD79b |
| TAG-72 | CD80 | CD86 | CD8 |
| TAG-72 | CD80 | CD86 | CD3ζ |
| TAG-72 | CD80 | CD86 | CD3δ |
| TAG-72 | CD80 | CD86 | CD3γ |
| TAG-72 | CD80 | CD86 | CD3ε |
| TAG-72 | CD80 | CD86 | FcγRI-γ |
| TAG-72 | CD80 | CD86 | FcγRIII-γ |
| TAG-72 | CD80 | CD86 | FcεRIβ |
| TAG-72 | CD80 | CD86 | FcεRIγ |
| TAG-72 | CD80 | CD86 | DAP10 |
| TAG-72 | CD80 | CD86 | DAP12 |
| TAG-72 | CD80 | CD86 | CD32 |
| TAG-72 | CD80 | CD86 | CD79a |
| TAG-72 | CD80 | CD86 | CD79b |
| TAG-72 | CD80 | OX40 | CD8 |
| TAG-72 | CD80 | OX40 | CD3ζ |
| TAG-72 | CD80 | OX40 | CD3δ |
| TAG-72 | CD80 | OX40 | CD3γ |
| TAG-72 | CD80 | OX40 | CD3ε |
| TAG-72 | CD80 | OX40 | FcγRI-γ |
| TAG-72 | CD80 | OX40 | FcγRIII-γ |
| TAG-72 | CD80 | OX40 | FcεRIβ |
| TAG-72 | CD80 | OX40 | FcεRIγ |
| TAG-72 | CD80 | OX40 | DAP10 |
| TAG-72 | CD80 | OX40 | DAP12 |
| TAG-72 | CD80 | OX40 | CD32 |
| TAG-72 | CD80 | OX40 | CD79a |
| TAG-72 | CD80 | OX40 | CD79b |
| TAG-72 | CD80 | DAP10 | CD8 |
| TAG-72 | CD80 | DAP10 | CD3ζ |
| TAG-72 | CD80 | DAP10 | CD3δ |
| TAG-72 | CD80 | DAP10 | CD3γ |
| TAG-72 | CD80 | DAP10 | CD3ε |
| TAG-72 | CD80 | DAP10 | FcγRI-γ |
| TAG-72 | CD80 | DAP10 | FcγRIII-γ |
| TAG-72 | CD80 | DAP10 | FcεRIβ |
| TAG-72 | CD80 | DAP10 | FcεRIγ |
| TAG-72 | CD80 | DAP10 | DAP10 |
| TAG-72 | CD80 | DAP10 | DAP12 |
| TAG-72 | CD80 | DAP10 | CD32 |
| TAG-72 | CD80 | DAP10 | CD79a |
| TAG-72 | CD80 | DAP10 | CD79b |
| TAG-72 | CD80 | DAP12 | CD8 |
| TAG-72 | CD80 | DAP12 | CD3ζ |
| TAG-72 | CD80 | DAP12 | CD3δ |
| TAG-72 | CD80 | DAP12 | CD3γ |
| TAG-72 | CD80 | DAP12 | CD3ε |
| TAG-72 | CD80 | DAP12 | FcγRI-γ |
| TAG-72 | CD80 | DAP12 | FcγRIII-γ |
| TAG-72 | CD80 | DAP12 | FcεRIβ |
| TAG-72 | CD80 | DAP12 | FcεRIγ |
| TAG-72 | CD80 | DAP12 | DAP10 |
| TAG-72 | CD80 | DAP12 | DAP12 |
| TAG-72 | CD80 | DAP12 | CD32 |
| TAG-72 | CD80 | DAP12 | CD79a |
| TAG-72 | CD80 | DAP12 | CD79b |
| TAG-72 | CD80 | MyD88 | CD8 |
| TAG-72 | CD80 | MyD88 | CD3ζ |
| TAG-72 | CD80 | MyD88 | CD3δ |
| TAG-72 | CD80 | MyD88 | CD3γ |
| TAG-72 | CD80 | MyD88 | CD3ε |
| TAG-72 | CD80 | MyD88 | FcγRI-γ |
| TAG-72 | CD80 | MyD88 | FcγRIII-γ |
| TAG-72 | CD80 | MyD88 | FcεRIβ |
| TAG-72 | CD80 | MyD88 | FcεRIγ |
| TAG-72 | CD80 | MyD88 | DAP10 |
| TAG-72 | CD80 | MyD88 | DAP12 |
| TAG-72 | CD80 | MyD88 | CD32 |
| TAG-72 | CD80 | MyD88 | CD79a |
| TAG-72 | CD80 | MyD88 | CD79b |

TABLE 3-continued

Third Generation CARs

| ScFv | Co-stimulatory Signal | Co-stimulatory Signal | Signal Domain |
|---|---|---|---|
| TAG-72 | CD80 | CD7 | CD8 |
| TAG-72 | CD80 | CD7 | CD3ζ |
| TAG-72 | CD80 | CD7 | CD3δ |
| TAG-72 | CD80 | CD7 | CD3γ |
| TAG-72 | CD80 | CD7 | CD3ε |
| TAG-72 | CD80 | CD7 | FcγRI-γ |
| TAG-72 | CD80 | CD7 | FcγRIII-γ |
| TAG-72 | CD80 | CD7 | FcεRIβ |
| TAG-72 | CD80 | CD7 | FcεRIγ |
| TAG-72 | CD80 | CD7 | DAP10 |
| TAG-72 | CD80 | CD7 | DAP12 |
| TAG-72 | CD80 | CD7 | CD32 |
| TAG-72 | CD80 | CD7 | CD79a |
| TAG-72 | CD80 | CD7 | CD79b |
| TAG-72 | CD80 | BTNL3 | CD8 |
| TAG-72 | CD80 | BTNL3 | CD3ζ |
| TAG-72 | CD80 | BTNL3 | CD3δ |
| TAG-72 | CD80 | BTNL3 | CD3γ |
| TAG-72 | CD80 | BTNL3 | CD3ε |
| TAG-72 | CD80 | BTNL3 | FcγRI-γ |
| TAG-72 | CD80 | BTNL3 | FcγRIII-γ |
| TAG-72 | CD80 | BTNL3 | FcεRIβ |
| TAG-72 | CD80 | BTNL3 | FcεRIγ |
| TAG-72 | CD80 | BTNL3 | DAP10 |
| TAG-72 | CD80 | BTNL3 | DAP12 |
| TAG-72 | CD80 | BTNL3 | CD32 |
| TAG-72 | CD80 | BTNL3 | CD79a |
| TAG-72 | CD80 | BTNL3 | CD79b |
| TAG-72 | CD80 | NKG2D | CD8 |
| TAG-72 | CD80 | NKG2D | CD3ζ |
| TAG-72 | CD80 | NKG2D | CD3δ |
| TAG-72 | CD80 | NKG2D | CD3γ |
| TAG-72 | CD80 | NKG2D | CD3ε |
| TAG-72 | CD80 | NKG2D | FcγRI-γ |
| TAG-72 | CD80 | NKG2D | FcγRIII-γ |
| TAG-72 | CD80 | NKG2D | FcεRIβ |
| TAG-72 | CD80 | NKG2D | FcεRIγ |
| TAG-72 | CD80 | NKG2D | DAP10 |
| TAG-72 | CD80 | NKG2D | DAP12 |
| TAG-72 | CD80 | NKG2D | CD32 |
| TAG-72 | CD80 | NKG2D | CD79a |
| TAG-72 | CD80 | NKG2D | CD79b |
| TAG-72 | CD86 | CD28 | CD8 |
| TAG-72 | CD86 | CD28 | CD3ζ |
| TAG-72 | CD86 | CD28 | CD3δ |
| TAG-72 | CD86 | CD28 | CD3γ |
| TAG-72 | CD86 | CD28 | CD3ε |
| TAG-72 | CD86 | CD28 | FcγRI-γ |
| TAG-72 | CD86 | CD28 | FcγRIII-γ |
| TAG-72 | CD86 | CD28 | FcεRIβ |
| TAG-72 | CD86 | CD28 | FcεRIγ |
| TAG-72 | CD86 | CD28 | DAP10 |
| TAG-72 | CD86 | CD28 | DAP12 |
| TAG-72 | CD86 | CD28 | CD32 |
| TAG-72 | CD86 | CD28 | CD79a |
| TAG-72 | CD86 | CD28 | CD79b |
| TAG-72 | CD86 | CD8 | CD8 |
| TAG-72 | CD86 | CD8 | CD3ζ |
| TAG-72 | CD86 | CD8 | CD3δ |
| TAG-72 | CD86 | CD8 | CD3γ |
| TAG-72 | CD86 | CD8 | CD3ε |
| TAG-72 | CD86 | CD8 | FcγRI-γ |
| TAG-72 | CD86 | CD8 | FcγRIII-γ |
| TAG-72 | CD86 | CD8 | FcεRIβ |
| TAG-72 | CD86 | CD8 | FcεRIγ |
| TAG-72 | CD86 | CD8 | DAP10 |
| TAG-72 | CD86 | CD8 | DAP12 |
| TAG-72 | CD86 | CD8 | CD32 |
| TAG-72 | CD86 | CD8 | CD79a |
| TAG-72 | CD86 | CD8 | CD79b |
| TAG-72 | CD86 | CD4 | CD8 |
| TAG-72 | CD86 | CD4 | CD3ζ |
| TAG-72 | CD86 | CD4 | CD3δ |
| TAG-72 | CD86 | CD4 | CD3γ |
| TAG-72 | CD86 | CD4 | CD3ε |
| TAG-72 | CD86 | CD4 | FcγRI-γ |
| TAG-72 | CD86 | CD4 | FcγRIII-γ |
| TAG-72 | CD86 | CD4 | FcεRIβ |
| TAG-72 | CD86 | CD4 | FcεRIγ |
| TAG-72 | CD86 | CD4 | DAP10 |
| TAG-72 | CD86 | CD4 | DAP12 |
| TAG-72 | CD86 | CD4 | CD32 |
| TAG-72 | CD86 | CD4 | CD79a |
| TAG-72 | CD86 | CD4 | CD79b |
| TAG-72 | CD86 | b2c | CD8 |
| TAG-72 | CD86 | b2c | CD3ζ |
| TAG-72 | CD86 | b2c | CD3δ |
| TAG-72 | CD86 | b2c | CD3γ |
| TAG-72 | CD86 | b2c | CD3ε |
| TAG-72 | CD86 | b2c | FcγRI-γ |
| TAG-72 | CD86 | b2c | FcγRIII-γ |
| TAG-72 | CD86 | b2c | FcεRIβ |
| TAG-72 | CD86 | b2c | FcεRIγ |
| TAG-72 | CD86 | b2c | DAP10 |
| TAG-72 | CD86 | b2c | DAP12 |
| TAG-72 | CD86 | b2c | CD32 |
| TAG-72 | CD86 | b2c | CD79a |
| TAG-72 | CD86 | b2c | CD79b |
| TAG-72 | CD86 | CD137/41BB | CD8 |
| TAG-72 | CD86 | CD137/41BB | CD3ζ |
| TAG-72 | CD86 | CD137/41BB | CD3δ |
| TAG-72 | CD86 | CD137/41BB | CD3γ |
| TAG-72 | CD86 | CD137/41BB | CD3ε |
| TAG-72 | CD86 | CD137/41BB | FcγRI-γ |
| TAG-72 | CD86 | CD137/41BB | FcγRIII-γ |
| TAG-72 | CD86 | CD137/41BB | FcεRIβ |
| TAG-72 | CD86 | CD137/41BB | FcεRIγ |
| TAG-72 | CD86 | CD137/41BB | DAP10 |
| TAG-72 | CD86 | CD137/41BB | DAP12 |
| TAG-72 | CD86 | CD137/41BB | CD32 |
| TAG-72 | CD86 | CD137/41BB | CD79a |
| TAG-72 | CD86 | CD137/41BB | CD79b |
| TAG-72 | CD86 | ICOS | CD8 |
| TAG-72 | CD86 | ICOS | CD3ζ |
| TAG-72 | CD86 | ICOS | CD3δ |
| TAG-72 | CD86 | ICOS | CD3γ |
| TAG-72 | CD86 | ICOS | CD3ε |
| TAG-72 | CD86 | ICOS | FcγRI-γ |
| TAG-72 | CD86 | ICOS | FcγRIII-γ |
| TAG-72 | CD86 | ICOS | FcεRIβ |
| TAG-72 | CD86 | ICOS | FcεRIγ |
| TAG-72 | CD86 | ICOS | DAP10 |
| TAG-72 | CD86 | ICOS | DAP12 |
| TAG-72 | CD86 | ICOS | CD32 |
| TAG-72 | CD86 | ICOS | CD79a |
| TAG-72 | CD86 | ICOS | CD79b |
| TAG-72 | CD86 | CD27 | CD8 |
| TAG-72 | CD86 | CD27 | CD3ζ |
| TAG-72 | CD86 | CD27 | CD3δ |
| TAG-72 | CD86 | CD27 | CD3γ |
| TAG-72 | CD86 | CD27 | CD3ε |
| TAG-72 | CD86 | CD27 | FcγRI-γ |
| TAG-72 | CD86 | CD27 | FcγRIII-γ |
| TAG-72 | CD86 | CD27 | FcεRIβ |
| TAG-72 | CD86 | CD27 | FcεRIγ |
| TAG-72 | CD86 | CD27 | DAP10 |
| TAG-72 | CD86 | CD27 | DAP12 |
| TAG-72 | CD86 | CD27 | CD32 |
| TAG-72 | CD86 | CD27 | CD79a |
| TAG-72 | CD86 | CD27 | CD79b |
| TAG-72 | CD86 | CD28δ | CD8 |
| TAG-72 | CD86 | CD28δ | CD3ζ |
| TAG-72 | CD86 | CD28δ | CD3δ |
| TAG-72 | CD86 | CD28δ | CD3γ |
| TAG-72 | CD86 | CD28δ | CD3ε |
| TAG-72 | CD86 | CD28δ | FcγRI-γ |
| TAG-72 | CD86 | CD28δ | FcγRIII-γ |
| TAG-72 | CD86 | CD28δ | FcεRIβ |
| TAG-72 | CD86 | CD28δ | FcεRIγ |
| TAG-72 | CD86 | CD28δ | DAP10 |

TABLE 3-continued

Third Generation CARs

| ScFv | Co-stimulatory Signal | Co-stimulatory Signal | Signal Domain |
|---|---|---|---|
| TAG-72 | CD86 | CD28δ | DAP12 |
| TAG-72 | CD86 | CD28δ | CD32 |
| TAG-72 | CD86 | CD28δ | CD79a |
| TAG-72 | CD86 | CD28δ | CD79b |
| TAG-72 | CD86 | CD80 | CD8 |
| TAG-72 | CD86 | CD80 | CD3ζ |
| TAG-72 | CD86 | CD80 | CD3δ |
| TAG-72 | CD86 | CD80 | CD3γ |
| TAG-72 | CD86 | CD80 | CD3ε |
| TAG-72 | CD86 | CD80 | FcγRI-γ |
| TAG-72 | CD86 | CD80 | FcγRIII-γ |
| TAG-72 | CD86 | CD80 | FcεRIβ |
| TAG-72 | CD86 | CD80 | FcεRIγ |
| TAG-72 | CD86 | CD80 | DAP10 |
| TAG-72 | CD86 | CD80 | DAP12 |
| TAG-72 | CD86 | CD80 | CD32 |
| TAG-72 | CD86 | CD80 | CD79a |
| TAG-72 | CD86 | CD80 | CD79b |
| TAG-72 | CD86 | CD86 | CD8 |
| TAG-72 | CD86 | CD86 | CD3ζ |
| TAG-72 | CD86 | CD86 | CD3δ |
| TAG-72 | CD86 | CD86 | CD3γ |
| TAG-72 | CD86 | CD86 | CD3ε |
| TAG-72 | CD86 | CD86 | FcγRI-γ |
| TAG-72 | CD86 | CD86 | FcγRIII-γ |
| TAG-72 | CD86 | CD86 | FcεRIβ |
| TAG-72 | CD86 | CD86 | FcεRIγ |
| TAG-72 | CD86 | CD86 | DAP10 |
| TAG-72 | CD86 | CD86 | DAP12 |
| TAG-72 | CD86 | CD86 | CD32 |
| TAG-72 | CD86 | CD86 | CD79a |
| TAG-72 | CD86 | CD86 | CD79b |
| TAG-72 | CD86 | OX40 | CD8 |
| TAG-72 | CD86 | OX40 | CD3ζ |
| TAG-72 | CD86 | OX40 | CD3δ |
| TAG-72 | CD86 | OX40 | CD3γ |
| TAG-72 | CD86 | OX40 | CD3ε |
| TAG-72 | CD86 | OX40 | FcγRI-γ |
| TAG-72 | CD86 | OX40 | FcγRIII-γ |
| TAG-72 | CD86 | OX40 | FcεRIβ |
| TAG-72 | CD86 | OX40 | FcεRIγ |
| TAG-72 | CD86 | OX40 | DAP10 |
| TAG-72 | CD86 | OX40 | DAP12 |
| TAG-72 | CD86 | OX40 | CD32 |
| TAG-72 | CD86 | OX40 | CD79a |
| TAG-72 | CD86 | OX40 | CD79b |
| TAG-72 | CD86 | DAP10 | CD8 |
| TAG-72 | CD86 | DAP10 | CD3ζ |
| TAG-72 | CD86 | DAP10 | CD3δ |
| TAG-72 | CD86 | DAP10 | CD3γ |
| TAG-72 | CD86 | DAP10 | CD3ε |
| TAG-72 | CD86 | DAP10 | FcγRI-γ |
| TAG-72 | CD86 | DAP10 | FcγRIII-γ |
| TAG-72 | CD86 | DAP10 | FcεRIβ |
| TAG-72 | CD86 | DAP10 | FcεRIγ |
| TAG-72 | CD86 | DAP10 | DAP10 |
| TAG-72 | CD86 | DAP10 | DAP12 |
| TAG-72 | CD86 | DAP10 | CD32 |
| TAG-72 | CD86 | DAP10 | CD79a |
| TAG-72 | CD86 | DAP10 | CD79b |
| TAG-72 | CD86 | DAP12 | CD8 |
| TAG-72 | CD86 | DAP12 | CD3ζ |
| TAG-72 | CD86 | DAP12 | CD3δ |
| TAG-72 | CD86 | DAP12 | CD3γ |
| TAG-72 | CD86 | DAP12 | CD3ε |
| TAG-72 | CD86 | DAP12 | FcγRI-γ |
| TAG-72 | CD86 | DAP12 | FcγRIII-γ |
| TAG-72 | CD86 | DAP12 | FcεRIβ |
| TAG-72 | CD86 | DAP12 | FcεRIγ |
| TAG-72 | CD86 | DAP12 | DAP10 |
| TAG-72 | CD86 | DAP12 | DAP12 |
| TAG-72 | CD86 | DAP12 | CD32 |
| TAG-72 | CD86 | DAP12 | CD79a |
| TAG-72 | CD86 | DAP12 | CD79b |
| TAG-72 | CD86 | MyD88 | CD8 |
| TAG-72 | CD86 | MyD88 | CD3ζ |
| TAG-72 | CD86 | MyD88 | CD3δ |
| TAG-72 | CD86 | MyD88 | CD3γ |
| TAG-72 | CD86 | MyD88 | CD3ε |
| TAG-72 | CD86 | MyD88 | FcγRI-γ |
| TAG-72 | CD86 | MyD88 | FcγRIII-γ |
| TAG-72 | CD86 | MyD88 | FcεRIβ |
| TAG-72 | CD86 | MyD88 | FcεRIγ |
| TAG-72 | CD86 | MyD88 | DAP10 |
| TAG-72 | CD86 | MyD88 | DAP12 |
| TAG-72 | CD86 | MyD88 | CD32 |
| TAG-72 | CD86 | MyD88 | CD79a |
| TAG-72 | CD86 | MyD88 | CD79b |
| TAG-72 | CD86 | CD7 | CD8 |
| TAG-72 | CD86 | CD7 | CD3ζ |
| TAG-72 | CD86 | CD7 | CD3δ |
| TAG-72 | CD86 | CD7 | CD3γ |
| TAG-72 | CD86 | CD7 | CD3ε |
| TAG-72 | CD86 | CD7 | FcγRI-γ |
| TAG-72 | CD86 | CD7 | FcγRIII-γ |
| TAG-72 | CD86 | CD7 | FcεRIβ |
| TAG-72 | CD86 | CD7 | FcεRIγ |
| TAG-72 | CD86 | CD7 | DAP10 |
| TAG-72 | CD86 | CD7 | DAP12 |
| TAG-72 | CD86 | CD7 | CD32 |
| TAG-72 | CD86 | CD7 | CD79a |
| TAG-72 | CD86 | CD7 | CD79b |
| TAG-72 | CD86 | BTNL3 | CD8 |
| TAG-72 | CD86 | BTNL3 | CD3ζ |
| TAG-72 | CD86 | BTNL3 | CD3δ |
| TAG-72 | CD86 | BTNL3 | CD3γ |
| TAG-72 | CD86 | BTNL3 | CD3ε |
| TAG-72 | CD86 | BTNL3 | FcγRI-γ |
| TAG-72 | CD86 | BTNL3 | FcγRIII-γ |
| TAG-72 | CD86 | BTNL3 | FcεRIβ |
| TAG-72 | CD86 | BTNL3 | FcεRIγ |
| TAG-72 | CD86 | BTNL3 | DAP10 |
| TAG-72 | CD86 | BTNL3 | DAP12 |
| TAG-72 | CD86 | BTNL3 | CD32 |
| TAG-72 | CD86 | BTNL3 | CD79a |
| TAG-72 | CD86 | BTNL3 | CD79b |
| TAG-72 | CD86 | NKG2D | CD8 |
| TAG-72 | CD86 | NKG2D | CD3ζ |
| TAG-72 | CD86 | NKG2D | CD3δ |
| TAG-72 | CD86 | NKG2D | CD3γ |
| TAG-72 | CD86 | NKG2D | CD3ε |
| TAG-72 | CD86 | NKG2D | FcγRI-γ |
| TAG-72 | CD86 | NKG2D | FcγRIII-γ |
| TAG-72 | CD86 | NKG2D | FcεRIβ |
| TAG-72 | CD86 | NKG2D | FcεRIγ |
| TAG-72 | CD86 | NKG2D | DAP10 |
| TAG-72 | CD86 | NKG2D | DAP12 |
| TAG-72 | CD86 | NKG2D | CD32 |
| TAG-72 | CD86 | NKG2D | CD79a |
| TAG-72 | CD86 | NKG2D | CD79b |
| TAG-72 | OX40 | CD28 | CD8 |
| TAG-72 | OX40 | CD28 | CD3ζ |
| TAG-72 | OX40 | CD28 | CD3δ |
| TAG-72 | OX40 | CD28 | CD3γ |
| TAG-72 | OX40 | CD28 | CD3ε |
| TAG-72 | OX40 | CD28 | FcγRI-γ |
| TAG-72 | OX40 | CD28 | FcγRIII-γ |
| TAG-72 | OX40 | CD28 | FcεRIβ |
| TAG-72 | OX40 | CD28 | FcεRIγ |
| TAG-72 | OX40 | CD28 | DAP10 |
| TAG-72 | OX40 | CD28 | DAP12 |
| TAG-72 | OX40 | CD28 | CD32 |
| TAG-72 | OX40 | CD28 | CD79a |
| TAG-72 | OX40 | CD28 | CD79b |
| TAG-72 | OX40 | CD8 | CD8 |
| TAG-72 | OX40 | CD8 | CD3ζ |
| TAG-72 | OX40 | CD8 | CD3δ |
| TAG-72 | OX40 | CD8 | CD3γ |
| TAG-72 | OX40 | CD8 | CD3ε |
| TAG-72 | OX40 | CD8 | FcγRI-γ |

TABLE 3-continued

Third Generation CARs

| ScFv | Co-stimulatory Signal | Co-stimulatory Signal | Signal Domain |
|---|---|---|---|
| TAG-72 | OX40 | CD8 | FcγRIII-γ |
| TAG-72 | OX40 | CD8 | FcεRIβ |
| TAG-72 | OX40 | CD8 | FcεRIγ |
| TAG-72 | OX40 | CD8 | DAP10 |
| TAG-72 | OX40 | CD8 | DAP12 |
| TAG-72 | OX40 | CD8 | CD32 |
| TAG-72 | OX40 | CD8 | CD79a |
| TAG-72 | OX40 | CD8 | CD79b |
| TAG-72 | OX40 | CD4 | CD8 |
| TAG-72 | OX40 | CD4 | CD3ζ |
| TAG-72 | OX40 | CD4 | CD3δ |
| TAG-72 | OX40 | CD4 | CD3γ |
| TAG-72 | OX40 | CD4 | CD3ε |
| TAG-72 | OX40 | CD4 | FcγRI-γ |
| TAG-72 | OX40 | CD4 | FcγRIII-γ |
| TAG-72 | OX40 | CD4 | FcεRIβ |
| TAG-72 | OX40 | CD4 | FcεRIγ |
| TAG-72 | OX40 | CD4 | DAP10 |
| TAG-72 | OX40 | CD4 | DAP12 |
| TAG-72 | OX40 | CD4 | CD32 |
| TAG-72 | OX40 | CD4 | CD79a |
| TAG-72 | OX40 | CD4 | CD79b |
| TAG-72 | OX40 | b2c | CD8 |
| TAG-72 | OX40 | b2c | CD3ζ |
| TAG-72 | OX40 | b2c | CD3δ |
| TAG-72 | OX40 | b2c | CD3γ |
| TAG-72 | OX40 | b2c | CD3ε |
| TAG-72 | OX40 | b2c | FcγRI-γ |
| TAG-72 | OX40 | b2c | FcγRIII-γ |
| TAG-72 | OX40 | b2c | FcεRIβ |
| TAG-72 | OX40 | b2c | FcεRIγ |
| TAG-72 | OX40 | b2c | DAP10 |
| TAG-72 | OX40 | b2c | DAP12 |
| TAG-72 | OX40 | b2c | CD32 |
| TAG-72 | OX40 | b2c | CD79a |
| TAG-72 | OX40 | b2c | CD79b |
| TAG-72 | OX40 | CD137/41BB | CD8 |
| TAG-72 | OX40 | CD137/41BB | CD3ζ |
| TAG-72 | OX40 | CD137/41BB | CD3δ |
| TAG-72 | OX40 | CD137/41BB | CD3γ |
| TAG-72 | OX40 | CD137/41BB | CD3ε |
| TAG-72 | OX40 | CD137/41BB | FcγRI-γ |
| TAG-72 | OX40 | CD137/41BB | FcγRIII-γ |
| TAG-72 | OX40 | CD137/41BB | FcεRIβ |
| TAG-72 | OX40 | CD137/41BB | FcεRIγ |
| TAG-72 | OX40 | CD137/41BB | DAP10 |
| TAG-72 | OX40 | CD137/41BB | DAP12 |
| TAG-72 | OX40 | CD137/41BB | CD32 |
| TAG-72 | OX40 | CD137/41BB | CD79a |
| TAG-72 | OX40 | CD137/41BB | CD79b |
| TAG-72 | OX40 | ICOS | CD8 |
| TAG-72 | OX40 | ICOS | CD3ζ |
| TAG-72 | OX40 | ICOS | CD3δ |
| TAG-72 | OX40 | ICOS | CD3γ |
| TAG-72 | OX40 | ICOS | CD3ε |
| TAG-72 | OX40 | ICOS | FcγRI-γ |
| TAG-72 | OX40 | ICOS | FcγRIII-γ |
| TAG-72 | OX40 | ICOS | FcεRIβ |
| TAG-72 | OX40 | ICOS | FcεRIγ |
| TAG-72 | OX40 | ICOS | DAP10 |
| TAG-72 | OX40 | ICOS | DAP12 |
| TAG-72 | OX40 | ICOS | CD32 |
| TAG-72 | OX40 | ICOS | CD79a |
| TAG-72 | OX40 | ICOS | CD79b |
| TAG-72 | OX40 | CD27 | CD8 |
| TAG-72 | OX40 | CD27 | CD3ζ |
| TAG-72 | OX40 | CD27 | CD3δ |
| TAG-72 | OX40 | CD27 | CD3γ |
| TAG-72 | OX40 | CD27 | CD3ε |
| TAG-72 | OX40 | CD27 | FcγRI-γ |
| TAG-72 | OX40 | CD27 | FcγRIII-γ |
| TAG-72 | OX40 | CD27 | FcεRIβ |
| TAG-72 | OX40 | CD27 | FcεRIγ |
| TAG-72 | OX40 | CD27 | DAP10 |
| TAG-72 | OX40 | CD27 | DAP12 |
| TAG-72 | OX40 | CD27 | CD32 |
| TAG-72 | OX40 | CD27 | CD79a |
| TAG-72 | OX40 | CD27 | CD79b |
| TAG-72 | OX40 | CD28δ | CD8 |
| TAG-72 | OX40 | CD28δ | CD3ζ |
| TAG-72 | OX40 | CD28δ | CD3δ |
| TAG-72 | OX40 | CD28δ | CD3γ |
| TAG-72 | OX40 | CD28δ | CD3ε |
| TAG-72 | OX40 | CD28δ | FcγRI-γ |
| TAG-72 | OX40 | CD28δ | FcγRIII-γ |
| TAG-72 | OX40 | CD28δ | FcεRIβ |
| TAG-72 | OX40 | CD28δ | FcεRIγ |
| TAG-72 | OX40 | CD28δ | DAP10 |
| TAG-72 | OX40 | CD28δ | DAP12 |
| TAG-72 | OX40 | CD28δ | CD32 |
| TAG-72 | OX40 | CD28δ | CD79a |
| TAG-72 | OX40 | CD28δ | CD79b |
| TAG-72 | OX40 | CD80 | CD8 |
| TAG-72 | OX40 | CD80 | CD3ζ |
| TAG-72 | OX40 | CD80 | CD3δ |
| TAG-72 | OX40 | CD80 | CD3γ |
| TAG-72 | OX40 | CD80 | CD3ε |
| TAG-72 | OX40 | CD80 | FcγRI-γ |
| TAG-72 | OX40 | CD80 | FcγRIII-γ |
| TAG-72 | OX40 | CD80 | FcεRIβ |
| TAG-72 | OX40 | CD80 | FcεRIγ |
| TAG-72 | OX40 | CD80 | DAP10 |
| TAG-72 | OX40 | CD80 | DAP12 |
| TAG-72 | OX40 | CD80 | CD32 |
| TAG-72 | OX40 | CD80 | CD79a |
| TAG-72 | OX40 | CD80 | CD79b |
| TAG-72 | OX40 | CD86 | CD8 |
| TAG-72 | OX40 | CD86 | CD3ζ |
| TAG-72 | OX40 | CD86 | CD3δ |
| TAG-72 | OX40 | CD86 | CD3γ |
| TAG-72 | OX40 | CD86 | CD3ε |
| TAG-72 | OX40 | CD86 | FcγRI-γ |
| TAG-72 | OX40 | CD86 | FcγRIII-γ |
| TAG-72 | OX40 | CD86 | FcεRIβ |
| TAG-72 | OX40 | CD86 | FcεRIγ |
| TAG-72 | OX40 | CD86 | DAP10 |
| TAG-72 | OX40 | CD86 | DAP12 |
| TAG-72 | OX40 | CD86 | CD32 |
| TAG-72 | OX40 | CD86 | CD79a |
| TAG-72 | OX40 | CD86 | CD79b |
| TAG-72 | OX40 | OX40 | CD8 |
| TAG-72 | OX40 | OX40 | CD3ζ |
| TAG-72 | OX40 | OX40 | CD3δ |
| TAG-72 | OX40 | OX40 | CD3γ |
| TAG-72 | OX40 | OX40 | CD3ε |
| TAG-72 | OX40 | OX40 | FcγRI-γ |
| TAG-72 | OX40 | OX40 | FcγRIII-γ |
| TAG-72 | OX40 | OX40 | FcεRIβ |
| TAG-72 | OX40 | OX40 | FcεRIγ |
| TAG-72 | OX40 | OX40 | DAP10 |
| TAG-72 | OX40 | OX40 | DAP12 |
| TAG-72 | OX40 | OX40 | CD32 |
| TAG-72 | OX40 | OX40 | CD79a |
| TAG-72 | OX40 | OX40 | CD79b |
| TAG-72 | OX40 | DAP10 | CD8 |
| TAG-72 | OX40 | DAP10 | CD3ζ |
| TAG-72 | OX40 | DAP10 | CD3δ |
| TAG-72 | OX40 | DAP10 | CD3γ |
| TAG-72 | OX40 | DAP10 | CD3ε |
| TAG-72 | OX40 | DAP10 | FcγRI-γ |
| TAG-72 | OX40 | DAP10 | FcγRIII-γ |
| TAG-72 | OX40 | DAP10 | FcεRIβ |
| TAG-72 | OX40 | DAP10 | FcεRIγ |
| TAG-72 | OX40 | DAP10 | DAP10 |
| TAG-72 | OX40 | DAP10 | DAP12 |
| TAG-72 | OX40 | DAP10 | CD32 |
| TAG-72 | OX40 | DAP10 | CD79a |
| TAG-72 | OX40 | DAP10 | CD79b |
| TAG-72 | OX40 | DAP12 | CD8 |
| TAG-72 | OX40 | DAP12 | CD3ζ |

TABLE 3-continued

Third Generation CARs

| ScFv | Co-stimulatory Signal | Co-stimulatory Signal | Signal Domain |
|---|---|---|---|
| TAG-72 | OX40 | DAP12 | CD3δ |
| TAG-72 | OX40 | DAP12 | CD3γ |
| TAG-72 | OX40 | DAP12 | CD3ε |
| TAG-72 | OX40 | DAP12 | FcγRI-γ |
| TAG-72 | OX40 | DAP12 | FcγRIII-γ |
| TAG-72 | OX40 | DAP12 | FcεRIβ |
| TAG-72 | OX40 | DAP12 | FcεRIγ |
| TAG-72 | OX40 | DAP12 | DAP10 |
| TAG-72 | OX40 | DAP12 | DAP12 |
| TAG-72 | OX40 | DAP12 | CD32 |
| TAG-72 | OX40 | DAP12 | CD79a |
| TAG-72 | OX40 | DAP12 | CD79b |
| TAG-72 | OX40 | MyD88 | CD8 |
| TAG-72 | OX40 | MyD88 | CD3ζ |
| TAG-72 | OX40 | MyD88 | CD3δ |
| TAG-72 | OX40 | MyD88 | CD3γ |
| TAG-72 | OX40 | MyD88 | CD3ε |
| TAG-72 | OX40 | MyD88 | FcγRI-γ |
| TAG-72 | OX40 | MyD88 | FcγRIII-γ |
| TAG-72 | OX40 | MyD88 | FcεRIβ |
| TAG-72 | OX40 | MyD88 | FcεRIγ |
| TAG-72 | OX40 | MyD88 | DAP10 |
| TAG-72 | OX40 | MyD88 | DAP12 |
| TAG-72 | OX40 | MyD88 | CD32 |
| TAG-72 | OX40 | MyD88 | CD79a |
| TAG-72 | OX40 | MyD88 | CD79b |
| TAG-72 | OX40 | CD7 | CD8 |
| TAG-72 | OX40 | CD7 | CD3ζ |
| TAG-72 | OX40 | CD7 | CD3δ |
| TAG-72 | OX40 | CD7 | CD3γ |
| TAG-72 | OX40 | CD7 | CD3ε |
| TAG-72 | OX40 | CD7 | FcγRI-γ |
| TAG-72 | OX40 | CD7 | FcγRIII-γ |
| TAG-72 | OX40 | CD7 | FcεRIβ |
| TAG-72 | OX40 | CD7 | FcεRIγ |
| TAG-72 | OX40 | CD7 | DAP10 |
| TAG-72 | OX40 | CD7 | DAP12 |
| TAG-72 | OX40 | CD7 | CD32 |
| TAG-72 | OX40 | CD7 | CD79a |
| TAG-72 | OX40 | CD7 | CD79b |
| TAG-72 | OX40 | BTNL3 | CD8 |
| TAG-72 | OX40 | BTNL3 | CD3ζ |
| TAG-72 | OX40 | BTNL3 | CD3δ |
| TAG-72 | OX40 | BTNL3 | CD3γ |
| TAG-72 | OX40 | BTNL3 | CD3ε |
| TAG-72 | OX40 | BTNL3 | FcγRI-γ |
| TAG-72 | OX40 | BTNL3 | FcγRIII-γ |
| TAG-72 | OX40 | BTNL3 | FcεRIβ |
| TAG-72 | OX40 | BTNL3 | FcεRIγ |
| TAG-72 | OX40 | BTNL3 | DAP10 |
| TAG-72 | OX40 | BTNL3 | DAP12 |
| TAG-72 | OX40 | BTNL3 | CD32 |
| TAG-72 | OX40 | BTNL3 | CD79a |
| TAG-72 | OX40 | BTNL3 | CD79b |
| TAG-72 | OX40 | NKG2D | CD8 |
| TAG-72 | OX40 | NKG2D | CD3ζ |
| TAG-72 | OX40 | NKG2D | CD3δ |
| TAG-72 | OX40 | NKG2D | CD3γ |
| TAG-72 | OX40 | NKG2D | CD3ε |
| TAG-72 | OX40 | NKG2D | FcγRI-γ |
| TAG-72 | OX40 | NKG2D | FcγRIII-γ |
| TAG-72 | OX40 | NKG2D | FcεRIβ |
| TAG-72 | OX40 | NKG2D | FcεRIγ |
| TAG-72 | OX40 | NKG2D | DAP10 |
| TAG-72 | OX40 | NKG2D | DAP12 |
| TAG-72 | OX40 | NKG2D | CD32 |
| TAG-72 | OX40 | NKG2D | CD79a |
| TAG-72 | OX40 | NKG2D | CD79b |
| TAG-72 | DAP10 | CD28 | CD8 |
| TAG-72 | DAP10 | CD28 | CD3ζ |
| TAG-72 | DAP10 | CD28 | CD3δ |
| TAG-72 | DAP10 | CD28 | CD3γ |
| TAG-72 | DAP10 | CD28 | CD3ε |
| TAG-72 | DAP10 | CD28 | FcγRI-γ |
| TAG-72 | DAP10 | CD28 | FcγRIII-γ |
| TAG-72 | DAP10 | CD28 | FcεRIβ |
| TAG-72 | DAP10 | CD28 | FcεRIγ |
| TAG-72 | DAP10 | CD28 | DAP10 |
| TAG-72 | DAP10 | CD28 | DAP12 |
| TAG-72 | DAP10 | CD28 | CD32 |
| TAG-72 | DAP10 | CD28 | CD79a |
| TAG-72 | DAP10 | CD28 | CD79b |
| TAG-72 | DAP10 | CD8 | CD8 |
| TAG-72 | DAP10 | CD8 | CD3ζ |
| TAG-72 | DAP10 | CD8 | CD3δ |
| TAG-72 | DAP10 | CD8 | CD3γ |
| TAG-72 | DAP10 | CD8 | CD3ε |
| TAG-72 | DAP10 | CD8 | FcγRI-γ |
| TAG-72 | DAP10 | CD8 | FcγRIII-γ |
| TAG-72 | DAP10 | CD8 | FcεRIβ |
| TAG-72 | DAP10 | CD8 | FcεRIγ |
| TAG-72 | DAP10 | CD8 | DAP10 |
| TAG-72 | DAP10 | CD8 | DAP12 |
| TAG-72 | DAP10 | CD8 | CD32 |
| TAG-72 | DAP10 | CD8 | CD79a |
| TAG-72 | DAP10 | CD8 | CD79b |
| TAG-72 | DAP10 | CD4 | CD8 |
| TAG-72 | DAP10 | CD4 | CD3ζ |
| TAG-72 | DAP10 | CD4 | CD3δ |
| TAG-72 | DAP10 | CD4 | CD3γ |
| TAG-72 | DAP10 | CD4 | CD3ε |
| TAG-72 | DAP10 | CD4 | FcγRI-γ |
| TAG-72 | DAP10 | CD4 | FcγRIII-γ |
| TAG-72 | DAP10 | CD4 | FcεRIβ |
| TAG-72 | DAP10 | CD4 | FcεRIγ |
| TAG-72 | DAP10 | CD4 | DAP10 |
| TAG-72 | DAP10 | CD4 | DAP12 |
| TAG-72 | DAP10 | CD4 | CD32 |
| TAG-72 | DAP10 | CD4 | CD79a |
| TAG-72 | DAP10 | CD4 | CD79b |
| TAG-72 | DAP10 | b2c | CD8 |
| TAG-72 | DAP10 | b2c | CD3ζ |
| TAG-72 | DAP10 | b2c | CD3δ |
| TAG-72 | DAP10 | b2c | CD3γ |
| TAG-72 | DAP10 | b2c | CD3ε |
| TAG-72 | DAP10 | b2c | FcγRI-γ |
| TAG-72 | DAP10 | b2c | FcγRIII-γ |
| TAG-72 | DAP10 | b2c | FcεRIβ |
| TAG-72 | DAP10 | b2c | FcεRIγ |
| TAG-72 | DAP10 | b2c | DAP10 |
| TAG-72 | DAP10 | b2c | DAP12 |
| TAG-72 | DAP10 | b2c | CD32 |
| TAG-72 | DAP10 | b2c | CD79a |
| TAG-72 | DAP10 | b2c | CD79b |
| TAG-72 | DAP10 | CD137/41BB | CD8 |
| TAG-72 | DAP10 | CD137/41BB | CD3ζ |
| TAG-72 | DAP10 | CD137/41BB | CD3δ |
| TAG-72 | DAP10 | CD137/41BB | CD3γ |
| TAG-72 | DAP10 | CD137/41BB | CD3ε |
| TAG-72 | DAP10 | CD137/41BB | FcγRI-γ |
| TAG-72 | DAP10 | CD137/41BB | FcγRIII-γ |
| TAG-72 | DAP10 | CD137/41BB | FcεRIβ |
| TAG-72 | DAP10 | CD137/41BB | FcεRIγ |
| TAG-72 | DAP10 | CD137/41BB | DAP10 |
| TAG-72 | DAP10 | CD137/41BB | DAP12 |
| TAG-72 | DAP10 | CD137/41BB | CD32 |
| TAG-72 | DAP10 | CD137/41BB | CD79a |
| TAG-72 | DAP10 | CD137/41BB | CD79b |
| TAG-72 | DAP10 | ICOS | CD8 |
| TAG-72 | DAP10 | ICOS | CD3ζ |
| TAG-72 | DAP10 | ICOS | CD3δ |
| TAG-72 | DAP10 | ICOS | CD3γ |
| TAG-72 | DAP10 | ICOS | CD3ε |
| TAG-72 | DAP10 | ICOS | FcγRI-γ |
| TAG-72 | DAP10 | ICOS | FcγRIII-γ |
| TAG-72 | DAP10 | ICOS | FcεRIβ |
| TAG-72 | DAP10 | ICOS | FcεRIγ |
| TAG-72 | DAP10 | ICOS | DAP10 |
| TAG-72 | DAP10 | ICOS | DAP12 |
| TAG-72 | DAP10 | ICOS | CD32 |

TABLE 3-continued

Third Generation CARs

| ScFv | Co-stimulatory Signal | Co-stimulatory Signal | Signal Domain |
|---|---|---|---|
| TAG-72 | DAP10 | ICOS | CD79a |
| TAG-72 | DAP10 | ICOS | CD79b |
| TAG-72 | DAP10 | CD27 | CD8 |
| TAG-72 | DAP10 | CD27 | CD3ζ |
| TAG-72 | DAP10 | CD27 | CD3δ |
| TAG-72 | DAP10 | CD27 | CD3γ |
| TAG-72 | DAP10 | CD27 | CD3ε |
| TAG-72 | DAP10 | CD27 | FcγRI-γ |
| TAG-72 | DAP10 | CD27 | FcγRIII-γ |
| TAG-72 | DAP10 | CD27 | FcεRIβ |
| TAG-72 | DAP10 | CD27 | FcεRIγ |
| TAG-72 | DAP10 | CD27 | DAP10 |
| TAG-72 | DAP10 | CD27 | DAP12 |
| TAG-72 | DAP10 | CD27 | CD32 |
| TAG-72 | DAP10 | CD27 | CD79a |
| TAG-72 | DAP10 | CD27 | CD79b |
| TAG-72 | DAP10 | CD28δ | CD8 |
| TAG-72 | DAP10 | CD28δ | CD3ζ |
| TAG-72 | DAP10 | CD28δ | CD3δ |
| TAG-72 | DAP10 | CD28δ | CD3γ |
| TAG-72 | DAP10 | CD28δ | CD3ε |
| TAG-72 | DAP10 | CD28δ | FcγRI-γ |
| TAG-72 | DAP10 | CD28δ | FcγRIII-γ |
| TAG-72 | DAP10 | CD28δ | FcεRIβ |
| TAG-72 | DAP10 | CD28δ | FcεRIγ |
| TAG-72 | DAP10 | CD28δ | DAP10 |
| TAG-72 | DAP10 | CD28δ | DAP12 |
| TAG-72 | DAP10 | CD28δ | CD32 |
| TAG-72 | DAP10 | CD28δ | CD79a |
| TAG-72 | DAP10 | CD28δ | CD79b |
| TAG-72 | DAP10 | CD80 | CD8 |
| TAG-72 | DAP10 | CD80 | CD3ζ |
| TAG-72 | DAP10 | CD80 | CD3δ |
| TAG-72 | DAP10 | CD80 | CD3γ |
| TAG-72 | DAP10 | CD80 | CD3ε |
| TAG-72 | DAP10 | CD80 | FcγRI-γ |
| TAG-72 | DAP10 | CD80 | FcγRIII-γ |
| TAG-72 | DAP10 | CD80 | FcεRIβ |
| TAG-72 | DAP10 | CD80 | FcεRIγ |
| TAG-72 | DAP10 | CD80 | DAP10 |
| TAG-72 | DAP10 | CD80 | DAP12 |
| TAG-72 | DAP10 | CD80 | CD32 |
| TAG-72 | DAP10 | CD80 | CD79a |
| TAG-72 | DAP10 | CD80 | CD79b |
| TAG-72 | DAP10 | CD86 | CD8 |
| TAG-72 | DAP10 | CD86 | CD3ζ |
| TAG-72 | DAP10 | CD86 | CD3δ |
| TAG-72 | DAP10 | CD86 | CD3γ |
| TAG-72 | DAP10 | CD86 | CD3ε |
| TAG-72 | DAP10 | CD86 | FcγRI-γ |
| TAG-72 | DAP10 | CD86 | FcγRIII-γ |
| TAG-72 | DAP10 | CD86 | FcεRIβ |
| TAG-72 | DAP10 | CD86 | FcεRIγ |
| TAG-72 | DAP10 | CD86 | DAP10 |
| TAG-72 | DAP10 | CD86 | DAP12 |
| TAG-72 | DAP10 | CD86 | CD32 |
| TAG-72 | DAP10 | CD86 | CD79a |
| TAG-72 | DAP10 | CD86 | CD79b |
| TAG-72 | DAP10 | OX40 | CD8 |
| TAG-72 | DAP10 | OX40 | CD3ζ |
| TAG-72 | DAP10 | OX40 | CD3δ |
| TAG-72 | DAP10 | OX40 | CD3γ |
| TAG-72 | DAP10 | OX40 | CD3ε |
| TAG-72 | DAP10 | OX40 | FcγRI-γ |
| TAG-72 | DAP10 | OX40 | FcγRIII-γ |
| TAG-72 | DAP10 | OX40 | FcεRIβ |
| TAG-72 | DAP10 | OX40 | FcεRIγ |
| TAG-72 | DAP10 | OX40 | DAP10 |
| TAG-72 | DAP10 | OX40 | DAP12 |
| TAG-72 | DAP10 | OX40 | CD32 |
| TAG-72 | DAP10 | OX40 | CD79a |
| TAG-72 | DAP10 | OX40 | CD79b |
| TAG-72 | DAP10 | DAP10 | CD8 |
| TAG-72 | DAP10 | DAP10 | CD3ζ |
| TAG-72 | DAP10 | DAP10 | CD3δ |
| TAG-72 | DAP10 | DAP10 | CD3γ |
| TAG-72 | DAP10 | DAP10 | CD3ε |
| TAG-72 | DAP10 | DAP10 | FcγRI-γ |
| TAG-72 | DAP10 | DAP10 | FcγRIII-γ |
| TAG-72 | DAP10 | DAP10 | FcεRIβ |
| TAG-72 | DAP10 | DAP10 | FcεRIγ |
| TAG-72 | DAP10 | DAP10 | DAP10 |
| TAG-72 | DAP10 | DAP10 | DAP12 |
| TAG-72 | DAP10 | DAP10 | CD32 |
| TAG-72 | DAP10 | DAP10 | CD79a |
| TAG-72 | DAP10 | DAP10 | CD79b |
| TAG-72 | DAP10 | DAP12 | CD8 |
| TAG-72 | DAP10 | DAP12 | CD3ζ |
| TAG-72 | DAP10 | DAP12 | CD3δ |
| TAG-72 | DAP10 | DAP12 | CD3γ |
| TAG-72 | DAP10 | DAP12 | CD3ε |
| TAG-72 | DAP10 | DAP12 | FcγRI-γ |
| TAG-72 | DAP10 | DAP12 | FcγRIII-γ |
| TAG-72 | DAP10 | DAP12 | FcεRIβ |
| TAG-72 | DAP10 | DAP12 | FcεRIγ |
| TAG-72 | DAP10 | DAP12 | DAP10 |
| TAG-72 | DAP10 | DAP12 | DAP12 |
| TAG-72 | DAP10 | DAP12 | CD32 |
| TAG-72 | DAP10 | DAP12 | CD79a |
| TAG-72 | DAP10 | DAP12 | CD79b |
| TAG-72 | DAP10 | MyD88 | CD8 |
| TAG-72 | DAP10 | MyD88 | CD3ζ |
| TAG-72 | DAP10 | MyD88 | CD3δ |
| TAG-72 | DAP10 | MyD88 | CD3γ |
| TAG-72 | DAP10 | MyD88 | CD3ε |
| TAG-72 | DAP10 | MyD88 | FcγRI-γ |
| TAG-72 | DAP10 | MyD88 | FcγRIII-γ |
| TAG-72 | DAP10 | MyD88 | FcεRIβ |
| TAG-72 | DAP10 | MyD88 | FcεRIγ |
| TAG-72 | DAP10 | MyD88 | DAP10 |
| TAG-72 | DAP10 | MyD88 | DAP12 |
| TAG-72 | DAP10 | MyD88 | CD32 |
| TAG-72 | DAP10 | MyD88 | CD79a |
| TAG-72 | DAP10 | MyD88 | CD79b |
| TAG-72 | DAP10 | CD7 | CD8 |
| TAG-72 | DAP10 | CD7 | CD3ζ |
| TAG-72 | DAP10 | CD7 | CD3δ |
| TAG-72 | DAP10 | CD7 | CD3γ |
| TAG-72 | DAP10 | CD7 | CD3ε |
| TAG-72 | DAP10 | CD7 | FcγRI-γ |
| TAG-72 | DAP10 | CD7 | FcγRIII-γ |
| TAG-72 | DAP10 | CD7 | FcεRIβ |
| TAG-72 | DAP10 | CD7 | FcεRIγ |
| TAG-72 | DAP10 | CD7 | DAP10 |
| TAG-72 | DAP10 | CD7 | DAP12 |
| TAG-72 | DAP10 | CD7 | CD32 |
| TAG-72 | DAP10 | CD7 | CD79a |
| TAG-72 | DAP10 | CD7 | CD79b |
| TAG-72 | DAP10 | BTNL3 | CD8 |
| TAG-72 | DAP10 | BTNL3 | CD3ζ |
| TAG-72 | DAP10 | BTNL3 | CD3δ |
| TAG-72 | DAP10 | BTNL3 | CD3γ |
| TAG-72 | DAP10 | BTNL3 | CD3ε |
| TAG-72 | DAP10 | BTNL3 | FcγRI-γ |
| TAG-72 | DAP10 | BTNL3 | FcγRIII-γ |
| TAG-72 | DAP10 | BTNL3 | FcεRIβ |
| TAG-72 | DAP10 | BTNL3 | FcεRIγ |
| TAG-72 | DAP10 | BTNL3 | DAP10 |
| TAG-72 | DAP10 | BTNL3 | DAP12 |
| TAG-72 | DAP10 | BTNL3 | CD32 |
| TAG-72 | DAP10 | BTNL3 | CD79a |
| TAG-72 | DAP10 | BTNL3 | CD79b |
| TAG-72 | DAP10 | NKG2D | CD8 |
| TAG-72 | DAP10 | NKG2D | CD3ζ |
| TAG-72 | DAP10 | NKG2D | CD3δ |
| TAG-72 | DAP10 | NKG2D | CD3γ |
| TAG-72 | DAP10 | NKG2D | CD3ε |
| TAG-72 | DAP10 | NKG2D | FcγRI-γ |
| TAG-72 | DAP10 | NKG2D | FcγRIII-γ |
| TAG-72 | DAP10 | NKG2D | FcεRIβ |

TABLE 3-continued

Third Generation CARs

| ScFv | Co-stimulatory Signal | Co-stimulatory Signal | Signal Domain |
|---|---|---|---|
| TAG-72 | DAP10 | NKG2D | FcεRIγ |
| TAG-72 | DAP10 | NKG2D | DAP10 |
| TAG-72 | DAP10 | NKG2D | DAP12 |
| TAG-72 | DAP10 | NKG2D | CD32 |
| TAG-72 | DAP10 | NKG2D | CD79a |
| TAG-72 | DAP10 | NKG2D | CD79b |
| TAG-72 | DAP12 | CD28 | CD8 |
| TAG-72 | DAP12 | CD28 | CD3ζ |
| TAG-72 | DAP12 | CD28 | CD3δ |
| TAG-72 | DAP12 | CD28 | CD3γ |
| TAG-72 | DAP12 | CD28 | CD3ε |
| TAG-72 | DAP12 | CD28 | FcγRI-γ |
| TAG-72 | DAP12 | CD28 | FcγRIII-γ |
| TAG-72 | DAP12 | CD28 | FcεRIβ |
| TAG-72 | DAP12 | CD28 | FcεRIγ |
| TAG-72 | DAP12 | CD28 | DAP10 |
| TAG-72 | DAP12 | CD28 | DAP12 |
| TAG-72 | DAP12 | CD28 | CD32 |
| TAG-72 | DAP12 | CD28 | CD79a |
| TAG-72 | DAP12 | CD28 | CD79b |
| TAG-72 | DAP12 | CD8 | CD8 |
| TAG-72 | DAP12 | CD8 | CD3ζ |
| TAG-72 | DAP12 | CD8 | CD3δ |
| TAG-72 | DAP12 | CD8 | CD3γ |
| TAG-72 | DAP12 | CD8 | CD3ε |
| TAG-72 | DAP12 | CD8 | FcγRI-γ |
| TAG-72 | DAP12 | CD8 | FcγRIII-γ |
| TAG-72 | DAP12 | CD8 | FcεRIβ |
| TAG-72 | DAP12 | CD8 | FcεRIγ |
| TAG-72 | DAP12 | CD8 | DAP10 |
| TAG-72 | DAP12 | CD8 | DAP12 |
| TAG-72 | DAP12 | CD8 | CD32 |
| TAG-72 | DAP12 | CD8 | CD79a |
| TAG-72 | DAP12 | CD8 | CD79b |
| TAG-72 | DAP12 | CD4 | CD8 |
| TAG-72 | DAP12 | CD4 | CD3ζ |
| TAG-72 | DAP12 | CD4 | CD3δ |
| TAG-72 | DAP12 | CD4 | CD3γ |
| TAG-72 | DAP12 | CD4 | CD3ε |
| TAG-72 | DAP12 | CD4 | FcγRI-γ |
| TAG-72 | DAP12 | CD4 | FcγRIII-γ |
| TAG-72 | DAP12 | CD4 | FcεRIβ |
| TAG-72 | DAP12 | CD4 | FcεRIγ |
| TAG-72 | DAP12 | CD4 | DAP10 |
| TAG-72 | DAP12 | CD4 | DAP12 |
| TAG-72 | DAP12 | CD4 | CD32 |
| TAG-72 | DAP12 | CD4 | CD79a |
| TAG-72 | DAP12 | CD4 | CD79b |
| TAG-72 | DAP12 | b2c | CD8 |
| TAG-72 | DAP12 | b2c | CD3ζ |
| TAG-72 | DAP12 | b2c | CD3δ |
| TAG-72 | DAP12 | b2c | CD3γ |
| TAG-72 | DAP12 | b2c | CD3ε |
| TAG-72 | DAP12 | b2c | FcγRI-γ |
| TAG-72 | DAP12 | b2c | FcγRIII-γ |
| TAG-72 | DAP12 | b2c | FcεRIβ |
| TAG-72 | DAP12 | b2c | FcεRIγ |
| TAG-72 | DAP12 | b2c | DAP10 |
| TAG-72 | DAP12 | b2c | DAP12 |
| TAG-72 | DAP12 | b2c | CD32 |
| TAG-72 | DAP12 | b2c | CD79a |
| TAG-72 | DAP12 | b2c | CD79b |
| TAG-72 | DAP12 | CD137/41BB | CD8 |
| TAG-72 | DAP12 | CD137/41BB | CD3ζ |
| TAG-72 | DAP12 | CD137/41BB | CD3δ |
| TAG-72 | DAP12 | CD137/41BB | CD3γ |
| TAG-72 | DAP12 | CD137/41BB | CD3ε |
| TAG-72 | DAP12 | CD137/41BB | FcγRI-γ |
| TAG-72 | DAP12 | CD137/41BB | FcγRIII-γ |
| TAG-72 | DAP12 | CD137/41BB | FcεRIβ |
| TAG-72 | DAP12 | CD137/41BB | FcεRIγ |
| TAG-72 | DAP12 | CD137/41BB | DAP10 |
| TAG-72 | DAP12 | CD137/41BB | DAP12 |
| TAG-72 | DAP12 | CD137/41BB | CD32 |
| TAG-72 | DAP12 | CD137/41BB | CD79a |
| TAG-72 | DAP12 | CD137/41BB | CD79b |
| TAG-72 | DAP12 | ICOS | CD8 |
| TAG-72 | DAP12 | ICOS | CD3ζ |
| TAG-72 | DAP12 | ICOS | CD3δ |
| TAG-72 | DAP12 | ICOS | CD3γ |
| TAG-72 | DAP12 | ICOS | CD3ε |
| TAG-72 | DAP12 | ICOS | FcγRI-γ |
| TAG-72 | DAP12 | ICOS | FcγRIII-γ |
| TAG-72 | DAP12 | ICOS | FcεRIβ |
| TAG-72 | DAP12 | ICOS | FcεRIγ |
| TAG-72 | DAP12 | ICOS | DAP10 |
| TAG-72 | DAP12 | ICOS | DAP12 |
| TAG-72 | DAP12 | ICOS | CD32 |
| TAG-72 | DAP12 | ICOS | CD79a |
| TAG-72 | DAP12 | ICOS | CD79b |
| TAG-72 | DAP12 | CD27 | CD8 |
| TAG-72 | DAP12 | CD27 | CD3ζ |
| TAG-72 | DAP12 | CD27 | CD3δ |
| TAG-72 | DAP12 | CD27 | CD3γ |
| TAG-72 | DAP12 | CD27 | CD3ε |
| TAG-72 | DAP12 | CD27 | FcγRI-γ |
| TAG-72 | DAP12 | CD27 | FcγRIII-γ |
| TAG-72 | DAP12 | CD27 | FcεRIβ |
| TAG-72 | DAP12 | CD27 | FcεRIγ |
| TAG-72 | DAP12 | CD27 | DAP10 |
| TAG-72 | DAP12 | CD27 | DAP12 |
| TAG-72 | DAP12 | CD27 | CD32 |
| TAG-72 | DAP12 | CD27 | CD79a |
| TAG-72 | DAP12 | CD27 | CD79b |
| TAG-72 | DAP12 | CD28δ | CD8 |
| TAG-72 | DAP12 | CD28δ | CD3ζ |
| TAG-72 | DAP12 | CD28δ | CD3δ |
| TAG-72 | DAP12 | CD28δ | CD3γ |
| TAG-72 | DAP12 | CD28δ | CD3ε |
| TAG-72 | DAP12 | CD28δ | FcγRI-γ |
| TAG-72 | DAP12 | CD28δ | FcγRIII-γ |
| TAG-72 | DAP12 | CD28δ | FcεRIβ |
| TAG-72 | DAP12 | CD28δ | FcεRIγ |
| TAG-72 | DAP12 | CD28δ | DAP10 |
| TAG-72 | DAP12 | CD28δ | DAP12 |
| TAG-72 | DAP12 | CD28δ | CD32 |
| TAG-72 | DAP12 | CD28δ | CD79a |
| TAG-72 | DAP12 | CD28δ | CD79b |
| TAG-72 | DAP12 | CD80 | CD8 |
| TAG-72 | DAP12 | CD80 | CD3ζ |
| TAG-72 | DAP12 | CD80 | CD3δ |
| TAG-72 | DAP12 | CD80 | CD3γ |
| TAG-72 | DAP12 | CD80 | CD3ε |
| TAG-72 | DAP12 | CD80 | FcγRI-γ |
| TAG-72 | DAP12 | CD80 | FcγRIII-γ |
| TAG-72 | DAP12 | CD80 | FcεRIβ |
| TAG-72 | DAP12 | CD80 | FcεRIγ |
| TAG-72 | DAP12 | CD80 | DAP10 |
| TAG-72 | DAP12 | CD80 | DAP12 |
| TAG-72 | DAP12 | CD80 | CD32 |
| TAG-72 | DAP12 | CD80 | CD79a |
| TAG-72 | DAP12 | CD80 | CD79b |
| TAG-72 | DAP12 | CD86 | CD8 |
| TAG-72 | DAP12 | CD86 | CD3ζ |
| TAG-72 | DAP12 | CD86 | CD3δ |
| TAG-72 | DAP12 | CD86 | CD3γ |
| TAG-72 | DAP12 | CD86 | CD3ε |
| TAG-72 | DAP12 | CD86 | FcγRI-γ |
| TAG-72 | DAP12 | CD86 | FcγRIII-γ |
| TAG-72 | DAP12 | CD86 | FcεRIβ |
| TAG-72 | DAP12 | CD86 | FcεRIγ |
| TAG-72 | DAP12 | CD86 | DAP10 |
| TAG-72 | DAP12 | CD86 | DAP12 |
| TAG-72 | DAP12 | CD86 | CD32 |
| TAG-72 | DAP12 | CD86 | CD79a |
| TAG-72 | DAP12 | CD86 | CD79b |
| TAG-72 | DAP12 | OX40 | CD8 |
| TAG-72 | DAP12 | OX40 | CD3ζ |
| TAG-72 | DAP12 | OX40 | CD3δ |
| TAG-72 | DAP12 | OX40 | CD3γ |

TABLE 3-continued

Third Generation CARs

| ScFv | Co-stimulatory Signal | Co-stimulatory Signal | Signal Domain |
|---|---|---|---|
| TAG-72 | DAP12 | OX40 | CD3ε |
| TAG-72 | DAP12 | OX40 | FcγRI-γ |
| TAG-72 | DAP12 | OX40 | FcγRIII-γ |
| TAG-72 | DAP12 | OX40 | FcεRIβ |
| TAG-72 | DAP12 | OX40 | FcεRIγ |
| TAG-72 | DAP12 | OX40 | DAP10 |
| TAG-72 | DAP12 | OX40 | DAP12 |
| TAG-72 | DAP12 | OX40 | CD32 |
| TAG-72 | DAP12 | OX40 | CD79a |
| TAG-72 | DAP12 | OX40 | CD79b |
| TAG-72 | DAP12 | DAP10 | CD8 |
| TAG-72 | DAP12 | DAP10 | CD3ζ |
| TAG-72 | DAP12 | DAP10 | CD3δ |
| TAG-72 | DAP12 | DAP10 | CD3γ |
| TAG-72 | DAP12 | DAP10 | CD3ε |
| TAG-72 | DAP12 | DAP10 | FcγRI-γ |
| TAG-72 | DAP12 | DAP10 | FcγRIII-γ |
| TAG-72 | DAP12 | DAP10 | FcεRIβ |
| TAG-72 | DAP12 | DAP10 | FcεRIγ |
| TAG-72 | DAP12 | DAP10 | DAP10 |
| TAG-72 | DAP12 | DAP10 | DAP12 |
| TAG-72 | DAP12 | DAP10 | CD32 |
| TAG-72 | DAP12 | DAP10 | CD79a |
| TAG-72 | DAP12 | DAP10 | CD79b |
| TAG-72 | DAP12 | DAP12 | CD8 |
| TAG-72 | DAP12 | DAP12 | CD3ζ |
| TAG-72 | DAP12 | DAP12 | CD3δ |
| TAG-72 | DAP12 | DAP12 | CD3γ |
| TAG-72 | DAP12 | DAP12 | CD3ε |
| TAG-72 | DAP12 | DAP12 | FcγRI-γ |
| TAG-72 | DAP12 | DAP12 | FcγRIII-γ |
| TAG-72 | DAP12 | DAP12 | FcεRIβ |
| TAG-72 | DAP12 | DAP12 | FcεRIγ |
| TAG-72 | DAP12 | DAP12 | DAP10 |
| TAG-72 | DAP12 | DAP12 | DAP12 |
| TAG-72 | DAP12 | DAP12 | CD32 |
| TAG-72 | DAP12 | DAP12 | CD79a |
| TAG-72 | DAP12 | DAP12 | CD79b |
| TAG-72 | DAP12 | MyD88 | CD8 |
| TAG-72 | DAP12 | MyD88 | CD3ζ |
| TAG-72 | DAP12 | MyD88 | CD3δ |
| TAG-72 | DAP12 | MyD88 | CD3γ |
| TAG-72 | DAP12 | MyD88 | CD3ε |
| TAG-72 | DAP12 | MyD88 | FcγRI-γ |
| TAG-72 | DAP12 | MyD88 | FcγRIII-γ |
| TAG-72 | DAP12 | MyD88 | FcεRIβ |
| TAG-72 | DAP12 | MyD88 | FcεRIγ |
| TAG-72 | DAP12 | MyD88 | DAP10 |
| TAG-72 | DAP12 | MyD88 | DAP12 |
| TAG-72 | DAP12 | MyD88 | CD32 |
| TAG-72 | DAP12 | MyD88 | CD79a |
| TAG-72 | DAP12 | MyD88 | CD79b |
| TAG-72 | DAP12 | CD7 | CD8 |
| TAG-72 | DAP12 | CD7 | CD3ζ |
| TAG-72 | DAP12 | CD7 | CD3δ |
| TAG-72 | DAP12 | CD7 | CD3γ |
| TAG-72 | DAP12 | CD7 | CD3ε |
| TAG-72 | DAP12 | CD7 | FcγRI-γ |
| TAG-72 | DAP12 | CD7 | FcγRIII-γ |
| TAG-72 | DAP12 | CD7 | FcεRIβ |
| TAG-72 | DAP12 | CD7 | FcεRIγ |
| TAG-72 | DAP12 | CD7 | DAP10 |
| TAG-72 | DAP12 | CD7 | DAP12 |
| TAG-72 | DAP12 | CD7 | CD32 |
| TAG-72 | DAP12 | CD7 | CD79a |
| TAG-72 | DAP12 | CD7 | CD79b |
| TAG-72 | DAP12 | BTNL3 | CD8 |
| TAG-72 | DAP12 | BTNL3 | CD3ζ |
| TAG-72 | DAP12 | BTNL3 | CD3δ |
| TAG-72 | DAP12 | BTNL3 | CD3γ |
| TAG-72 | DAP12 | BTNL3 | CD3ε |
| TAG-72 | DAP12 | BTNL3 | FcγRI-γ |
| TAG-72 | DAP12 | BTNL3 | FcγRIII-γ |
| TAG-72 | DAP12 | BTNL3 | FcεRIβ |
| TAG-72 | DAP12 | BTNL3 | FcεRIγ |
| TAG-72 | DAP12 | BTNL3 | DAP10 |
| TAG-72 | DAP12 | BTNL3 | DAP12 |
| TAG-72 | DAP12 | BTNL3 | CD32 |
| TAG-72 | DAP12 | BTNL3 | CD79a |
| TAG-72 | DAP12 | BTNL3 | CD79b |
| TAG-72 | DAP12 | NKG2D | CD8 |
| TAG-72 | DAP12 | NKG2D | CD3ζ |
| TAG-72 | DAP12 | NKG2D | CD3δ |
| TAG-72 | DAP12 | NKG2D | CD3γ |
| TAG-72 | DAP12 | NKG2D | CD3ε |
| TAG-72 | DAP12 | NKG2D | FcγRI-γ |
| TAG-72 | DAP12 | NKG2D | FcγRIII-γ |
| TAG-72 | DAP12 | NKG2D | FcεRIβ |
| TAG-72 | DAP12 | NKG2D | FcεRIγ |
| TAG-72 | DAP12 | NKG2D | DAP10 |
| TAG-72 | DAP12 | NKG2D | DAP12 |
| TAG-72 | DAP12 | NKG2D | CD32 |
| TAG-72 | DAP12 | NKG2D | CD79a |
| TAG-72 | DAP12 | NKG2D | CD79b |
| TAG-72 | MyD88 | CD28 | CD8 |
| TAG-72 | MyD88 | CD28 | CD3ζ |
| TAG-72 | MyD88 | CD28 | CD3δ |
| TAG-72 | MyD88 | CD28 | CD3γ |
| TAG-72 | MyD88 | CD28 | CD3ε |
| TAG-72 | MyD88 | CD28 | FcγRI-γ |
| TAG-72 | MyD88 | CD28 | FcγRIII-γ |
| TAG-72 | MyD88 | CD28 | FcεRIβ |
| TAG-72 | MyD88 | CD28 | FcεRIγ |
| TAG-72 | MyD88 | CD28 | DAP10 |
| TAG-72 | MyD88 | CD28 | DAP12 |
| TAG-72 | MyD88 | CD28 | CD32 |
| TAG-72 | MyD88 | CD28 | CD79a |
| TAG-72 | MyD88 | CD28 | CD79b |
| TAG-72 | MyD88 | CD8 | CD8 |
| TAG-72 | MyD88 | CD8 | CD3ζ |
| TAG-72 | MyD88 | CD8 | CD3δ |
| TAG-72 | MyD88 | CD8 | CD3γ |
| TAG-72 | MyD88 | CD8 | CD3ε |
| TAG-72 | MyD88 | CD8 | FcγRI-γ |
| TAG-72 | MyD88 | CD8 | FcγRIII-γ |
| TAG-72 | MyD88 | CD8 | FcεRIβ |
| TAG-72 | MyD88 | CD8 | FcεRIγ |
| TAG-72 | MyD88 | CD8 | DAP10 |
| TAG-72 | MyD88 | CD8 | DAP12 |
| TAG-72 | MyD88 | CD8 | CD32 |
| TAG-72 | MyD88 | CD8 | CD79a |
| TAG-72 | MyD88 | CD8 | CD79b |
| TAG-72 | MyD88 | CD4 | CD8 |
| TAG-72 | MyD88 | CD4 | CD3ζ |
| TAG-72 | MyD88 | CD4 | CD3δ |
| TAG-72 | MyD88 | CD4 | CD3γ |
| TAG-72 | MyD88 | CD4 | CD3ε |
| TAG-72 | MyD88 | CD4 | FcγRI-γ |
| TAG-72 | MyD88 | CD4 | FcγRIII-γ |
| TAG-72 | MyD88 | CD4 | FcεRIβ |
| TAG-72 | MyD88 | CD4 | FcεRIγ |
| TAG-72 | MyD88 | CD4 | DAP10 |
| TAG-72 | MyD88 | CD4 | DAP12 |
| TAG-72 | MyD88 | CD4 | CD32 |
| TAG-72 | MyD88 | CD4 | CD79a |
| TAG-72 | MyD88 | CD4 | CD79b |
| TAG-72 | MyD88 | b2c | CD8 |
| TAG-72 | MyD88 | b2c | CD3ζ |
| TAG-72 | MyD88 | b2c | CD3δ |
| TAG-72 | MyD88 | b2c | CD3γ |
| TAG-72 | MyD88 | b2c | CD3ε |
| TAG-72 | MyD88 | b2c | FcγRI-γ |
| TAG-72 | MyD88 | b2c | FcγRIII-γ |
| TAG-72 | MyD88 | b2c | FcεRIβ |
| TAG-72 | MyD88 | b2c | FcεRIγ |
| TAG-72 | MyD88 | b2c | DAP10 |
| TAG-72 | MyD88 | b2c | DAP12 |
| TAG-72 | MyD88 | b2c | CD32 |
| TAG-72 | MyD88 | b2c | CD79a |
| TAG-72 | MyD88 | b2c | CD79b |

TABLE 3-continued

Third Generation CARs

| ScFv | Co-stimulatory Signal | Co-stimulatory Signal | Signal Domain |
|---|---|---|---|
| TAG-72 | MyD88 | CD137/41BB | CD8 |
| TAG-72 | MyD88 | CD137/41BB | CD3ζ |
| TAG-72 | MyD88 | CD137/41BB | CD3δ |
| TAG-72 | MyD88 | CD137/41BB | CD3γ |
| TAG-72 | MyD88 | CD137/41BB | CD3ε |
| TAG-72 | MyD88 | CD137/41BB | FcγRI-γ |
| TAG-72 | MyD88 | CD137/41BB | FcγRIII-γ |
| TAG-72 | MyD88 | CD137/41BB | FcεRIβ |
| TAG-72 | MyD88 | CD137/41BB | FcεRIγ |
| TAG-72 | MyD88 | CD137/41BB | DAP10 |
| TAG-72 | MyD88 | CD137/41BB | DAP12 |
| TAG-72 | MyD88 | CD137/41BB | CD32 |
| TAG-72 | MyD88 | CD137/41BB | CD79a |
| TAG-72 | MyD88 | CD137/41BB | CD79b |
| TAG-72 | MyD88 | ICOS | CD8 |
| TAG-72 | MyD88 | ICOS | CD3ζ |
| TAG-72 | MyD88 | ICOS | CD3δ |
| TAG-72 | MyD88 | ICOS | CD3γ |
| TAG-72 | MyD88 | ICOS | CD3ε |
| TAG-72 | MyD88 | ICOS | FcγRI-γ |
| TAG-72 | MyD88 | ICOS | FcγRIII-γ |
| TAG-72 | MyD88 | ICOS | FcεRIβ |
| TAG-72 | MyD88 | ICOS | FcεRIγ |
| TAG-72 | MyD88 | ICOS | DAP10 |
| TAG-72 | MyD88 | ICOS | DAP12 |
| TAG-72 | MyD88 | ICOS | CD32 |
| TAG-72 | MyD88 | ICOS | CD79a |
| TAG-72 | MyD88 | ICOS | CD79b |
| TAG-72 | MyD88 | CD27 | CD8 |
| TAG-72 | MyD88 | CD27 | CD3ζ |
| TAG-72 | MyD88 | CD27 | CD3δ |
| TAG-72 | MyD88 | CD27 | CD3γ |
| TAG-72 | MyD88 | CD27 | CD3ε |
| TAG-72 | MyD88 | CD27 | FcγRI-γ |
| TAG-72 | MyD88 | CD27 | FcγRIII-γ |
| TAG-72 | MyD88 | CD27 | FcεRIβ |
| TAG-72 | MyD88 | CD27 | FcεRIγ |
| TAG-72 | MyD88 | CD27 | DAP10 |
| TAG-72 | MyD88 | CD27 | DAP12 |
| TAG-72 | MyD88 | CD27 | CD32 |
| TAG-72 | MyD88 | CD27 | CD79a |
| TAG-72 | MyD88 | CD27 | CD79b |
| TAG-72 | MyD88 | CD28δ | CD8 |
| TAG-72 | MyD88 | CD28δ | CD3ζ |
| TAG-72 | MyD88 | CD28δ | CD3δ |
| TAG-72 | MyD88 | CD28δ | CD3γ |
| TAG-72 | MyD88 | CD28δ | CD3ε |
| TAG-72 | MyD88 | CD28δ | FcγRI-γ |
| TAG-72 | MyD88 | CD28δ | FcγRIII-γ |
| TAG-72 | MyD88 | CD28δ | FcεRIβ |
| TAG-72 | MyD88 | CD28δ | FcεRIγ |
| TAG-72 | MyD88 | CD28δ | DAP10 |
| TAG-72 | MyD88 | CD28δ | DAP12 |
| TAG-72 | MyD88 | CD28δ | CD32 |
| TAG-72 | MyD88 | CD28δ | CD79a |
| TAG-72 | MyD88 | CD28δ | CD79b |
| TAG-72 | MyD88 | CD80 | CD8 |
| TAG-72 | MyD88 | CD80 | CD3ζ |
| TAG-72 | MyD88 | CD80 | CD3δ |
| TAG-72 | MyD88 | CD80 | CD3γ |
| TAG-72 | MyD88 | CD80 | CD3ε |
| TAG-72 | MyD88 | CD80 | FcγRI-γ |
| TAG-72 | MyD88 | CD80 | FcγRIII-γ |
| TAG-72 | MyD88 | CD80 | FcεRIβ |
| TAG-72 | MyD88 | CD80 | FcεRIγ |
| TAG-72 | MyD88 | CD80 | DAP10 |
| TAG-72 | MyD88 | CD80 | DAP12 |
| TAG-72 | MyD88 | CD80 | CD32 |
| TAG-72 | MyD88 | CD80 | CD79a |
| TAG-72 | MyD88 | CD80 | CD79b |
| TAG-72 | MyD88 | CD86 | CD8 |
| TAG-72 | MyD88 | CD86 | CD3ζ |
| TAG-72 | MyD88 | CD86 | CD3δ |
| TAG-72 | MyD88 | CD86 | CD3γ |
| TAG-72 | MyD88 | CD86 | CD3ε |
| TAG-72 | MyD88 | CD86 | FcγRI-γ |
| TAG-72 | MyD88 | CD86 | FcγRIII-γ |
| TAG-72 | MyD88 | CD86 | FcεRIβ |
| TAG-72 | MyD88 | CD86 | FcεRIγ |
| TAG-72 | MyD88 | CD86 | DAP10 |
| TAG-72 | MyD88 | CD86 | DAP12 |
| TAG-72 | MyD88 | CD86 | CD32 |
| TAG-72 | MyD88 | CD86 | CD79a |
| TAG-72 | MyD88 | CD86 | CD79b |
| TAG-72 | MyD88 | OX40 | CD8 |
| TAG-72 | MyD88 | OX40 | CD3ζ |
| TAG-72 | MyD88 | OX40 | CD3δ |
| TAG-72 | MyD88 | OX40 | CD3γ |
| TAG-72 | MyD88 | OX40 | CD3ε |
| TAG-72 | MyD88 | OX40 | FcγRI-γ |
| TAG-72 | MyD88 | OX40 | FcγRIII-γ |
| TAG-72 | MyD88 | OX40 | FcεRIβ |
| TAG-72 | MyD88 | OX40 | FcεRIγ |
| TAG-72 | MyD88 | OX40 | DAP10 |
| TAG-72 | MyD88 | OX40 | DAP12 |
| TAG-72 | MyD88 | OX40 | CD32 |
| TAG-72 | MyD88 | OX40 | CD79a |
| TAG-72 | MyD88 | OX40 | CD79b |
| TAG-72 | MyD88 | DAP10 | CD8 |
| TAG-72 | MyD88 | DAP10 | CD3ζ |
| TAG-72 | MyD88 | DAP10 | CD3δ |
| TAG-72 | MyD88 | DAP10 | CD3γ |
| TAG-72 | MyD88 | DAP10 | CD3ε |
| TAG-72 | MyD88 | DAP10 | FcγRI-γ |
| TAG-72 | MyD88 | DAP10 | FcγRIII-γ |
| TAG-72 | MyD88 | DAP10 | FcεRIβ |
| TAG-72 | MyD88 | DAP10 | FcεRIγ |
| TAG-72 | MyD88 | DAP10 | DAP10 |
| TAG-72 | MyD88 | DAP10 | DAP12 |
| TAG-72 | MyD88 | DAP10 | CD32 |
| TAG-72 | MyD88 | DAP10 | CD79a |
| TAG-72 | MyD88 | DAP10 | CD79b |
| TAG-72 | MyD88 | DAP12 | CD8 |
| TAG-72 | MyD88 | DAP12 | CD3ζ |
| TAG-72 | MyD88 | DAP12 | CD3δ |
| TAG-72 | MyD88 | DAP12 | CD3γ |
| TAG-72 | MyD88 | DAP12 | CD3ε |
| TAG-72 | MyD88 | DAP12 | FcγRI-γ |
| TAG-72 | MyD88 | DAP12 | FcγRIII-γ |
| TAG-72 | MyD88 | DAP12 | FcεRIβ |
| TAG-72 | MyD88 | DAP12 | FcεRIγ |
| TAG-72 | MyD88 | DAP12 | DAP10 |
| TAG-72 | MyD88 | DAP12 | DAP12 |
| TAG-72 | MyD88 | DAP12 | CD32 |
| TAG-72 | MyD88 | DAP12 | CD79a |
| TAG-72 | MyD88 | DAP12 | CD79b |
| TAG-72 | MyD88 | MyD88 | CD8 |
| TAG-72 | MyD88 | MyD88 | CD3ζ |
| TAG-72 | MyD88 | MyD88 | CD3δ |
| TAG-72 | MyD88 | MyD88 | CD3γ |
| TAG-72 | MyD88 | MyD88 | CD3ε |
| TAG-72 | MyD88 | MyD88 | FcγRI-γ |
| TAG-72 | MyD88 | MyD88 | FcγRIII-γ |
| TAG-72 | MyD88 | MyD88 | FcεRIβ |
| TAG-72 | MyD88 | MyD88 | FcεRIγ |
| TAG-72 | MyD88 | MyD88 | DAP10 |
| TAG-72 | MyD88 | MyD88 | DAP12 |
| TAG-72 | MyD88 | MyD88 | CD32 |
| TAG-72 | MyD88 | MyD88 | CD79a |
| TAG-72 | MyD88 | MyD88 | CD79b |
| TAG-72 | MyD88 | CD7 | CD8 |
| TAG-72 | MyD88 | CD7 | CD3ζ |
| TAG-72 | MyD88 | CD7 | CD3δ |
| TAG-72 | MyD88 | CD7 | CD3γ |
| TAG-72 | MyD88 | CD7 | CD3ε |
| TAG-72 | MyD88 | CD7 | FcγRI-γ |
| TAG-72 | MyD88 | CD7 | FcγRIII-γ |
| TAG-72 | MyD88 | CD7 | FcεRIβ |
| TAG-72 | MyD88 | CD7 | FcεRIγ |
| TAG-72 | MyD88 | CD7 | DAP10 |

TABLE 3-continued

Third Generation CARs

| ScFv | Co-stimulatory Signal | Co-stimulatory Signal | Signal Domain |
|---|---|---|---|
| TAG-72 | MyD88 | CD7 | DAP12 |
| TAG-72 | MyD88 | CD7 | CD32 |
| TAG-72 | MyD88 | CD7 | CD79a |
| TAG-72 | MyD88 | CD7 | CD79b |
| TAG-72 | MyD88 | BTNL3 | CD8 |
| TAG-72 | MyD88 | BTNL3 | CD3ζ |
| TAG-72 | MyD88 | BTNL3 | CD3δ |
| TAG-72 | MyD88 | BTNL3 | CD3γ |
| TAG-72 | MyD88 | BTNL3 | CD3ε |
| TAG-72 | MyD88 | BTNL3 | FcγRI-γ |
| TAG-72 | MyD88 | BTNL3 | FcγRIII-γ |
| TAG-72 | MyD88 | BTNL3 | FcεRIβ |
| TAG-72 | MyD88 | BTNL3 | FcεRIγ |
| TAG-72 | MyD88 | BTNL3 | DAP10 |
| TAG-72 | MyD88 | BTNL3 | DAP12 |
| TAG-72 | MyD88 | BTNL3 | CD32 |
| TAG-72 | MyD88 | BTNL3 | CD79a |
| TAG-72 | MyD88 | BTNL3 | CD79b |
| TAG-72 | MyD88 | NKG2D | CD8 |
| TAG-72 | MyD88 | NKG2D | CD3ζ |
| TAG-72 | MyD88 | NKG2D | CD3δ |
| TAG-72 | MyD88 | NKG2D | CD3γ |
| TAG-72 | MyD88 | NKG2D | CD3ε |
| TAG-72 | MyD88 | NKG2D | FcγRI-γ |
| TAG-72 | MyD88 | NKG2D | FcγRIII-γ |
| TAG-72 | MyD88 | NKG2D | FcεRIβ |
| TAG-72 | MyD88 | NKG2D | FcεRIγ |
| TAG-72 | MyD88 | NKG2D | DAP10 |
| TAG-72 | MyD88 | NKG2D | DAP12 |
| TAG-72 | MyD88 | NKG2D | CD32 |
| TAG-72 | MyD88 | NKG2D | CD79a |
| TAG-72 | MyD88 | NKG2D | CD79b |
| TAG-72 | CD7 | CD28 | CD8 |
| TAG-72 | CD7 | CD28 | CD3ζ |
| TAG-72 | CD7 | CD28 | CD3δ |
| TAG-72 | CD7 | CD28 | CD3γ |
| TAG-72 | CD7 | CD28 | CD3ε |
| TAG-72 | CD7 | CD28 | FcγRI-γ |
| TAG-72 | CD7 | CD28 | FcγRIII-γ |
| TAG-72 | CD7 | CD28 | FcεRIβ |
| TAG-72 | CD7 | CD28 | FcεRIγ |
| TAG-72 | CD7 | CD28 | DAP10 |
| TAG-72 | CD7 | CD28 | DAP12 |
| TAG-72 | CD7 | CD28 | CD32 |
| TAG-72 | CD7 | CD28 | CD79a |
| TAG-72 | CD7 | CD28 | CD79b |
| TAG-72 | CD7 | CD8 | CD8 |
| TAG-72 | CD7 | CD8 | CD3ζ |
| TAG-72 | CD7 | CD8 | CD3δ |
| TAG-72 | CD7 | CD8 | CD3γ |
| TAG-72 | CD7 | CD8 | CD3ε |
| TAG-72 | CD7 | CD8 | FcγRI-γ |
| TAG-72 | CD7 | CD8 | FcγRIII-γ |
| TAG-72 | CD7 | CD8 | FcεRIβ |
| TAG-72 | CD7 | CD8 | FcεRIγ |
| TAG-72 | CD7 | CD8 | DAP10 |
| TAG-72 | CD7 | CD8 | DAP12 |
| TAG-72 | CD7 | CD8 | CD32 |
| TAG-72 | CD7 | CD8 | CD79a |
| TAG-72 | CD7 | CD8 | CD79b |
| TAG-72 | CD7 | CD4 | CD8 |
| TAG-72 | CD7 | CD4 | CD3ζ |
| TAG-72 | CD7 | CD4 | CD3δ |
| TAG-72 | CD7 | CD4 | CD3γ |
| TAG-72 | CD7 | CD4 | CD3ε |
| TAG-72 | CD7 | CD4 | FcγRI-γ |
| TAG-72 | CD7 | CD4 | FcγRIII-γ |
| TAG-72 | CD7 | CD4 | FcεRIβ |
| TAG-72 | CD7 | CD4 | FcεRIγ |
| TAG-72 | CD7 | CD4 | DAP10 |
| TAG-72 | CD7 | CD4 | DAP12 |
| TAG-72 | CD7 | CD4 | CD32 |
| TAG-72 | CD7 | CD4 | CD79a |
| TAG-72 | CD7 | CD4 | CD79b |
| TAG-72 | CD7 | b2c | CD8 |
| TAG-72 | CD7 | b2c | CD3ζ |
| TAG-72 | CD7 | b2c | CD3δ |
| TAG-72 | CD7 | b2c | CD3γ |
| TAG-72 | CD7 | b2c | CD3ε |
| TAG-72 | CD7 | b2c | FcγRI-γ |
| TAG-72 | CD7 | b2c | FcγRIII-γ |
| TAG-72 | CD7 | b2c | FcεRIβ |
| TAG-72 | CD7 | b2c | FcεRIγ |
| TAG-72 | CD7 | b2c | DAP10 |
| TAG-72 | CD7 | b2c | DAP12 |
| TAG-72 | CD7 | b2c | CD32 |
| TAG-72 | CD7 | b2c | CD79a |
| TAG-72 | CD7 | b2c | CD79b |
| TAG-72 | CD7 | CD137/41BB | CD8 |
| TAG-72 | CD7 | CD137/41BB | CD3ζ |
| TAG-72 | CD7 | CD137/41BB | CD3δ |
| TAG-72 | CD7 | CD137/41BB | CD3γ |
| TAG-72 | CD7 | CD137/41BB | CD3ε |
| TAG-72 | CD7 | CD137/41BB | FcγRI-γ |
| TAG-72 | CD7 | CD137/41BB | FcγRIII-γ |
| TAG-72 | CD7 | CD137/41BB | FcεRIβ |
| TAG-72 | CD7 | CD137/41BB | FcεRIγ |
| TAG-72 | CD7 | CD137/41BB | DAP10 |
| TAG-72 | CD7 | CD137/41BB | DAP12 |
| TAG-72 | CD7 | CD137/41BB | CD32 |
| TAG-72 | CD7 | CD137/41BB | CD79a |
| TAG-72 | CD7 | CD137/41BB | CD79b |
| TAG-72 | CD7 | ICOS | CD8 |
| TAG-72 | CD7 | ICOS | CD3ζ |
| TAG-72 | CD7 | ICOS | CD3δ |
| TAG-72 | CD7 | ICOS | CD3γ |
| TAG-72 | CD7 | ICOS | CD3ε |
| TAG-72 | CD7 | ICOS | FcγRI-γ |
| TAG-72 | CD7 | ICOS | FcγRIII-γ |
| TAG-72 | CD7 | ICOS | FcεRIβ |
| TAG-72 | CD7 | ICOS | FcεRIγ |
| TAG-72 | CD7 | ICOS | DAP10 |
| TAG-72 | CD7 | ICOS | DAP12 |
| TAG-72 | CD7 | ICOS | CD32 |
| TAG-72 | CD7 | ICOS | CD79a |
| TAG-72 | CD7 | ICOS | CD79b |
| TAG-72 | CD7 | CD27 | CD8 |
| TAG-72 | CD7 | CD27 | CD3ζ |
| TAG-72 | CD7 | CD27 | CD3δ |
| TAG-72 | CD7 | CD27 | CD3γ |
| TAG-72 | CD7 | CD27 | CD3ε |
| TAG-72 | CD7 | CD27 | FcγRI-γ |
| TAG-72 | CD7 | CD27 | FcγRIII-γ |
| TAG-72 | CD7 | CD27 | FcεRIβ |
| TAG-72 | CD7 | CD27 | FcεRIγ |
| TAG-72 | CD7 | CD27 | DAP10 |
| TAG-72 | CD7 | CD27 | DAP12 |
| TAG-72 | CD7 | CD27 | CD32 |
| TAG-72 | CD7 | CD27 | CD79a |
| TAG-72 | CD7 | CD27 | CD79b |
| TAG-72 | CD7 | CD28δ | CD8 |
| TAG-72 | CD7 | CD28δ | CD3ζ |
| TAG-72 | CD7 | CD28δ | CD3δ |
| TAG-72 | CD7 | CD28δ | CD3γ |
| TAG-72 | CD7 | CD28δ | CD3ε |
| TAG-72 | CD7 | CD28δ | FcγRI-γ |
| TAG-72 | CD7 | CD28δ | FcγRIII-γ |
| TAG-72 | CD7 | CD28δ | FcεRIβ |
| TAG-72 | CD7 | CD28δ | FcεRIγ |
| TAG-72 | CD7 | CD28δ | DAP10 |
| TAG-72 | CD7 | CD28δ | DAP12 |
| TAG-72 | CD7 | CD28δ | CD32 |
| TAG-72 | CD7 | CD28δ | CD79a |
| TAG-72 | CD7 | CD28δ | CD79b |
| TAG-72 | CD7 | CD80 | CD8 |
| TAG-72 | CD7 | CD80 | CD3ζ |
| TAG-72 | CD7 | CD80 | CD3δ |
| TAG-72 | CD7 | CD80 | CD3γ |
| TAG-72 | CD7 | CD80 | CD3ε |
| TAG-72 | CD7 | CD80 | FcγRI-γ |

TABLE 3-continued

Third Generation CARs

| ScFv | Co-stimulatory Signal | Co-stimulatory Signal | Signal Domain |
|---|---|---|---|
| TAG-72 | CD7 | CD80 | FcγRIII-γ |
| TAG-72 | CD7 | CD80 | FcεRIβ |
| TAG-72 | CD7 | CD80 | FcεRIγ |
| TAG-72 | CD7 | CD80 | DAP10 |
| TAG-72 | CD7 | CD80 | DAP12 |
| TAG-72 | CD7 | CD80 | CD32 |
| TAG-72 | CD7 | CD80 | CD79a |
| TAG-72 | CD7 | CD80 | CD79b |
| TAG-72 | CD7 | CD86 | CD8 |
| TAG-72 | CD7 | CD86 | CD3ζ |
| TAG-72 | CD7 | CD86 | CD3δ |
| TAG-72 | CD7 | CD86 | CD3γ |
| TAG-72 | CD7 | CD86 | CD3ε |
| TAG-72 | CD7 | CD86 | FcγRI-γ |
| TAG-72 | CD7 | CD86 | FcγRIII-γ |
| TAG-72 | CD7 | CD86 | FcεRIβ |
| TAG-72 | CD7 | CD86 | FcεRIγ |
| TAG-72 | CD7 | CD86 | DAP10 |
| TAG-72 | CD7 | CD86 | DAP12 |
| TAG-72 | CD7 | CD86 | CD32 |
| TAG-72 | CD7 | CD86 | CD79a |
| TAG-72 | CD7 | CD86 | CD79b |
| TAG-72 | CD7 | OX40 | CD8 |
| TAG-72 | CD7 | OX40 | CD3ζ |
| TAG-72 | CD7 | OX40 | CD3δ |
| TAG-72 | CD7 | OX40 | CD3γ |
| TAG-72 | CD7 | OX40 | CD3ε |
| TAG-72 | CD7 | OX40 | FcγRI-γ |
| TAG-72 | CD7 | OX40 | FcγRIII-γ |
| TAG-72 | CD7 | OX40 | FcεRIβ |
| TAG-72 | CD7 | OX40 | FcεRIγ |
| TAG-72 | CD7 | OX40 | DAP10 |
| TAG-72 | CD7 | OX40 | DAP12 |
| TAG-72 | CD7 | OX40 | CD32 |
| TAG-72 | CD7 | OX40 | CD79a |
| TAG-72 | CD7 | OX40 | CD79b |
| TAG-72 | CD7 | DAP10 | CD8 |
| TAG-72 | CD7 | DAP10 | CD3ζ |
| TAG-72 | CD7 | DAP10 | CD3δ |
| TAG-72 | CD7 | DAP10 | CD3γ |
| TAG-72 | CD7 | DAP10 | CD3ε |
| TAG-72 | CD7 | DAP10 | FcγRI-γ |
| TAG-72 | CD7 | DAP10 | FcγRIII-γ |
| TAG-72 | CD7 | DAP10 | FcεRIβ |
| TAG-72 | CD7 | DAP10 | FcεRIγ |
| TAG-72 | CD7 | DAP10 | DAP10 |
| TAG-72 | CD7 | DAP10 | DAP12 |
| TAG-72 | CD7 | DAP10 | CD32 |
| TAG-72 | CD7 | DAP10 | CD79a |
| TAG-72 | CD7 | DAP10 | CD79b |
| TAG-72 | CD7 | DAP12 | CD8 |
| TAG-72 | CD7 | DAP12 | CD3ζ |
| TAG-72 | CD7 | DAP12 | CD3δ |
| TAG-72 | CD7 | DAP12 | CD3γ |
| TAG-72 | CD7 | DAP12 | CD3ε |
| TAG-72 | CD7 | DAP12 | FcγRI-γ |
| TAG-72 | CD7 | DAP12 | FcγRIII-γ |
| TAG-72 | CD7 | DAP12 | FcεRIβ |
| TAG-72 | CD7 | DAP12 | FcεRIγ |
| TAG-72 | CD7 | DAP12 | DAP10 |
| TAG-72 | CD7 | DAP12 | DAP12 |
| TAG-72 | CD7 | DAP12 | CD32 |
| TAG-72 | CD7 | DAP12 | CD79a |
| TAG-72 | CD7 | DAP12 | CD79b |
| TAG-72 | CD7 | MyD88 | CD8 |
| TAG-72 | CD7 | MyD88 | CD3ζ |
| TAG-72 | CD7 | MyD88 | CD3δ |
| TAG-72 | CD7 | MyD88 | CD3γ |
| TAG-72 | CD7 | MyD88 | CD3ε |
| TAG-72 | CD7 | MyD88 | FcγRI-γ |
| TAG-72 | CD7 | MyD88 | FcγRIII-γ |
| TAG-72 | CD7 | MyD88 | FcεRIβ |
| TAG-72 | CD7 | MyD88 | FcεRIγ |
| TAG-72 | CD7 | MyD88 | DAP10 |
| TAG-72 | CD7 | MyD88 | DAP12 |
| TAG-72 | CD7 | MyD88 | CD32 |
| TAG-72 | CD7 | MyD88 | CD79a |
| TAG-72 | CD7 | MyD88 | CD79b |
| TAG-72 | CD7 | CD7 | CD8 |
| TAG-72 | CD7 | CD7 | CD3ζ |
| TAG-72 | CD7 | CD7 | CD3δ |
| TAG-72 | CD7 | CD7 | CD3γ |
| TAG-72 | CD7 | CD7 | CD3ε |
| TAG-72 | CD7 | CD7 | FcγRI-γ |
| TAG-72 | CD7 | CD7 | FcγRIII-γ |
| TAG-72 | CD7 | CD7 | FcεRIβ |
| TAG-72 | CD7 | CD7 | FcεRIγ |
| TAG-72 | CD7 | CD7 | DAP10 |
| TAG-72 | CD7 | CD7 | DAP12 |
| TAG-72 | CD7 | CD7 | CD32 |
| TAG-72 | CD7 | CD7 | CD79a |
| TAG-72 | CD7 | CD7 | CD79b |
| TAG-72 | CD7 | BTNL3 | CD8 |
| TAG-72 | CD7 | BTNL3 | CD3ζ |
| TAG-72 | CD7 | BTNL3 | CD3δ |
| TAG-72 | CD7 | BTNL3 | CD3γ |
| TAG-72 | CD7 | BTNL3 | CD3ε |
| TAG-72 | CD7 | BTNL3 | FcγRI-γ |
| TAG-72 | CD7 | BTNL3 | FcγRIII-γ |
| TAG-72 | CD7 | BTNL3 | FcεRIβ |
| TAG-72 | CD7 | BTNL3 | FcεRIγ |
| TAG-72 | CD7 | BTNL3 | DAP10 |
| TAG-72 | CD7 | BTNL3 | DAP12 |
| TAG-72 | CD7 | BTNL3 | CD32 |
| TAG-72 | CD7 | BTNL3 | CD79a |
| TAG-72 | CD7 | BTNL3 | CD79b |
| TAG-72 | CD7 | NKG2D | CD8 |
| TAG-72 | CD7 | NKG2D | CD3ζ |
| TAG-72 | CD7 | NKG2D | CD3δ |
| TAG-72 | CD7 | NKG2D | CD3γ |
| TAG-72 | CD7 | NKG2D | CD3ε |
| TAG-72 | CD7 | NKG2D | FcγRI-γ |
| TAG-72 | CD7 | NKG2D | FcγRIII-γ |
| TAG-72 | CD7 | NKG2D | FcεRIβ |
| TAG-72 | CD7 | NKG2D | FcεRIγ |
| TAG-72 | CD7 | NKG2D | DAP10 |
| TAG-72 | CD7 | NKG2D | DAP12 |
| TAG-72 | CD7 | NKG2D | CD32 |
| TAG-72 | CD7 | NKG2D | CD79a |
| TAG-72 | CD7 | NKG2D | CD79b |
| TAG-72 | BTNL3 | CD28 | CD8 |
| TAG-72 | BTNL3 | CD28 | CD3ζ |
| TAG-72 | BTNL3 | CD28 | CD3δ |
| TAG-72 | BTNL3 | CD28 | CD3γ |
| TAG-72 | BTNL3 | CD28 | CD3ε |
| TAG-72 | BTNL3 | CD28 | FcγRI-γ |
| TAG-72 | BTNL3 | CD28 | FcγRIII-γ |
| TAG-72 | BTNL3 | CD28 | FcεRIβ |
| TAG-72 | BTNL3 | CD28 | FcεRIγ |
| TAG-72 | BTNL3 | CD28 | DAP10 |
| TAG-72 | BTNL3 | CD28 | DAP12 |
| TAG-72 | BTNL3 | CD28 | CD32 |
| TAG-72 | BTNL3 | CD28 | CD79a |
| TAG-72 | BTNL3 | CD28 | CD79b |
| TAG-72 | BTNL3 | CD8 | CD8 |
| TAG-72 | BTNL3 | CD8 | CD3ζ |
| TAG-72 | BTNL3 | CD8 | CD3δ |
| TAG-72 | BTNL3 | CD8 | CD3γ |
| TAG-72 | BTNL3 | CD8 | CD3ε |
| TAG-72 | BTNL3 | CD8 | FcγRI-γ |
| TAG-72 | BTNL3 | CD8 | FcγRIII-γ |
| TAG-72 | BTNL3 | CD8 | FcεRIβ |
| TAG-72 | BTNL3 | CD8 | FcεRIγ |
| TAG-72 | BTNL3 | CD8 | DAP10 |
| TAG-72 | BTNL3 | CD8 | DAP12 |
| TAG-72 | BTNL3 | CD8 | CD32 |
| TAG-72 | BTNL3 | CD8 | CD79a |
| TAG-72 | BTNL3 | CD8 | CD79b |
| TAG-72 | BTNL3 | CD4 | CD8 |
| TAG-72 | BTNL3 | CD4 | CD3ζ |

TABLE 3-continued

Third Generation CARs

| ScFv | Co-stimulatory Signal | Co-stimulatory Signal | Signal Domain |
|---|---|---|---|
| TAG-72 | BTNL3 | CD4 | CD3δ |
| TAG-72 | BTNL3 | CD4 | CD3γ |
| TAG-72 | BTNL3 | CD4 | CD3ε |
| TAG-72 | BTNL3 | CD4 | FcγRI-γ |
| TAG-72 | BTNL3 | CD4 | FcγRIII-γ |
| TAG-72 | BTNL3 | CD4 | FcεRIβ |
| TAG-72 | BTNL3 | CD4 | FcεRIγ |
| TAG-72 | BTNL3 | CD4 | DAP10 |
| TAG-72 | BTNL3 | CD4 | DAP12 |
| TAG-72 | BTNL3 | CD4 | CD32 |
| TAG-72 | BTNL3 | CD4 | CD79a |
| TAG-72 | BTNL3 | CD4 | CD79b |
| TAG-72 | BTNL3 | b2c | CD8 |
| TAG-72 | BTNL3 | b2c | CD3ζ |
| TAG-72 | BTNL3 | b2c | CD3δ |
| TAG-72 | BTNL3 | b2c | CD3γ |
| TAG-72 | BTNL3 | b2c | CD3ε |
| TAG-72 | BTNL3 | b2c | FcγRI-γ |
| TAG-72 | BTNL3 | b2c | FcγRIII-γ |
| TAG-72 | BTNL3 | b2c | FcεRIβ |
| TAG-72 | BTNL3 | b2c | FcεRIγ |
| TAG-72 | BTNL3 | b2c | DAP10 |
| TAG-72 | BTNL3 | b2c | DAP12 |
| TAG-72 | BTNL3 | b2c | CD32 |
| TAG-72 | BTNL3 | b2c | CD79a |
| TAG-72 | BTNL3 | b2c | CD79b |
| TAG-72 | BTNL3 | CD137/41BB | CD8 |
| TAG-72 | BTNL3 | CD137/41BB | CD3ζ |
| TAG-72 | BTNL3 | CD137/41BB | CD3δ |
| TAG-72 | BTNL3 | CD137/41BB | CD3γ |
| TAG-72 | BTNL3 | CD137/41BB | CD3ε |
| TAG-72 | BTNL3 | CD137/41BB | FcγRI-γ |
| TAG-72 | BTNL3 | CD137/41BB | FcγRIII-γ |
| TAG-72 | BTNL3 | CD137/41BB | FcεRIβ |
| TAG-72 | BTNL3 | CD137/41BB | FcεRIγ |
| TAG-72 | BTNL3 | CD137/41BB | DAP10 |
| TAG-72 | BTNL3 | CD137/41BB | DAP12 |
| TAG-72 | BTNL3 | CD137/41BB | CD32 |
| TAG-72 | BTNL3 | CD137/41BB | CD79a |
| TAG-72 | BTNL3 | CD137/41BB | CD79b |
| TAG-72 | BTNL3 | ICOS | CD8 |
| TAG-72 | BTNL3 | ICOS | CD3ζ |
| TAG-72 | BTNL3 | ICOS | CD3δ |
| TAG-72 | BTNL3 | ICOS | CD3γ |
| TAG-72 | BTNL3 | ICOS | CD3ε |
| TAG-72 | BTNL3 | ICOS | FcγRI-γ |
| TAG-72 | BTNL3 | ICOS | FcγRIII-γ |
| TAG-72 | BTNL3 | ICOS | FcεRIβ |
| TAG-72 | BTNL3 | ICOS | FcεRIγ |
| TAG-72 | BTNL3 | ICOS | DAP10 |
| TAG-72 | BTNL3 | ICOS | DAP12 |
| TAG-72 | BTNL3 | ICOS | CD32 |
| TAG-72 | BTNL3 | ICOS | CD79a |
| TAG-72 | BTNL3 | ICOS | CD79b |
| TAG-72 | BTNL3 | CD27 | CD8 |
| TAG-72 | BTNL3 | CD27 | CD3ζ |
| TAG-72 | BTNL3 | CD27 | CD3δ |
| TAG-72 | BTNL3 | CD27 | CD3γ |
| TAG-72 | BTNL3 | CD27 | CD3ε |
| TAG-72 | BTNL3 | CD27 | FcγRI-γ |
| TAG-72 | BTNL3 | CD27 | FcγRIII-γ |
| TAG-72 | BTNL3 | CD27 | FcεRIβ |
| TAG-72 | BTNL3 | CD27 | FcεRIγ |
| TAG-72 | BTNL3 | CD27 | DAP10 |
| TAG-72 | BTNL3 | CD27 | DAP12 |
| TAG-72 | BTNL3 | CD27 | CD32 |
| TAG-72 | BTNL3 | CD27 | CD79a |
| TAG-72 | BTNL3 | CD27 | CD79b |
| TAG-72 | BTNL3 | CD28δ | CD8 |
| TAG-72 | BTNL3 | CD28δ | CD3ζ |
| TAG-72 | BTNL3 | CD28δ | CD3δ |
| TAG-72 | BTNL3 | CD28δ | CD3γ |
| TAG-72 | BTNL3 | CD28δ | CD3ε |
| TAG-72 | BTNL3 | CD28δ | FcγRI-γ |
| TAG-72 | BTNL3 | CD28δ | FcγRIII-γ |
| TAG-72 | BTNL3 | CD28δ | FcεRIβ |
| TAG-72 | BTNL3 | CD28δ | FcεRIγ |
| TAG-72 | BTNL3 | CD28δ | DAP10 |
| TAG-72 | BTNL3 | CD28δ | DAP12 |
| TAG-72 | BTNL3 | CD28δ | CD32 |
| TAG-72 | BTNL3 | CD28δ | CD79a |
| TAG-72 | BTNL3 | CD28δ | CD79b |
| TAG-72 | BTNL3 | CD80 | CD8 |
| TAG-72 | BTNL3 | CD80 | CD3ζ |
| TAG-72 | BTNL3 | CD80 | CD3δ |
| TAG-72 | BTNL3 | CD80 | CD3γ |
| TAG-72 | BTNL3 | CD80 | CD3ε |
| TAG-72 | BTNL3 | CD80 | FcγRI-γ |
| TAG-72 | BTNL3 | CD80 | FcγRIII-γ |
| TAG-72 | BTNL3 | CD80 | FcεRIβ |
| TAG-72 | BTNL3 | CD80 | FcεRIγ |
| TAG-72 | BTNL3 | CD80 | DAP10 |
| TAG-72 | BTNL3 | CD80 | DAP12 |
| TAG-72 | BTNL3 | CD80 | CD32 |
| TAG-72 | BTNL3 | CD80 | CD79a |
| TAG-72 | BTNL3 | CD80 | CD79b |
| TAG-72 | BTNL3 | CD86 | CD8 |
| TAG-72 | BTNL3 | CD86 | CD3ζ |
| TAG-72 | BTNL3 | CD86 | CD3δ |
| TAG-72 | BTNL3 | CD86 | CD3γ |
| TAG-72 | BTNL3 | CD86 | CD3ε |
| TAG-72 | BTNL3 | CD86 | FcγRI-γ |
| TAG-72 | BTNL3 | CD86 | FcγRIII-γ |
| TAG-72 | BTNL3 | CD86 | FcεRIβ |
| TAG-72 | BTNL3 | CD86 | FcεRIγ |
| TAG-72 | BTNL3 | CD86 | DAP10 |
| TAG-72 | BTNL3 | CD86 | DAP12 |
| TAG-72 | BTNL3 | CD86 | CD32 |
| TAG-72 | BTNL3 | CD86 | CD79a |
| TAG-72 | BTNL3 | CD86 | CD79b |
| TAG-72 | BTNL3 | OX40 | CD8 |
| TAG-72 | BTNL3 | OX40 | CD3ζ |
| TAG-72 | BTNL3 | OX40 | CD3δ |
| TAG-72 | BTNL3 | OX40 | CD3γ |
| TAG-72 | BTNL3 | OX40 | CD3ε |
| TAG-72 | BTNL3 | OX40 | FcγRI-γ |
| TAG-72 | BTNL3 | OX40 | FcγRIII-γ |
| TAG-72 | BTNL3 | OX40 | FcεRIβ |
| TAG-72 | BTNL3 | OX40 | FcεRIγ |
| TAG-72 | BTNL3 | OX40 | DAP10 |
| TAG-72 | BTNL3 | OX40 | DAP12 |
| TAG-72 | BTNL3 | OX40 | CD32 |
| TAG-72 | BTNL3 | OX40 | CD79a |
| TAG-72 | BTNL3 | OX40 | CD79b |
| TAG-72 | BTNL3 | DAP10 | CD8 |
| TAG-72 | BTNL3 | DAP10 | CD3ζ |
| TAG-72 | BTNL3 | DAP10 | CD3δ |
| TAG-72 | BTNL3 | DAP10 | CD3γ |
| TAG-72 | BTNL3 | DAP10 | CD3ε |
| TAG-72 | BTNL3 | DAP10 | FcγRI-γ |
| TAG-72 | BTNL3 | DAP10 | FcγRIII-γ |
| TAG-72 | BTNL3 | DAP10 | FcεRIβ |
| TAG-72 | BTNL3 | DAP10 | FcεRIγ |
| TAG-72 | BTNL3 | DAP10 | DAP10 |
| TAG-72 | BTNL3 | DAP10 | DAP12 |
| TAG-72 | BTNL3 | DAP10 | CD32 |
| TAG-72 | BTNL3 | DAP10 | CD79a |
| TAG-72 | BTNL3 | DAP10 | CD79b |
| TAG-72 | BTNL3 | DAP12 | CD8 |
| TAG-72 | BTNL3 | DAP12 | CD3ζ |
| TAG-72 | BTNL3 | DAP12 | CD3δ |
| TAG-72 | BTNL3 | DAP12 | CD3γ |
| TAG-72 | BTNL3 | DAP12 | CD3ε |
| TAG-72 | BTNL3 | DAP12 | FcγRI-γ |
| TAG-72 | BTNL3 | DAP12 | FcγRIII-γ |
| TAG-72 | BTNL3 | DAP12 | FcεRIβ |
| TAG-72 | BTNL3 | DAP12 | FcεRIγ |
| TAG-72 | BTNL3 | DAP12 | DAP10 |
| TAG-72 | BTNL3 | DAP12 | DAP12 |
| TAG-72 | BTNL3 | DAP12 | CD32 |

TABLE 3-continued

Third Generation CARs

| ScFv | Co-stimulatory Signal | Co-stimulatory Signal | Signal Domain |
|---|---|---|---|
| TAG-72 | BTNL3 | DAP12 | CD79a |
| TAG-72 | BTNL3 | DAP12 | CD79b |
| TAG-72 | BTNL3 | MyD88 | CD8 |
| TAG-72 | BTNL3 | MyD88 | CD3ζ |
| TAG-72 | BTNL3 | MyD88 | CD3δ |
| TAG-72 | BTNL3 | MyD88 | CD3γ |
| TAG-72 | BTNL3 | MyD88 | CD3ε |
| TAG-72 | BTNL3 | MyD88 | FcγRI-γ |
| TAG-72 | BTNL3 | MyD88 | FcγRIII-γ |
| TAG-72 | BTNL3 | MyD88 | FcεRIβ |
| TAG-72 | BTNL3 | MyD88 | FcεRIγ |
| TAG-72 | BTNL3 | MyD88 | DAP10 |
| TAG-72 | BTNL3 | MyD88 | DAP12 |
| TAG-72 | BTNL3 | MyD88 | CD32 |
| TAG-72 | BTNL3 | MyD88 | CD79a |
| TAG-72 | BTNL3 | MyD88 | CD79b |
| TAG-72 | BTNL3 | CD7 | CD8 |
| TAG-72 | BTNL3 | CD7 | CD3ζ |
| TAG-72 | BTNL3 | CD7 | CD3δ |
| TAG-72 | BTNL3 | CD7 | CD3γ |
| TAG-72 | BTNL3 | CD7 | CD3ε |
| TAG-72 | BTNL3 | CD7 | FcγRI-γ |
| TAG-72 | BTNL3 | CD7 | FcγRIII-γ |
| TAG-72 | BTNL3 | CD7 | FcεRIβ |
| TAG-72 | BTNL3 | CD7 | FcεRIγ |
| TAG-72 | BTNL3 | CD7 | DAP10 |
| TAG-72 | BTNL3 | CD7 | DAP12 |
| TAG-72 | BTNL3 | CD7 | CD32 |
| TAG-72 | BTNL3 | CD7 | CD79a |
| TAG-72 | BTNL3 | CD7 | CD79b |
| TAG-72 | BTNL3 | BTNL3 | CD8 |
| TAG-72 | BTNL3 | BTNL3 | CD3ζ |
| TAG-72 | BTNL3 | BTNL3 | CD3δ |
| TAG-72 | BTNL3 | BTNL3 | CD3γ |
| TAG-72 | BTNL3 | BTNL3 | CD3ε |
| TAG-72 | BTNL3 | BTNL3 | FcγRI-γ |
| TAG-72 | BTNL3 | BTNL3 | FcγRIII-γ |
| TAG-72 | BTNL3 | BTNL3 | FcεRIβ |
| TAG-72 | BTNL3 | BTNL3 | FcεRIγ |
| TAG-72 | BTNL3 | BTNL3 | DAP10 |
| TAG-72 | BTNL3 | BTNL3 | DAP12 |
| TAG-72 | BTNL3 | BTNL3 | CD32 |
| TAG-72 | BTNL3 | BTNL3 | CD79a |
| TAG-72 | BTNL3 | BTNL3 | CD79b |
| TAG-72 | BTNL3 | NKG2D | CD8 |
| TAG-72 | BTNL3 | NKG2D | CD3ζ |
| TAG-72 | BTNL3 | NKG2D | CD3δ |
| TAG-72 | BTNL3 | NKG2D | CD3γ |
| TAG-72 | BTNL3 | NKG2D | CD3ε |
| TAG-72 | BTNL3 | NKG2D | FcγRI-γ |
| TAG-72 | BTNL3 | NKG2D | FcγRIII-γ |
| TAG-72 | BTNL3 | NKG2D | FcεRIβ |
| TAG-72 | BTNL3 | NKG2D | FcεRIγ |
| TAG-72 | BTNL3 | NKG2D | DAP10 |
| TAG-72 | BTNL3 | NKG2D | DAP12 |
| TAG-72 | BTNL3 | NKG2D | CD32 |
| TAG-72 | BTNL3 | NKG2D | CD79a |
| TAG-72 | BTNL3 | NKG2D | CD79b |
| TAG-72 | NKG2D | CD28 | CD8 |
| TAG-72 | NKG2D | CD28 | CD3ζ |
| TAG-72 | NKG2D | CD28 | CD3δ |
| TAG-72 | NKG2D | CD28 | CD3γ |
| TAG-72 | NKG2D | CD28 | CD3ε |
| TAG-72 | NKG2D | CD28 | FcγRI-γ |
| TAG-72 | NKG2D | CD28 | FcγRIII-γ |
| TAG-72 | NKG2D | CD28 | FcεRIβ |
| TAG-72 | NKG2D | CD28 | FcεRIγ |
| TAG-72 | NKG2D | CD28 | DAP10 |
| TAG-72 | NKG2D | CD28 | DAP12 |
| TAG-72 | NKG2D | CD28 | CD32 |
| TAG-72 | NKG2D | CD28 | CD79a |
| TAG-72 | NKG2D | CD28 | CD79b |
| TAG-72 | NKG2D | CD8 | CD8 |
| TAG-72 | NKG2D | CD8 | CD3ζ |
| TAG-72 | NKG2D | CD8 | CD3δ |
| TAG-72 | NKG2D | CD8 | CD3γ |
| TAG-72 | NKG2D | CD8 | CD3ε |
| TAG-72 | NKG2D | CD8 | FcγRI-γ |
| TAG-72 | NKG2D | CD8 | FcγRIII-γ |
| TAG-72 | NKG2D | CD8 | FcεRIβ |
| TAG-72 | NKG2D | CD8 | FcεRIγ |
| TAG-72 | NKG2D | CD8 | DAP10 |
| TAG-72 | NKG2D | CD8 | DAP12 |
| TAG-72 | NKG2D | CD8 | CD32 |
| TAG-72 | NKG2D | CD8 | CD79a |
| TAG-72 | NKG2D | CD8 | CD79b |
| TAG-72 | NKG2D | CD4 | CD8 |
| TAG-72 | NKG2D | CD4 | CD3ζ |
| TAG-72 | NKG2D | CD4 | CD3δ |
| TAG-72 | NKG2D | CD4 | CD3γ |
| TAG-72 | NKG2D | CD4 | CD3ε |
| TAG-72 | NKG2D | CD4 | FcγRI-γ |
| TAG-72 | NKG2D | CD4 | FcγRIII-γ |
| TAG-72 | NKG2D | CD4 | FcεRIβ |
| TAG-72 | NKG2D | CD4 | FcεRIγ |
| TAG-72 | NKG2D | CD4 | DAP10 |
| TAG-72 | NKG2D | CD4 | DAP12 |
| TAG-72 | NKG2D | CD4 | CD32 |
| TAG-72 | NKG2D | CD4 | CD79a |
| TAG-72 | NKG2D | CD4 | CD79b |
| TAG-72 | NKG2D | b2c | CD8 |
| TAG-72 | NKG2D | b2c | CD3ζ |
| TAG-72 | NKG2D | b2c | CD3δ |
| TAG-72 | NKG2D | b2c | CD3γ |
| TAG-72 | NKG2D | b2c | CD3ε |
| TAG-72 | NKG2D | b2c | FcγRI-γ |
| TAG-72 | NKG2D | b2c | FcγRIII-γ |
| TAG-72 | NKG2D | b2c | FcεRIβ |
| TAG-72 | NKG2D | b2c | FcεRIγ |
| TAG-72 | NKG2D | b2c | DAP10 |
| TAG-72 | NKG2D | b2c | DAP12 |
| TAG-72 | NKG2D | b2c | CD32 |
| TAG-72 | NKG2D | b2c | CD79a |
| TAG-72 | NKG2D | b2c | CD79b |
| TAG-72 | NKG2D | CD137/41BB | CD8 |
| TAG-72 | NKG2D | CD137/41BB | CD3ζ |
| TAG-72 | NKG2D | CD137/41BB | CD3δ |
| TAG-72 | NKG2D | CD137/41BB | CD3γ |
| TAG-72 | NKG2D | CD137/41BB | CD3ε |
| TAG-72 | NKG2D | CD137/41BB | FcγRI-γ |
| TAG-72 | NKG2D | CD137/41BB | FcγRIII-γ |
| TAG-72 | NKG2D | CD137/41BB | FcεRIβ |
| TAG-72 | NKG2D | CD137/41BB | FcεRIγ |
| TAG-72 | NKG2D | CD137/41BB | DAP10 |
| TAG-72 | NKG2D | CD137/41BB | DAP12 |
| TAG-72 | NKG2D | CD137/41BB | CD32 |
| TAG-72 | NKG2D | CD137/41BB | CD79a |
| TAG-72 | NKG2D | CD137/41BB | CD79b |
| TAG-72 | NKG2D | ICOS | CD8 |
| TAG-72 | NKG2D | ICOS | CD3ζ |
| TAG-72 | NKG2D | ICOS | CD3δ |
| TAG-72 | NKG2D | ICOS | CD3γ |
| TAG-72 | NKG2D | ICOS | CD3ε |
| TAG-72 | NKG2D | ICOS | FcγRI-γ |
| TAG-72 | NKG2D | ICOS | FcγRIII-γ |
| TAG-72 | NKG2D | ICOS | FcεRIβ |
| TAG-72 | NKG2D | ICOS | FcεRIγ |
| TAG-72 | NKG2D | ICOS | DAP10 |
| TAG-72 | NKG2D | ICOS | DAP12 |
| TAG-72 | NKG2D | ICOS | CD32 |
| TAG-72 | NKG2D | ICOS | CD79a |
| TAG-72 | NKG2D | ICOS | CD79b |
| TAG-72 | NKG2D | CD27 | CD8 |
| TAG-72 | NKG2D | CD27 | CD3ζ |
| TAG-72 | NKG2D | CD27 | CD3δ |
| TAG-72 | NKG2D | CD27 | CD3γ |
| TAG-72 | NKG2D | CD27 | CD3ε |
| TAG-72 | NKG2D | CD27 | FcγRI-γ |
| TAG-72 | NKG2D | CD27 | FcγRIII-γ |
| TAG-72 | NKG2D | CD27 | FcεRIβ |

TABLE 3-continued

Third Generation CARs

| ScFv | Co-stimulatory Signal | Co-stimulatory Signal | Signal Domain |
|---|---|---|---|
| TAG-72 | NKG2D | CD27 | FcεRIγ |
| TAG-72 | NKG2D | CD27 | DAP10 |
| TAG-72 | NKG2D | CD27 | DAP12 |
| TAG-72 | NKG2D | CD27 | CD32 |
| TAG-72 | NKG2D | CD27 | CD79a |
| TAG-72 | NKG2D | CD27 | CD79b |
| TAG-72 | NKG2D | CD28δ | CD8 |
| TAG-72 | NKG2D | CD28δ | CD3ζ |
| TAG-72 | NKG2D | CD28δ | CD3δ |
| TAG-72 | NKG2D | CD28δ | CD3γ |
| TAG-72 | NKG2D | CD28δ | CD3ε |
| TAG-72 | NKG2D | CD28δ | FcγRI-γ |
| TAG-72 | NKG2D | CD28δ | FcγRIII-γ |
| TAG-72 | NKG2D | CD28δ | FcεRIβ |
| TAG-72 | NKG2D | CD28δ | FcεRIγ |
| TAG-72 | NKG2D | CD28δ | DAP10 |
| TAG-72 | NKG2D | CD28δ | DAP12 |
| TAG-72 | NKG2D | CD28δ | CD32 |
| TAG-72 | NKG2D | CD28δ | CD79a |
| TAG-72 | NKG2D | CD28δ | CD79b |
| TAG-72 | NKG2D | CD80 | CD8 |
| TAG-72 | NKG2D | CD80 | CD3ζ |
| TAG-72 | NKG2D | CD80 | CD3δ |
| TAG-72 | NKG2D | CD80 | CD3γ |
| TAG-72 | NKG2D | CD80 | CD3ε |
| TAG-72 | NKG2D | CD80 | FcγRI-γ |
| TAG-72 | NKG2D | CD80 | FcγRIII-γ |
| TAG-72 | NKG2D | CD80 | FcεRIβ |
| TAG-72 | NKG2D | CD80 | FcεRIγ |
| TAG-72 | NKG2D | CD80 | DAP10 |
| TAG-72 | NKG2D | CD80 | DAP12 |
| TAG-72 | NKG2D | CD80 | CD32 |
| TAG-72 | NKG2D | CD80 | CD79a |
| TAG-72 | NKG2D | CD80 | CD79b |
| TAG-72 | NKG2D | CD86 | CD8 |
| TAG-72 | NKG2D | CD86 | CD3ζ |
| TAG-72 | NKG2D | CD86 | CD3δ |
| TAG-72 | NKG2D | CD86 | CD3γ |
| TAG-72 | NKG2D | CD86 | CD3ε |
| TAG-72 | NKG2D | CD86 | FcγRI-γ |
| TAG-72 | NKG2D | CD86 | FcγRIII-γ |
| TAG-72 | NKG2D | CD86 | FcεRIβ |
| TAG-72 | NKG2D | CD86 | FcεRIγ |
| TAG-72 | NKG2D | CD86 | DAP10 |
| TAG-72 | NKG2D | CD86 | DAP12 |
| TAG-72 | NKG2D | CD86 | CD32 |
| TAG-72 | NKG2D | CD86 | CD79a |
| TAG-72 | NKG2D | CD86 | CD79b |
| TAG-72 | NKG2D | OX40 | CD8 |
| TAG-72 | NKG2D | OX40 | CD3ζ |
| TAG-72 | NKG2D | OX40 | CD3δ |
| TAG-72 | NKG2D | OX40 | CD3γ |
| TAG-72 | NKG2D | OX40 | CD3ε |
| TAG-72 | NKG2D | OX40 | FcγRI-γ |
| TAG-72 | NKG2D | OX40 | FcγRIII-γ |
| TAG-72 | NKG2D | OX40 | FcεRIβ |
| TAG-72 | NKG2D | OX40 | FcεRIγ |
| TAG-72 | NKG2D | OX40 | DAP10 |
| TAG-72 | NKG2D | OX40 | DAP12 |
| TAG-72 | NKG2D | OX40 | CD32 |
| TAG-72 | NKG2D | OX40 | CD79a |
| TAG-72 | NKG2D | OX40 | CD79b |
| TAG-72 | NKG2D | DAP10 | CD8 |
| TAG-72 | NKG2D | DAP10 | CD3ζ |
| TAG-72 | NKG2D | DAP10 | CD3δ |
| TAG-72 | NKG2D | DAP10 | CD3γ |
| TAG-72 | NKG2D | DAP10 | CD3ε |
| TAG-72 | NKG2D | DAP10 | FcγRI-γ |
| TAG-72 | NKG2D | DAP10 | FcγRIII-γ |
| TAG-72 | NKG2D | DAP10 | FcεRIβ |
| TAG-72 | NKG2D | DAP10 | FcεRIγ |
| TAG-72 | NKG2D | DAP10 | DAP10 |
| TAG-72 | NKG2D | DAP10 | DAP12 |
| TAG-72 | NKG2D | DAP10 | CD32 |
| TAG-72 | NKG2D | DAP10 | CD79a |
| TAG-72 | NKG2D | DAP10 | CD79b |
| TAG-72 | NKG2D | DAP12 | CD8 |
| TAG-72 | NKG2D | DAP12 | CD3ζ |
| TAG-72 | NKG2D | DAP12 | CD3δ |
| TAG-72 | NKG2D | DAP12 | CD3γ |
| TAG-72 | NKG2D | DAP12 | CD3ε |
| TAG-72 | NKG2D | DAP12 | FcγRI-γ |
| TAG-72 | NKG2D | DAP12 | FcγRIII-γ |
| TAG-72 | NKG2D | DAP12 | FcεRIβ |
| TAG-72 | NKG2D | DAP12 | FcεRIγ |
| TAG-72 | NKG2D | DAP12 | DAP10 |
| TAG-72 | NKG2D | DAP12 | DAP12 |
| TAG-72 | NKG2D | DAP12 | CD32 |
| TAG-72 | NKG2D | DAP12 | CD79a |
| TAG-72 | NKG2D | DAP12 | CD79b |
| TAG-72 | NKG2D | MyD88 | CD8 |
| TAG-72 | NKG2D | MyD88 | CD3ζ |
| TAG-72 | NKG2D | MyD88 | CD3δ |
| TAG-72 | NKG2D | MyD88 | CD3γ |
| TAG-72 | NKG2D | MyD88 | CD3ε |
| TAG-72 | NKG2D | MyD88 | FcγRI-γ |
| TAG-72 | NKG2D | MyD88 | FcγRIII-γ |
| TAG-72 | NKG2D | MyD88 | FcεRIβ |
| TAG-72 | NKG2D | MyD88 | FcεRIγ |
| TAG-72 | NKG2D | MyD88 | DAP10 |
| TAG-72 | NKG2D | MyD88 | DAP12 |
| TAG-72 | NKG2D | MyD88 | CD32 |
| TAG-72 | NKG2D | MyD88 | CD79a |
| TAG-72 | NKG2D | MyD88 | CD79b |
| TAG-72 | NKG2D | CD7 | CD8 |
| TAG-72 | NKG2D | CD7 | CD3ζ |
| TAG-72 | NKG2D | CD7 | CD3δ |
| TAG-72 | NKG2D | CD7 | CD3γ |
| TAG-72 | NKG2D | CD7 | CD3ε |
| TAG-72 | NKG2D | CD7 | FcγRI-γ |
| TAG-72 | NKG2D | CD7 | FcγRIII-γ |
| TAG-72 | NKG2D | CD7 | FcεRIβ |
| TAG-72 | NKG2D | CD7 | FcεRIγ |
| TAG-72 | NKG2D | CD7 | DAP10 |
| TAG-72 | NKG2D | CD7 | DAP12 |
| TAG-72 | NKG2D | CD7 | CD32 |
| TAG-72 | NKG2D | CD7 | CD79a |
| TAG-72 | NKG2D | CD7 | CD79b |
| TAG-72 | NKG2D | BTNL3 | CD8 |
| TAG-72 | NKG2D | BTNL3 | CD3ζ |
| TAG-72 | NKG2D | BTNL3 | CD3δ |
| TAG-72 | NKG2D | BTNL3 | CD3γ |
| TAG-72 | NKG2D | BTNL3 | CD3ε |
| TAG-72 | NKG2D | BTNL3 | FcγRI-γ |
| TAG-72 | NKG2D | BTNL3 | FcγRIII-γ |
| TAG-72 | NKG2D | BTNL3 | FcεRIβ |
| TAG-72 | NKG2D | BTNL3 | FcεRIγ |
| TAG-72 | NKG2D | BTNL3 | DAP10 |
| TAG-72 | NKG2D | BTNL3 | DAP12 |
| TAG-72 | NKG2D | BTNL3 | CD32 |
| TAG-72 | NKG2D | BTNL3 | CD79a |
| TAG-72 | NKG2D | BTNL3 | CD79b |
| TAG-72 | NKG2D | NKG2D | CD8 |
| TAG-72 | NKG2D | NKG2D | CD3ζ |
| TAG-72 | NKG2D | NKG2D | CD3δ |
| TAG-72 | NKG2D | NKG2D | CD3γ |
| TAG-72 | NKG2D | NKG2D | CD3ε |
| TAG-72 | NKG2D | NKG2D | FcγRI-γ |
| TAG-72 | NKG2D | NKG2D | FcγRIII-γ |
| TAG-72 | NKG2D | NKG2D | FcεRIβ |
| TAG-72 | NKG2D | NKG2D | FcεRIγ |
| TAG-72 | NKG2D | NKG2D | DAP10 |
| TAG-72 | NKG2D | NKG2D | DAP12 |
| TAG-72 | NKG2D | NKG2D | CD32 |
| TAG-72 | NKG2D | NKG2D | CD79a |
| TAG-72 | NKG2D | NKG2D | CD79b |

TABLE 4

CARs lacking Co-Simulatory Signal (for dual CAR approach)

| ScFv | Co-stimulatory Signal | Signal Domain |
|---|---|---|
| TAG-72 | none | CD8 |
| TAG-72 | none | CD3ζ |
| TAG-72 | none | CD3δ |
| TAG-72 | none | CD3γ |
| TAG-72 | none | CD3ε |
| TAG-72 | none | FcγRI-γ |
| TAG-72 | none | FcγRIII-γ |
| TAG-72 | none | FcεRIβ |
| TAG-72 | none | FcεRIγ |
| TAG-72 | none | DAP10 |
| TAG-72 | none | DAP12 |
| TAG-72 | none | CD32 |
| TAG-72 | none | CD79a |
| TAG-72 | none | CD8 |
| TAG-72 | none | CD3ζ |
| TAG-72 | none | CD3δ |
| TAG-72 | none | CD3γ |
| TAG-72 | none | CD3ε |
| TAG-72 | none | FcγRI-γ |

TABLE 5

CARs lacking Signal Domain (for dual CAR approach)

| ScFv | Co-stimulatory Signal | Signal Domain |
|---|---|---|
| TAG-72 | CD28 | none |
| TAG-72 | CD8 | none |
| TAG-72 | CD4 | none |
| TAG-72 | b2c | none |
| TAG-72 | CD137/41BB | none |
| TAG-72 | ICOS | none |
| TAG-72 | CD27 | none |
| TAG-72 | CD28δ | none |
| TAG-72 | CD80 | none |
| TAG-72 | CD86 | none |
| TAG-72 | OX40 | none |
| TAG-72 | DAP10 | none |
| TAG-72 | MyD88 | none |
| TAG-72 | CD7 | none |
| TAG-72 | DAP12 | none |
| TAG-72 | MyD88 | none |
| TAG-72 | CD7 | none |
| TAG-72 | BTNL3 | none |
| TAG-72 | NKG2D | none |

TABLE 6

Third Generation CARs lacking Signal Domain (for dual CAR approach)

| ScFv | Co-stimulatory Signal | Co-stimulatory Signal | Signal Domain |
|---|---|---|---|
| TAG-72 | CD28 | CD28 | none |
| TAG-72 | CD28 | CD8 | none |
| TAG-72 | CD28 | CD4 | none |
| TAG-72 | CD28 | b2c | none |
| TAG-72 | CD28 | CD137/41BB | none |
| TAG-72 | CD28 | ICOS | none |
| TAG-72 | CD28 | CD27 | none |
| TAG-72 | CD28 | CD28δ | none |
| TAG-72 | CD28 | CD80 | none |
| TAG-72 | CD28 | CD86 | none |
| TAG-72 | CD28 | OX40 | none |
| TAG-72 | CD28 | DAP10 | none |
| TAG-72 | CD28 | MyD88 | none |
| TAG-72 | CD28 | CD7 | none |
| TAG-72 | CD28 | DAP12 | none |
| TAG-72 | CD28 | MyD88 | none |
| TAG-72 | CD28 | CD7 | none |
| TAG-72 | CD8 | CD28 | none |
| TAG-72 | CD8 | CD8 | none |
| TAG-72 | CD8 | CD4 | none |
| TAG-72 | CD8 | b2c | none |
| TAG-72 | CD8 | CD137/41BB | none |
| TAG-72 | CD8 | ICOS | none |
| TAG-72 | CD8 | CD27 | none |
| TAG-72 | CD8 | CD28δ | none |
| TAG-72 | CD8 | CD80 | none |
| TAG-72 | CD8 | CD86 | none |
| TAG-72 | CD8 | OX40 | none |
| TAG-72 | CD8 | DAP10 | none |
| TAG-72 | CD8 | MyD88 | none |
| TAG-72 | CD8 | CD7 | none |
| TAG-72 | CD8 | DAP12 | none |
| TAG-72 | CD8 | MyD88 | none |
| TAG-72 | CD8 | CD7 | none |
| TAG-72 | CD4 | CD28 | none |
| TAG-72 | CD4 | CD8 | none |
| TAG-72 | CD4 | CD4 | none |
| TAG-72 | CD4 | b2c | none |
| TAG-72 | CD4 | CD137/41BB | none |
| TAG-72 | CD4 | ICOS | none |
| TAG-72 | CD4 | CD27 | none |
| TAG-72 | CD4 | CD28δ | none |
| TAG-72 | CD4 | CD80 | none |
| TAG-72 | CD4 | CD86 | none |
| TAG-72 | CD4 | OX40 | none |
| TAG-72 | CD4 | DAP10 | none |
| TAG-72 | CD4 | MyD88 | none |
| TAG-72 | CD4 | CD7 | none |
| TAG-72 | CD4 | DAP12 | none |
| TAG-72 | CD4 | MyD88 | none |
| TAG-72 | CD4 | CD7 | none |
| TAG-72 | b2c | CD28 | none |
| TAG-72 | b2c | CD8 | none |
| TAG-72 | b2c | CD4 | none |
| TAG-72 | b2c | b2c | none |
| TAG-72 | b2c | CD137/41BB | none |
| TAG-72 | b2c | ICOS | none |
| TAG-72 | b2c | CD27 | none |
| TAG-72 | b2c | CD28δ | none |
| TAG-72 | b2c | CD80 | none |
| TAG-72 | b2c | CD86 | none |
| TAG-72 | b2c | OX40 | none |
| TAG-72 | b2c | DAP10 | none |
| TAG-72 | b2c | MyD88 | none |
| TAG-72 | b2c | CD7 | none |
| TAG-72 | b2c | DAP12 | none |
| TAG-72 | b2c | MyD88 | none |
| TAG-72 | b2c | CD7 | none |
| TAG-72 | CD137/41BB | CD28 | none |
| TAG-72 | CD137/41BB | CD8 | none |
| TAG-72 | CD137/41BB | CD4 | none |
| TAG-72 | CD137/41BB | b2c | none |
| TAG-72 | CD137/41BB | CD137/41BB | none |
| TAG-72 | CD137/41BB | ICOS | none |
| TAG-72 | CD137/41BB | CD27 | none |
| TAG-72 | CD137/41BB | CD28δ | none |
| TAG-72 | CD137/41BB | CD80 | none |
| TAG-72 | CD137/41BB | CD86 | none |
| TAG-72 | CD137/41BB | OX40 | none |
| TAG-72 | CD137/41BB | DAP10 | none |
| TAG-72 | CD137/41BB | MyD88 | none |
| TAG-72 | CD137/41BB | CD7 | none |
| TAG-72 | CD137/41BB | DAP12 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| TAG-72 | CD137/41BB | MyD88 | none |
| TAG-72 | CD137/41BB | CD7 | none |
| TAG-72 | ICOS | CD28 | none |
| TAG-72 | ICOS | CD8 | none |
| TAG-72 | ICOS | CD4 | none |
| TAG-72 | ICOS | b2c | none |
| TAG-72 | ICOS | CD137/41BB | none |
| TAG-72 | ICOS | ICOS | none |
| TAG-72 | ICOS | CD27 | none |
| TAG-72 | ICOS | CD28δ | none |
| TAG-72 | ICOS | CD80 | none |
| TAG-72 | ICOS | CD86 | none |
| TAG-72 | ICOS | OX40 | none |
| TAG-72 | ICOS | DAP10 | none |
| TAG-72 | ICOS | MyD88 | none |
| TAG-72 | ICOS | CD7 | none |
| TAG-72 | ICOS | DAP12 | none |
| TAG-72 | ICOS | MyD88 | none |
| TAG-72 | ICOS | CD7 | none |
| TAG-72 | ICOS | CD28 | none |
| TAG-72 | ICOS | CD8 | none |
| TAG-72 | ICOS | CD4 | none |
| TAG-72 | ICOS | b2c | none |
| TAG-72 | ICOS | CD137/41BB | none |
| TAG-72 | ICOS | ICOS | none |
| TAG-72 | ICOS | CD27 | none |
| TAG-72 | ICOS | CD28δ | none |
| TAG-72 | ICOS | CD80 | none |
| TAG-72 | ICOS | CD86 | none |
| TAG-72 | ICOS | OX40 | none |
| TAG-72 | ICOS | DAP10 | none |
| TAG-72 | ICOS | MyD88 | none |
| TAG-72 | ICOS | CD7 | none |
| TAG-72 | ICOS | DAP12 | none |
| TAG-72 | ICOS | MyD88 | none |
| TAG-72 | ICOS | CD7 | none |
| TAG-72 | CD27 | CD28 | none |
| TAG-72 | CD27 | CD8 | none |
| TAG-72 | CD27 | CD4 | none |
| TAG-72 | CD27 | b2c | none |
| TAG-72 | CD27 | CD137/41BB | none |
| TAG-72 | CD27 | ICOS | none |
| TAG-72 | CD27 | CD27 | none |
| TAG-72 | CD27 | CD28δ | none |
| TAG-72 | CD27 | CD80 | none |
| TAG-72 | CD27 | CD86 | none |
| TAG-72 | CD27 | OX40 | none |
| TAG-72 | CD27 | DAP10 | none |
| TAG-72 | CD27 | MyD88 | none |
| TAG-72 | CD27 | CD7 | none |
| TAG-72 | CD27 | DAP12 | none |
| TAG-72 | CD27 | MyD88 | none |
| TAG-72 | CD27 | CD7 | none |
| TAG-72 | CD28δ | CD28 | none |
| TAG-72 | CD28δ | CD8 | none |
| TAG-72 | CD28δ | CD4 | none |
| TAG-72 | CD28δ | b2c | none |
| TAG-72 | CD28δ | CD137/41BB | none |
| TAG-72 | CD28δ | ICOS | none |
| TAG-72 | CD28δ | CD27 | none |
| TAG-72 | CD28δ | CD28δ | none |
| TAG-72 | CD28δ | CD80 | none |
| TAG-72 | CD28δ | CD86 | none |
| TAG-72 | CD28δ | OX40 | none |
| TAG-72 | CD28δ | DAP10 | none |
| TAG-72 | CD28δ | MyD88 | none |
| TAG-72 | CD28δ | CD7 | none |
| TAG-72 | CD28δ | DAP12 | none |
| TAG-72 | CD28δ | MyD88 | none |
| TAG-72 | CD28δ | CD7 | none |
| TAG-72 | CD80 | CD28 | none |
| TAG-72 | CD80 | CD8 | none |
| TAG-72 | CD80 | CD4 | none |
| TAG-72 | CD80 | b2c | none |
| TAG-72 | CD80 | CD137/41BB | none |
| TAG-72 | CD80 | ICOS | none |
| TAG-72 | CD80 | CD27 | none |
| TAG-72 | CD80 | CD28δ | none |
| TAG-72 | CD80 | CD80 | none |
| TAG-72 | CD80 | CD86 | none |
| TAG-72 | CD80 | OX40 | none |
| TAG-72 | CD80 | DAP10 | none |
| TAG-72 | CD80 | MyD88 | none |
| TAG-72 | CD80 | CD7 | none |
| TAG-72 | CD80 | DAP12 | none |
| TAG-72 | CD80 | MyD88 | none |
| TAG-72 | CD80 | CD7 | none |
| TAG-72 | CD86 | CD28 | none |
| TAG-72 | CD86 | CD8 | none |
| TAG-72 | CD86 | CD4 | none |
| TAG-72 | CD86 | b2c | none |
| TAG-72 | CD86 | CD137/41BB | none |
| TAG-72 | CD86 | ICOS | none |
| TAG-72 | CD86 | CD27 | none |
| TAG-72 | CD86 | CD28δ | none |
| TAG-72 | CD86 | CD80 | none |
| TAG-72 | CD86 | CD86 | none |
| TAG-72 | CD86 | OX40 | none |
| TAG-72 | CD86 | DAP10 | none |
| TAG-72 | CD86 | MyD88 | none |
| TAG-72 | CD86 | CD7 | none |
| TAG-72 | CD86 | DAP12 | none |
| TAG-72 | CD86 | MyD88 | none |
| TAG-72 | CD86 | CD7 | none |
| TAG-72 | OX40 | CD28 | none |
| TAG-72 | OX40 | CD8 | none |
| TAG-72 | OX40 | CD4 | none |
| TAG-72 | OX40 | b2c | none |
| TAG-72 | OX40 | CD137/41BB | none |
| TAG-72 | OX40 | ICOS | none |
| TAG-72 | OX40 | CD27 | none |
| TAG-72 | OX40 | CD28δ | none |
| TAG-72 | OX40 | CD80 | none |
| TAG-72 | OX40 | CD86 | none |
| TAG-72 | OX40 | OX40 | none |
| TAG-72 | OX40 | DAP10 | none |
| TAG-72 | OX40 | MyD88 | none |
| TAG-72 | OX40 | CD7 | none |
| TAG-72 | OX40 | DAP12 | none |
| TAG-72 | OX40 | MyD88 | none |
| TAG-72 | OX40 | CD7 | none |
| TAG-72 | DAP10 | CD28 | none |
| TAG-72 | DAP10 | CD8 | none |
| TAG-72 | DAP10 | CD4 | none |
| TAG-72 | DAP10 | b2c | none |
| TAG-72 | DAP10 | CD137/41BB | none |
| TAG-72 | DAP10 | ICOS | none |
| TAG-72 | DAP10 | CD27 | none |
| TAG-72 | DAP10 | CD28δ | none |
| TAG-72 | DAP10 | CD80 | none |
| TAG-72 | DAP10 | CD86 | none |
| TAG-72 | DAP10 | OX40 | none |
| TAG-72 | DAP10 | DAP10 | none |
| TAG-72 | DAP10 | MyD88 | none |
| TAG-72 | DAP10 | CD7 | none |
| TAG-72 | DAP10 | DAP12 | none |
| TAG-72 | DAP10 | MyD88 | none |
| TAG-72 | DAP10 | CD7 | none |
| TAG-72 | DAP12 | CD28 | none |
| TAG-72 | DAP12 | CD8 | none |
| TAG-72 | DAP12 | CD4 | none |
| TAG-72 | DAP12 | b2c | none |
| TAG-72 | DAP12 | CD137/41BB | none |
| TAG-72 | DAP12 | ICOS | none |
| TAG-72 | DAP12 | CD27 | none |
| TAG-72 | DAP12 | CD28δ | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| TAG-72 | DAP12 | CD80 | none |
| TAG-72 | DAP12 | CD86 | none |
| TAG-72 | DAP12 | OX40 | none |
| TAG-72 | DAP12 | DAP10 | none |
| TAG-72 | DAP12 | MyD88 | none |
| TAG-72 | DAP12 | CD7 | none |
| TAG-72 | DAP12 | DAP12 | none |
| TAG-72 | DAP12 | MyD88 | none |
| TAG-72 | DAP12 | CD7 | none |
| TAG-72 | MyD88 | CD28 | none |
| TAG-72 | MyD88 | CD8 | none |
| TAG-72 | MyD88 | CD4 | none |
| TAG-72 | MyD88 | b2c | none |
| TAG-72 | MyD88 | CD137/41BB | none |
| TAG-72 | MyD88 | ICOS | none |
| TAG-72 | MyD88 | CD27 | none |
| TAG-72 | MyD88 | CD28δ | none |
| TAG-72 | MyD88 | CD80 | none |
| TAG-72 | MyD88 | CD86 | none |
| TAG-72 | MyD88 | OX40 | none |
| TAG-72 | MyD88 | DAP10 | none |
| TAG-72 | MyD88 | MyD88 | none |
| TAG-72 | MyD88 | CD7 | none |
| TAG-72 | MyD88 | DAP12 | none |
| TAG-72 | MyD88 | MyD88 | none |
| TAG-72 | MyD88 | CD7 | none |
| TAG-72 | CD7 | CD28 | none |
| TAG-72 | CD7 | CD8 | none |
| TAG-72 | CD7 | CD4 | none |
| TAG-72 | CD7 | b2c | none |
| TAG-72 | CD7 | CD137/41BB | none |
| TAG-72 | CD7 | ICOS | none |
| TAG-72 | CD7 | CD27 | none |
| TAG-72 | CD7 | CD28δ | none |
| TAG-72 | CD7 | CD80 | none |
| TAG-72 | CD7 | CD86 | none |
| TAG-72 | CD7 | OX40 | none |
| TAG-72 | CD7 | DAP10 | none |
| TAG-72 | CD7 | MyD88 | none |
| TAG-72 | CD7 | CD7 | none |
| TAG-72 | CD7 | DAP12 | none |
| TAG-72 | CD7 | MyD88 | none |
| TAG-72 | CD7 | CD7 | none |
| TAG-72 | BTNL3 | CD28 | none |
| TAG-72 | BTNL3 | CD8 | none |
| TAG-72 | BTNL3 | CD4 | none |
| TAG-72 | BTNL3 | b2c | none |
| TAG-72 | BTNL3 | CD137/41BB | none |
| TAG-72 | BTNL3 | ICOS | none |
| TAG-72 | BTNL3 | CD27 | none |
| TAG-72 | BTNL3 | CD28δ | none |
| TAG-72 | BTNL3 | CD80 | none |
| TAG-72 | BTNL3 | CD86 | none |
| TAG-72 | BTNL3 | OX40 | none |
| TAG-72 | BTNL3 | DAP10 | none |
| TAG-72 | BTNL3 | MyD88 | none |
| TAG-72 | BTNL3 | CD7 | none |
| TAG-72 | BTNL3 | DAP12 | none |
| TAG-72 | BTNL3 | MyD88 | none |
| TAG-72 | BTNL3 | CD7 | none |
| TAG-72 | NKG2D | CD28 | none |
| TAG-72 | NKG2D | CD8 | none |
| TAG-72 | NKG2D | CD4 | none |
| TAG-72 | NKG2D | b2c | none |
| TAG-72 | NKG2D | CD137/41BB | none |
| TAG-72 | NKG2D | ICOS | none |
| TAG-72 | NKG2D | CD27 | none |
| TAG-72 | NKG2D | CD28δ | none |
| TAG-72 | NKG2D | CD80 | none |
| TAG-72 | NKG2D | CD86 | none |
| TAG-72 | NKG2D | OX40 | none |
| TAG-72 | NKG2D | DAP10 | none |
| TAG-72 | NKG2D | MyD88 | none |
| TAG-72 | NKG2D | CD7 | none |
| TAG-72 | NKG2D | DAP12 | none |
| TAG-72 | NKG2D | MyD88 | none |
| TAG-72 | NKG2D | CD7 | none |

In some embodiments, the anti-TAG-72 binding agent is single chain variable fragment (scFv) antibody. The affinity/specificity of an anti-TAG-72 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-TAG-72 $V_H$ domain the following CDR domains: CDR1: DHAIH (SEQ ID NO:19), CDR2: WIGYFSPGNDDFKYNERFKG (SEQ ID NO:20), and CDR3: LNMAY (SEQ ID NO:21). In some embodiments, the anti-TAG-72 $V_L$T comprises the following CDR domains: CDR1: KSSQSLLYSGNQKNYLA (SEQ ID NO:22), CDR2: WASARES (SEQ ID NO:23), and CDR3: QQYYSYPLT (SEQ ID NO:24).

In some cases, the anti-TAG-72 $V_H$ domain comprises the amino acid sequence QVQLQQSDAELVKPGASVKISCK-ASGYTFTDHAIHWVKQNPEQGLEWI-GYFSPGNDDFKY NERFKGKATLTADKSSSTAY-VQLNSLTSEDSAVYFCTRSLNMAYWGQGTSVTVSS (SEQ ID NO:25), or a fragment or variant thereof able to bind TAG-72. In some cases, the anti-TAG-72 $V_L$ domain comprises the amino acid sequence DIVMSQSPSSLPVSVGEKVTLSCKSSQSLLYSGNQK-NYLAWYQQKPGQSPKLLIYWASAR ESGVPDRFTGSGSGTDFTLSISSVKTED-LAVYYCQQYYSYPLTFGAGTKLVLK (SEQ ID NO:26), or a fragment or variant thereof able to bind TAG-72.

In some cases, the anti-TAG-72 binding agent is an affinity maturated scFv. In some cases, the anti-TAG-72 has a dissociation constant ($K_D$) for TAG-72 that is less than 50 nM, 40 nM, 30 nM, 25 nM, 20 nM, 15 nM, or 10 nM.

In some embodiments, the anti-TAG-72 $V_H$ domain comprises the following CDR domains: CDR1: DHAIH (SEQ ID NO:1), and CDR3: LNMAY (SEQ ID NO:2). In some cases, the CDR2 domain is selected from the group consisting of

```
                                    (SEQ ID NO: 3)
WIGYFSPGNDDFRYNERFKG, (SEQ ID NO: 4)
WIGYFSPGNDDFKYNERYKG,
and (SEQ ID NO: 5)
WIGYFSPGNNDFKYNERFKG.
```

In some embodiments, the $V_H$ domain of the disclosed TAG-72 scFv antibodies comprises the amino acid sequence:
QVQLX$_1$X$_2$SX$_3$X$_4$X$_5$X$_6$X$_7$X$_8$PX$_9$X$_{10}$X$_{11}$X$_{12}$X$_{13}$X$_{14}$X$_{15}$CX$_{16}$X$_{17}$SGYTFTX$_{18}$DHAIHWVX$_{19}$QX$_{20}$PX$_{21}$
X$_{22}$X$_{23}$LWEX$_{24}$GYX$_{25}$SPX$_{26}$NX$_{27}$DX$_{28}$X$_{29}$YX$_{30}$X$_{31}$X$_{32}$ X$_{33}$X$_{34}$ GX$_{35}$X$_{36}$TX$_{37}$X$_{38}$X$_{39}$DX$_{40}$X$_{41}$X$_{42}$ X$_{43}$X$_{44}$X$_{45}$X$_{46}$X$_{47}$X$_{48}$LX$_{49}$SX$_{50}$X$_{51}$X$_{52}$X$_{53}$DX$_{54}$AVYX$_{55}$CX$_{56}$RSX$_{57}$ $X_{58}X_{59}X_{60}X_{61}$ WGQG$X_{62}$ $X_{63}X_{66}$TVSS (SEQ ID NO:29), wherein at least one of $X_{27}$=D or N, $X_{29}$=K or R, $X_{33}$=F or Y, or any combination thereof; and wherein $X_1$=V or Q; $X_2$=Q or E; $X_3$=D or G; $X_4$=A or P; $X_5$=E or G; $X_6$=L or V; $X_7$=V or K; $X_8$=K or R; $X_9$=G or S; $X_{10}$=A or Q; $X_{11}$=S or T; $X_{12}$=V or L; $X_{13}$=K or S; $X_{14}$=I, L or V; $X_{15}$=S or T; $X_{16}$=K or T; $X_{17}$=A or V; $X_{18}$=T or nothing; $X_{19}$=K or R; $X_{20}$=N, K, P, or A; $X_{21}$=E or G; $X_{22}$=Q or R; $X_{23}$=G or R; $X_{24}$=I or M; $X_{25}$=F or I; $X_{26}$=G or Q; $X_{28}$=F or I; $X_{30}$=N or S; $X_{31}$=E or Q; $X_{32}$=R or K; $X_{34}$=K or Q; $X_{35}$=K or R; $X_{36}$=A or V; $X_{37}$=L, M, or I; $X_{38}$ T or L; $X_{39}$=A, V, or R; $X_{40}$=K or T; $X_{41}$=S or P; $X_{42}$=S, A; or K; $X_{43}$=S or N; $X_{44}$=T or Q; $X_{45}$=A, V, or F; $X_{46}$=Y or S; $X_{47}$=V, M, or L; $X_{48}$=Q, E, or R; $X_{49}$=N or S; $X_{50}$=L or V; $X_{51}$=T, P, or R; $X_{52}$=S or A; $X_{53}$=E, N, or A; $X_{54}$=S or T; $X_{55}$=F or Y; $X_{53}$=T, R, or A; $X_{57}$=L, F, or Y; $X_{58}$=N, Y, or S; $X_{50}$=M or G; $X_{60}$=A, N, D or H; $X_{61}$=Y, S, or nothing; $X_{62}$=T or S; $X_{63}$=S, T, or L; and $X_{64}$=V or L.

Therefore, in some cases, the CDR2 domain comprises the amino acid sequence W$X_{24}$ G Y$X_{25}$SP$X_{26}$N$X_{27}$D$X_{28}X_{29}$ Y$X_{30}X_{31}X_{32}X_{33}X_{34}$G (SEQ ID NO:30), wherein at least one of $X_{27}$=D or N, $X_{29}$=K or R, $X_{33}$=F or Y, or any combination thereof; and wherein $X_{24}$=I or M; $X_{25}$=F or I; $X_{26}$=G or Q; $X_{28}$=F or I; $X_{30}$=N or S; $X_{31}$=E or Q; $X_{32}$=R or K; $X_{34}$=K or Q.

In some cases, the TAG-72 $V_H$ domain is selected from the group consisting of:

```
                                        (SEQ ID NO: 31)
QVQLQQSDAELVKPGASVKISCKASGYTFTDHAIHWVKQNPEQGLEWIGY

FSPGNX1DFX2YNERX3KGKATLTADKSSSTAYVQLNSLTSEDSAVYFCT

RSLNMAYWGQGTSVTVSS;

(SEQ ID NO: 32)
QVQLQQSDAELVKPGASVKISCKASGYTFTTDHAIHWVKQNPEQGLEWIG

YFSPQNX1DFX2YNERX3KGKATLTADKSSSTAYVQLNSLTSNDSAVYFC

TRSLNMAYWGQGTSVTVSS;

(SEQ ID NO: 33)
QVQLQQSDAELVKPGASVKISCKASGYTFTTDHAIHWVKQNPEQGLEWIG

YISPQNX1DIX2YNEKX3KGKATLTADKSSSTAYMQLNSLTSNDSAVYFC

RRSFYGN-WGQGTTLTVSS;

(SEQ ID NO: 34)
QVQLQQSDAELVKPGASVKISCKASGYTFTTDHAIHWVKQKPEQGLEWIG

YISPQNX1DIX2YNEKX3KGKATLTADKPSNTVYMQLNSLTSNDSAVYFC

TRSLSGDSWGQGTTLTVSS;

(SEQ ID NO: 35)
QVQLVQSGAEVVKPGASVKISCKASGYTFTDHAIHWVKQNPGQRLEWIGY

FSPGNX1DFX2YNERX3KGKATLTADTSASTAYVELSSLPSEDTAVYFCT

RSLNMAYWGQGTLVTVSS;

(SEQ ID NO: 36)
QVQLQESGPGLVRPSQTLSLTCTVSGYTFTDHAIHWVRQPPGRGLEWIGY

ISPGNX1DIX2YNEKX3KGRVTMLVDTSKNQFSLRLSSVTAADTAVYYCA

RSYYGH-WGQGSLVTVSS;

(SEQ ID NO: 37)
QVQLVQSGAEVVKPGASVKISCKASGYTFTDHAIHWVKQNPGQRLEWIGY

FSPGNX1DFX2YSQKX3QGKATLTADTSASTAYVELSSLRSEDTAVYFCT

RSLNMAYWGQGTLVTVSS;

(SEQ ID NO: 38)
QVQLVQSGAEVVKPGASVKVSCKASGYTFTDHAIHWVRQNPGQRLEWMGY

FSPGNX1DFX2YSQKX3QGRVTITADTSASTAYMELSSLRSEDTAVYFCT

RSLNMAYWGQGTLVTVSS;

(SEQ ID NO: 39)
QVQLVQSGAEVKKPGASVKVSCKASGYTFTDHAIHWVRQAPGQRLEWMGY

FSPGNX1DFX2YSQKX3QGRVTITADTSASTAYMELSSLRSEDTAVYFCT

RSLNMAYWGQGTLVTVSS;

(SEQ ID NO: 40)
QVQLQQSDAELVKPGASVKISCKASGYTFTDHAIHWVKQNPEQGLEWIGY

FSPGNX1DFX2YNERX3KGKATLTADKSSSTAYVQLNSLTSEDSAVYFCT

RSLNMAYWGQGTTLTVSS;

(SEQ ID NO: 41)
QVQLVQSGAEVKKPGASVKVSCKASGYTFTDHAIHWVRQAPGQRLEWMGY

FSPGNX1DFX2YSQKX3QGRVTITADKSASTAYMELSSLRSEDTAVYYCA

RSLNMAYWGQGTLVTVSS;

(SEQ ID NO: 42)
QVQLVQSGAEVKKPGASVKVSCKASGYTFTDHAIHWVRQAPGQRLEWMGY

FSPGNX1DFX2YSQKX3QGRVTITRDKSASTAYMELSSLRSEDTAVYYCA

RSLNMAYWGQGTLVTVSS;

(SEQ ID NO: 43)
QVQLVQSGAEVKKPGASVKVSCKASGYTFTDHAIHWVRQAPGQRLEWMGY

FSPGNX1DFX2YSQKX3QGRVTITADTSASTAYMELSSLRSEDTAVYYCA

RSLNMAYWGQGTLVTVSS;
and (SEQ ID NO: 44)
QVQLVQSGAEVKKPGASVKVSCKASGYTFTDHAIHWVRQAPGQRLEWMGY

FSPGNX1DFX2YSQKX3QGVTITRDTSASTAYMELSSLRSEDTAVYYCAR

SLNMAYWGQGTLVTVSS;
``` wherein at least one of $X_1$=D or N, $X_2$=K or R, $X_3$=F or Y, or any combination thereof.

In some cases, the anti-TAG-72 $V_H$ domain is selected from the group consisting of:

```
                                        (SEQ ID NO: 6)
QVQLQQSDAELVKPGASVKISCKASGYTFTDHAIHWVKQNPEQGLEWIGY

FSPGNDDFRYNERFKGKATLTADKSSSTAYVQLNSLTSEDSAVYFCTRSL

NMAYWGQGTSVTVSS;

(SEQ ID NO: 7)
QVQLQQSDAELVKPGASVKISCKASGYTFTDHAIHWVKQNPEQGLEWIGY

FSPGNDDFKYNERYKGKATLTADKSSSTAYVQLNSLTSEDSAVYFCTRSL

NMAYWGQGTSVTVSS;
and (SEQ ID NO: 8)
QVQLQQSDAELVKPGASVKISCKASGYTFTDHAIHWVKQNPEQGLEWIGY
```

FSPGNNDFKYNERFKGKATLTADKSSSTAYVQLNSLTSEDSAVYFCTRSL

NMAYWGQGTSVTVSS.

In some embodiments, the anti-TAG-72 $V_L$ domain comprises the following CDR domains: CDR1: KSSQSLLY-SGNQKNYLA (SEQ ID NO:9), CDR2: WASARES (SEQ ID NO:10), and CDR3: QQYYSYPLT (SEQ ID NO:11). In some embodiments, the anti-TAG-72 $V_L$ domain comprises the CDR1 domain KSSQSLLYSGNHKNYLA (SEQ ID NO:12). In some embodiments, when the CDR2 sequence of the anti-TAG-72 $V_H$ domain has the amino acid sequence SEQ ID NO:3, the CDR1 sequence of the anti-TAG-72 $V_L$ domain has the amino acid sequence SEQ ID NO:12.

In some cases, the TAG-72 $V_L$ domain comprises the amino acid sequence DIVMX$_1$QSPX$_2$SLX$_3$VSX$_4$GX$_5$KX$_6$TX$_7$X$_8$CKSSQSX$_9$LYSX$_{10}$NHKNYLAWYQQKPGQX$_{11}$PKLLIYWASX$_{12}$RESGVPDRFX$_{13}$GSGSGTDFTLX$_{14}$ISSX$_{15}$X$_{16}$X$_{17}$EDX$_{18}$AVYYCQQYYSYPLTFGX$_{19}$GTKX$_{20}$X$_{21}$X$_{22}$K (SEQ ID NO:45), wherein X$_1$=S or T; X$_2$=S or D; X$_3$=P or A; X$_4$=L or V; X$_5$=E or D; X$_6$=V or A; X$_7$=L or I; X$_8$=S or N; X$_9$=L or V; X$_{10}$=G or S; X$_{11}$=S or P; X$_{12}$=A or T; X$_{13}$=T or S; X$_{14}$=S or T; X$_{15}$=V or L; X$_{16}$=K or Q; X$_{17}$=T or A; X$_{18}$=L or V; X$_{19}$=A or Q; X$_{20}$=L or V; X$_{21}$=V or E; and X$_{22}$=L or I.

Therefore, in some cases, the the TAG-72 $V_L$ domain comprises the CDR1 domain KSSQSX$_1$LYSX$_2$NHKNYLA (SEQ ID NO:46), wherein X$_1$=L or V, and X$_2$=G or S.

In some cases, the anti-TAG-72 domain is selected from the group consisting of:

(SEQ ID NO: 13)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYS

PLTFGAGTKLVLK,
and (SEQ ID NO: 14)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSYP

LTFGAGTKLVLK.

In some cases, the TAG-72 $V_L$ domain is selected from the group consisting of:

(SEQ ID NO: 47)
DIVMSQSPDSLAVSLGERVTLNCKSSQSLLYSGNHKNYLAWYQQKPGQSP

KLLIYWASARESGVPDRFSGSGSGTDFTLTISSVQAEDVAVYYCQQYYSY

PLTFGAGTKLELK;

(SEQ ID NO: 48)
DIVMSQSPDSLAVSLGERVTLNCKSSQSVLYSGNHKNYLAWYQQKPGQSP

KLLIYWASARESGVPDRFSGSGSGTDFTLTISSVQAEDVAVYYCQQYYSY

PLTFGAGTKLELK;

(SEQ ID NO: 49)
DIVMSQTPDSLAVSLGERATINCKSSQSVLYSGNHKNYLAWYQQKPGQSP

KLLIYWASARESGVPDRFSGSGSGTDFTLTISSLQAEDVAVYYCQQYYSY

PLTFGAGTKLEIK;

(SEQ ID NO: 50)
DIVMSQTPDSLAVSLGERATINCKSSQSVLYSGNHKNYLAWYQQKPGQPP

KLLIYWASARESGVPDRFSGSGSGTDFTLTISSLQAEDVAVYYCQQYYSY

PLTFGQGTKLEIK;

(SEQ ID NO: 51)
DIVMSQSPSSLPVSVGDKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVIK;

(SEQ ID NO: 52)
DIVMSQTPDSLAVSLGERATINCKSSQSVLYSSNHKNYLAWYQQKPGQPP

KLLIYWASTRESGVPDRFSGSGSGTDFTLTISSLQAEDVAVYYCQQYYSY

PLTFGGGTKVEIK;
and (SEQ ID NO: 53)
DIVMTQSPDSLAVSLGERATINCKSSQSVLYSGNHKNYLAWYQQKPGQPP

KLLIYWASTRESGVPDRFSGSGSGTDFTLTISSLQAEDVAVYYCQQYYSY

PLTFGGGTKVEIK.

The $V_H$ and $V_L$ domains of the anti-TAG-72 scFv antibodies are preferably separated by a peptide linker. In some embodiments, the peptide linker comprises the amino acid sequence LSADDAKKDAAKKDDAKKDDAKKDL (SEQ ID NO: 15).

Therefore, in some embodiments, the disclosed TAG-72 scFv antibodies have an amino acid sequence selected from the group consisting of:

(SEQ ID NO: 16)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFRYNE

RFKGKATLTADKSSSTAYVQLNSLTSEDSAVYFCTRSLNMAYWGQGTSVT

VSS, (SEQ ID NO: 17)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKGLQVQLQQSDAELV

KPGASVKISCKASGYTFTDHAIHWVKQNPEQGLEWIGYFSPGNDDFKYNE

RYKGKATLTADKSSSTAYVQLNSLTSEDSAVYFCTRSLNMAYWGQGTSVT

VSS, (SEQ ID NO: 18)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNNDFKYNE

RFKGKATLTADKSSSTAYVQLNSLTSEDSAVYFCTRSLNMAYWGQGTSVT

VSS.

In some embodiments, the anti-TAG-72 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target TAG-72 and at least one additional tumor antigen. Also disclosed are CARs designed to work only in conjunction with another CAR that binds a different antigen, such as a tumor antigen. For example, in these embodiments, the endodomain of the disclosed CAR can contain only an signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LACE-la, LMP2, NCAM, p53, p53 mutant, Ras mutant, gpIOO, prostein, OR51E2, PANX3, PSMA, PSCA, Her2/neu, hTERT, HMWMAA, HAVCR1, VEGFR2, PDGFR-beta, survivin and telomerase, legumain, HPV E6, E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed TAG-72-specific CARs that allow expression of the TAG-72-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells. Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of α and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against TAG-72-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to TAG-72.

Adoptive transfer of immune effector cells expressing chimeric antigen receptors is a promising anti-cancer therapeutic. Following the collection of a patient's immune effector cells, the cells may be genetically engineered to express the disclosed TAG-72-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione;

adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any TAG-72-expressing cell in a subject undergoing unregulated growth, invasion, or metastasis. Cancers that express TAG-72 include prostate cancer, ovarian cancer, adenocarcinoma of the lung, breast cancer, endometrial cancer, gastric cancer, colon cancer, and pancreatic cancer. TAG-72 has also been found on Jurkat cells. In some aspects, the cancer is a gallbladder cancer, exocrine adenocarcinoma, or apocrine adenocarcinomas.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies. In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB(CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)–negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos.

6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substations (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Affinity Maturation of TAG-72 scSv Antibody

Based on the sequence for TAG-72 antibody and a choice of linker, the following two scFv constructs were produced:

Ab3890 (VH-linker-VL) -
(SEQ ID NO: 27)
QVQLQQSDAELVKPGASVKISCKASGYTFTDHAIHWVKQNPEQGLEWIGY

FSPGNDDFKYNERFKGKATLTADKSSSTAYVQLNSLTSEDSAVYFCTRSL

NMAYWGQGTSVTVSSLSADDAKKDAAKKDDAKKDDAKKDLDIVMSQSPSS

LPVSVGEKVTLSCKSSQSLLYSGNQKNYLAWYQQKPGQSPKLLIYWASAR

ESGVPDRFTGSGSGTDFTLSISSVKTEDLAVYYCQQYYSYPLTFGAGTKL

VLK;
and

Ab3890 (VL-linker-VH) -
(SEQ ID NO: 28)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFKYNE

RFKGKATLTADKSSSTAYVQLNSLTSEDSAVYFCTRSLNMAYWGQGTSVT

VSS.

scFvs were cloned into a vector and produced as purified protein and phage. Both scFvs were successfully purified.

Antigen S was re-suspended according to manufacturer's instructions. 1 mg of the Antigen S was biotinylated using amine coupling kit (EZ Link Biotinylation kit, Thermo, 21955). Protein was analyzed by TruHits assay (to evaluate biotinylation) and SDS-PAGE, and successful biotinylation was confirmed.

Figure 1B:
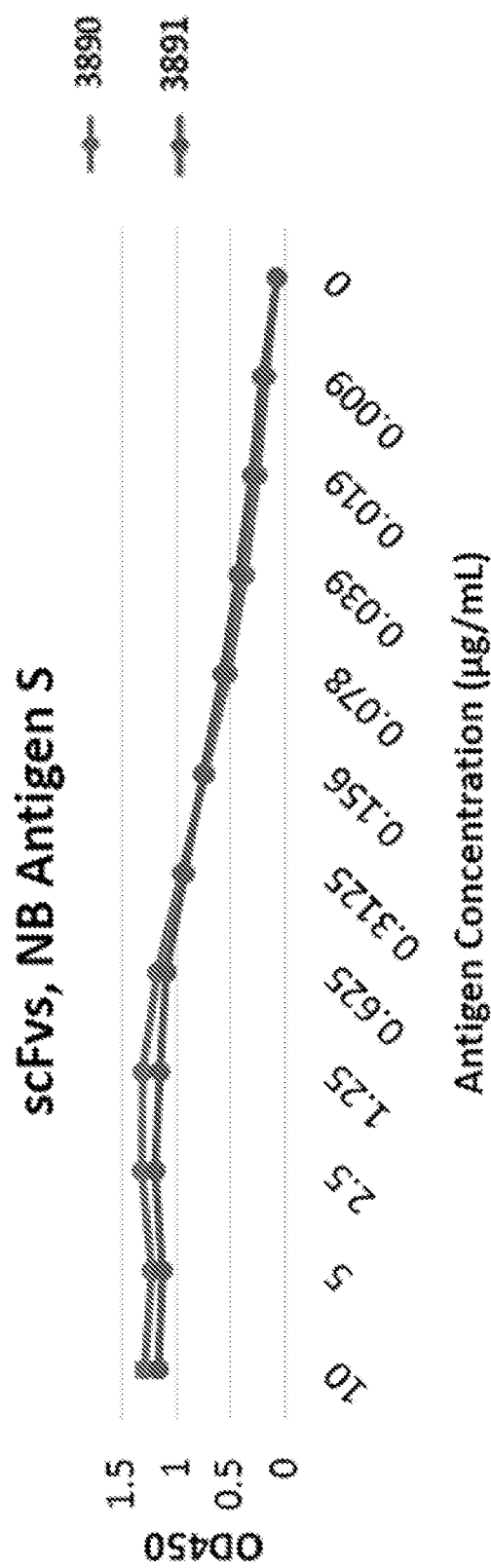

As shown in FIGS. 1A and 1B, both scFvs bound to biotinylated and unmodified antigen S. All scFvs were used at 1 μg/ml. The secondary antibody was anti-FLAG-HRP (Abcam, ab49763, 1:5000).

Figure 2A:
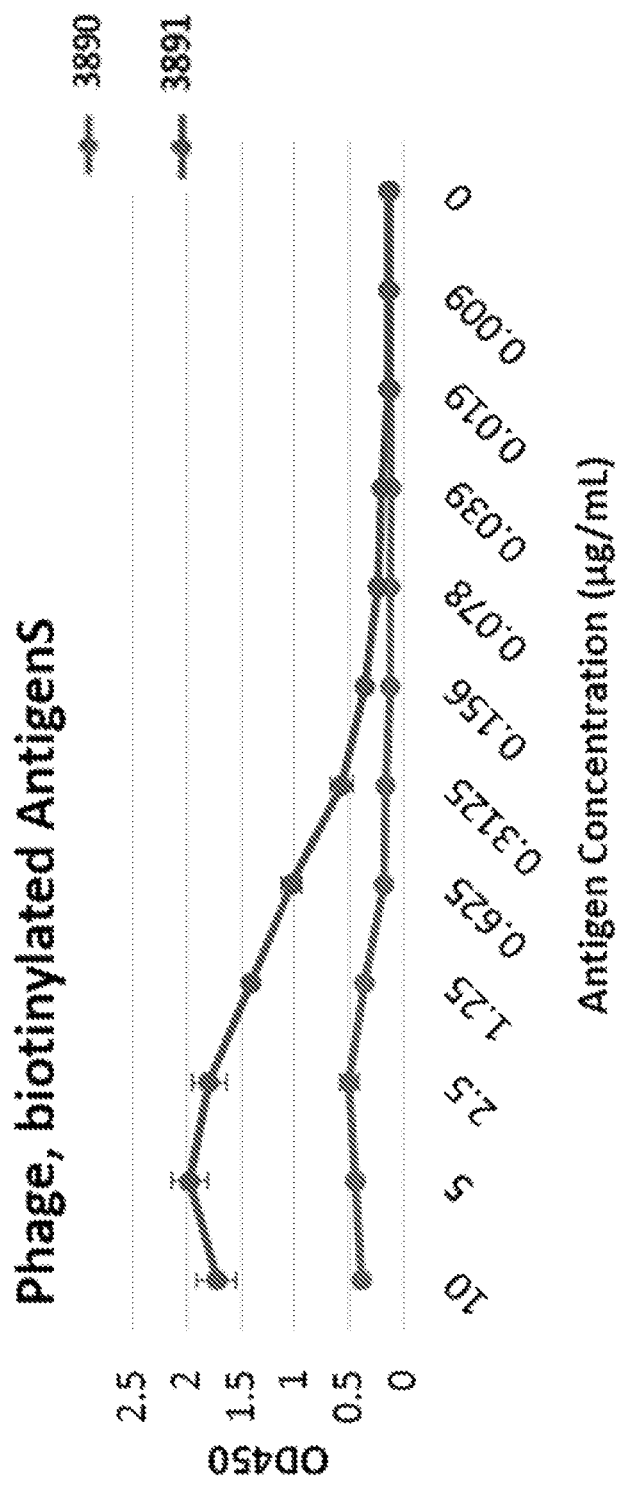
FIGS. 2A and 2B show phage binding of scFvs Ab3890 and Ab3891 to biotinylated antigen S FIG. 2A) and unmodified antigen S(FIG. 2B).
Figure 2B:
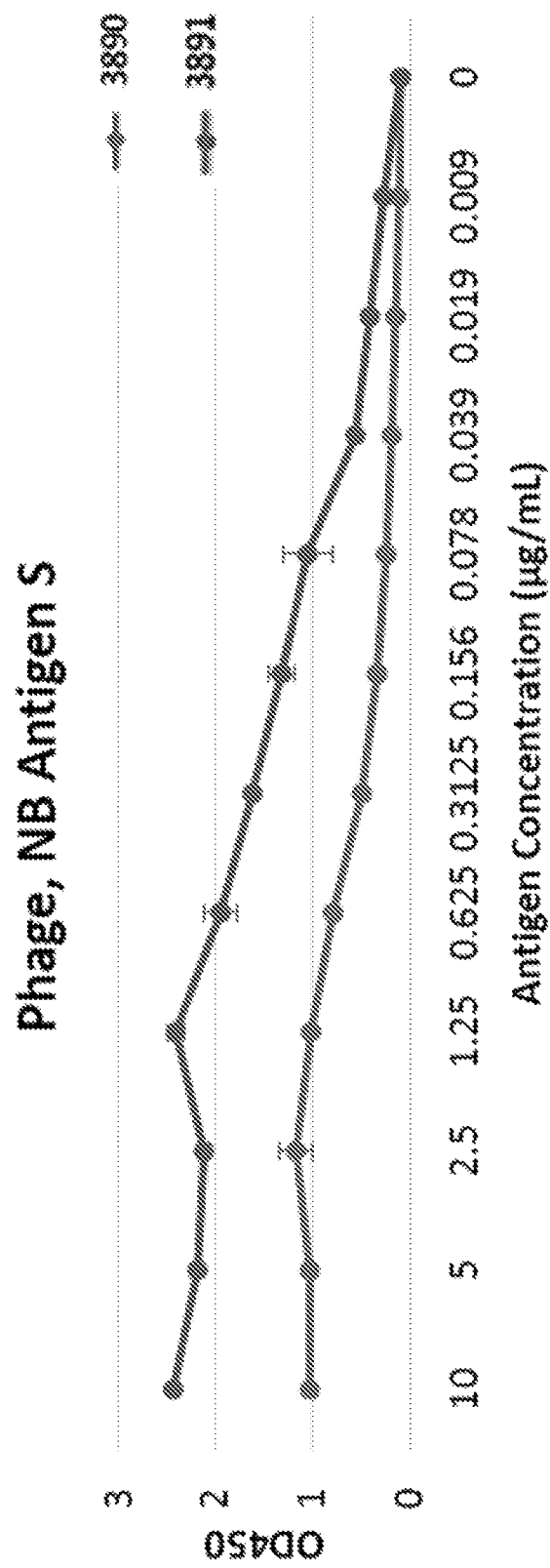

However, as shown in FIGS. 2A and 2B, Ab3891 had a better phage binding profile than Ab3890. The secondary antibody was anti-m13-HRP (GE Healthcare, 27-9521, 1:5000). Therefore, Ab3891 was selected for affinity maturation.

Standard mutagenesis library was prepared from Ab3891 and quality controlled by sequencing. The library was screened through 3 rounds of affinity maturation using standard protocol. Biotinylated Antigen S was used as the target. The following three unique clones with CDR mutations were identified:

Ab4116-
(SEQ ID NO: 16)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFRYNE

RFKGKATLTADKSSSTAYVQLNSLTSEDSAVYFCTRSLNMAYWGQGTSVT

VSS,

Ab4117-
(SEQ ID NO: 17)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKGLQVQLQQSDAELV

KPGASVKISCKASGYTFTDHAIHWVKQNPEQGLEWIGYFSPGNDDFKYNE

RYKGKATLTADKSSSTAYVQLNSLTSEDSAVYFCTRSLNMAYWGQGTSVT

VSS,

Ab4118-

(SEQ ID NO: 18)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNNDFKYNE

RFKGKATLTADKSSSTAYVQLNSLTSEDSAVYFCTRSLNMAYWGQGTSVT

VSS.

Figure 3A:
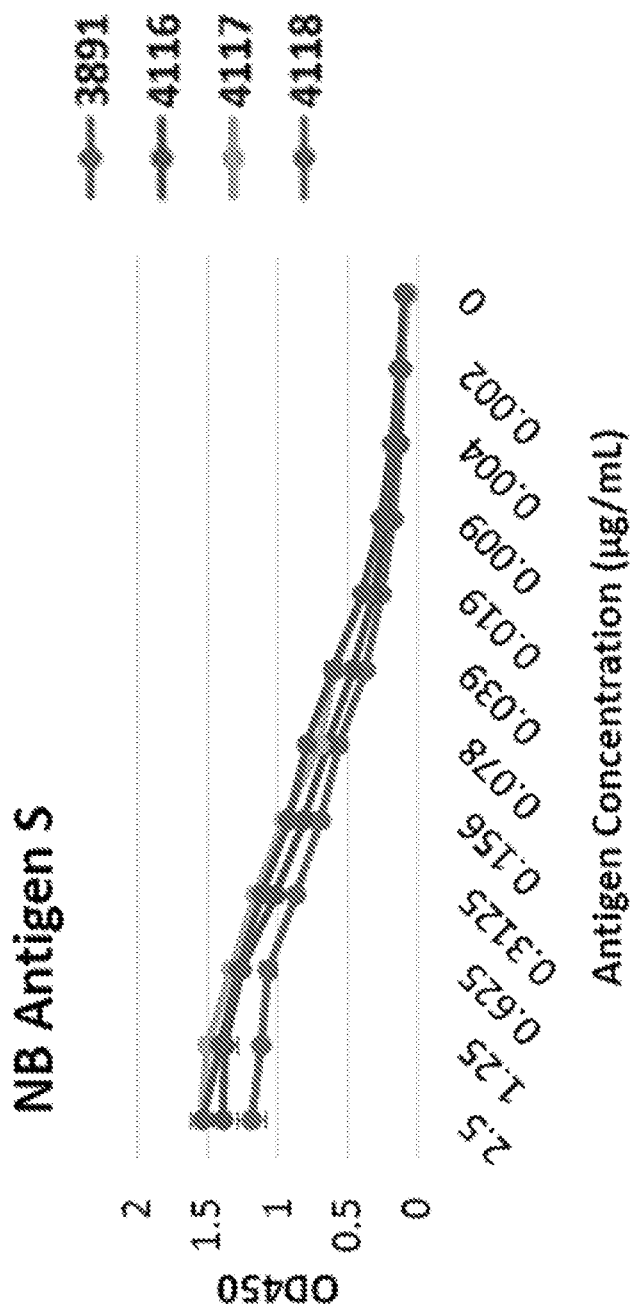
FIGS. 3A and 3B show binding of scFvs Ab3891, Ab4116, Ab4117, and Ab4118 to unmodified antigen S(FIG. 3A) and biotinylated antigen S(FIG. 3B).
Figure 3B:
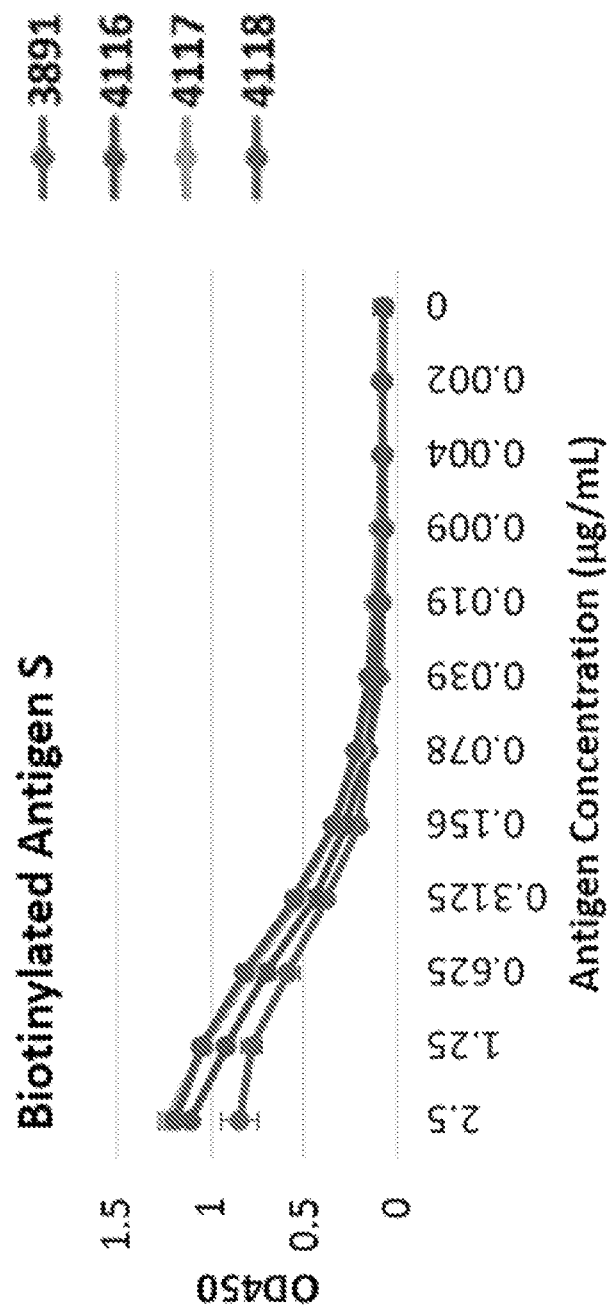
Figure 4B:
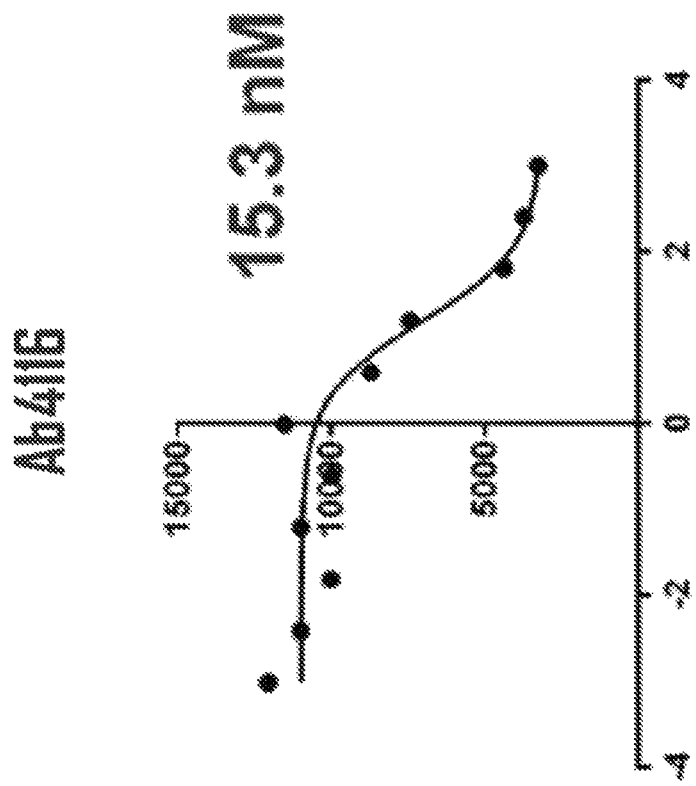
FIGS. 4A to 4D show dissociation constants (KD) for Ab3891 (FIG. 4A), Ab4116 (FIG. 4B), Ab4117 (FIG. 4C), and Ab4118 (FIG. 4D) as determined by Alpha Screen.
Figure 4A:
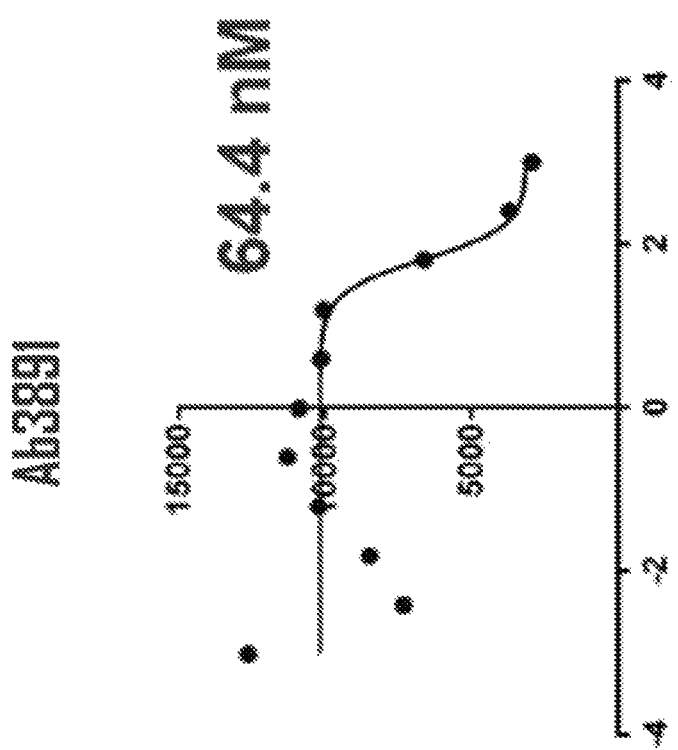
Figure 4D:
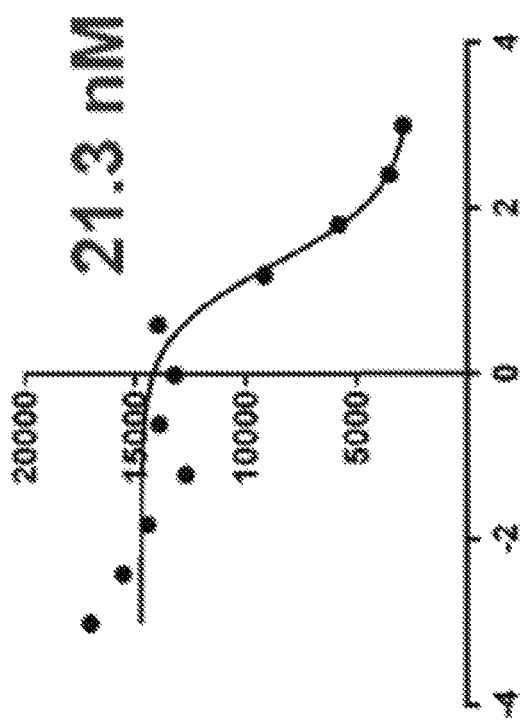
Figure 4C:
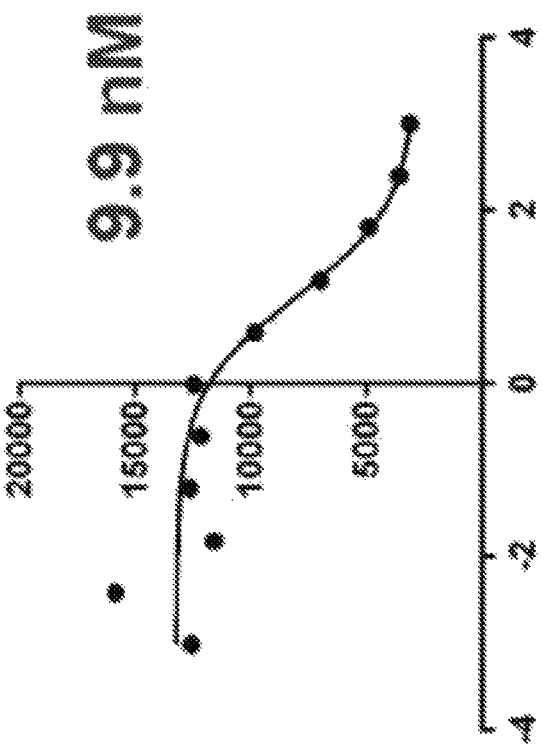

As shown in FIGS. 3A and 3B, all matured clones shows moderate improvement compared to Ab3891 when evaluated by traditional ELISA. All scFvs were used at 1 μg/ml. The secondary antibody was anti-FLAG-HRP (Abcam, ab49763, 1:5000).

FIGS. 4A to 4D show KD determination of the four scFvs by Alpha Screen. Based on this assay, there was a 3-6 fold improvement (FIG. 1A, Ab3891, 64.4 nM) (FIG. 1B, Ab4116, 15.3 nM) (FIG. 1C, Ab4117, 9.9 nM), (FIG. 1D, Ab4118, 21.3 nM). Therefore, the best clone was Ab4117 with a 6 fold affinity improvement achieved.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a TAG-72 antigen binding domain, a transmembrane domain, an intracellular signaling domain, and a co-stimulatory signaling region, wherein the TAG-72 antigen binding domain is an affinity maturated single-chain variable fragment (scFv) of an antibody that specifically binds TAG-72, wherein the anti-TAG-72 scFv comprises a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence DHAIH (SEQ ID NO:1), wherein the CDR2 sequence of the $V_H$ domain has an amino acid sequence selected from the group consisting of WIGYFSPGNDDFRYNERFKG (SEQ ID NO:3), WIGYFSPGNDDFKYNERYKG (SEQ ID NO:4), and WIGYFSPGNNDFKYNERFKG (SEQ ID NO:5), wherein the CDR3 sequence of the $V_H$ domain comprises the amino acid sequence LNMAY (SEQ ID NO:2), wherein the CDR1 sequence of the $V_L$ domain comprises the amino acid sequence selected from the group consisting of KSSQSLLYSGNQKNYLA (SEQ ID NO:9) and KSSQSLLYSGNHKNYLA (SEQ ID NO:12), wherein the CDR2 sequence of the $V_L$ domain comprises the amino acid sequence WASARES (SEQ ID NO:10), and wherein the CDR3 sequence of the $V_L$ domain comprises the amino acid sequence QQYYSYPLT (SEQ ID NO:11).

2. The CAR polypeptide of claim 1, wherein the anti-TAG-72 scFv $V_H$ domain comprises the amino acid sequence SEQ ID NO:6, SEQ ID NO:7, or SEQ ID NO:8.

3. The CAR polypeptide of claim 1, wherein the anti-TAG-72 scFv $V_L$ domain comprises the amino acid sequence SEQ ID NO:13 or SEQ ID NO:14.

4. The CAR polypeptide of claim 1, wherein the anti-TAG-72 scFv comprises an amino acid sequence selected from the group consisting of SEQ ID NO:16, SEQ ID NO:17, and SEQ ID NO:18.

5. The CAR polypeptide of claim 1, wherein the costimulatory signaling region comprises the cytoplasmic domain of a costimulatory molecule selected from the group consisting of CD27, CD28, 4-1 BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

6. The CAR polypeptide of claim 1, wherein the CAR polypeptide is defined by the formula:

SP-TAG72-HG-TM-CSR-SD; or

SP-TAG72-HG-TM-CSR-SD, wherein "SP" represents a signal peptide,
wherein "TAG 72" represents a TAG-72-binding region,
wherein "HG" represents an optional hinge domain,
wherein "TM" represents a transmembrane domain,
wherein "CSR" represents a co-stimulatory signaling region,
wherein "ISD" represents an intracellular signaling domain, and
wherein "-" represents a linker.

7. The CAR polypeptide of claim 1, wherein the intracellular signaling domain comprises a CD3 zeta (CD3ζ) signaling domain.

8. An isolated nucleic acid sequence encoding the CAR polypeptide of claim 1.

9. A vector comprising the isolated nucleic acid sequence of claim 8.

10. A cell comprising the vector of claim 9.

11. The cell of claim 10, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, and any combination thereof.

12. The cell of claim 11, wherein the cell exhibits an anti-tumor immunity when the antigen binding domain of the CAR binds to TAG-72.

13. A method of providing an anti-tumor immunity in a human subject with a TAG-72-expressing cancer, the method comprising administering to the human subject an effective amount of an immune effector cell genetically modified to express the CAR polypeptide of claim 1, thereby providing an anti-tumor immunity in the human subject.

14. The method of claim 13, wherein the immune effector cell is selected from the group consisting of a T cell, a Natural Killer (NK) cell, a cytotoxic T lymphocyte (CTL), and a regulatory T cell.

15. The method of claim 13, further comprising administering to the subject a checkpoint inhibitor.

16. The method of claim 15, wherein the checkpoint inhibitor comprises an anti-PD-1 antibody, anti-PD-L1 antibody, anti-CTLA-4 antibody, or a combination thereof.

* * * * *